(12) United States Patent
Morrison

(10) Patent No.: US 12,059,435 B2
(45) Date of Patent: Aug. 13, 2024

(54) METHOD FOR ACCELERATING NERVE REGENERATION

(71) Applicant: THE JOHNS HOPKINS UNIVERSITY, Baltimore, MD (US)

(72) Inventor: Brett Morrison, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 168 days.

(21) Appl. No.: 17/412,127

(22) Filed: Aug. 25, 2021

(65) Prior Publication Data

US 2022/0062336 A1 Mar. 3, 2022

Related U.S. Application Data

(60) Provisional application No. 63/072,817, filed on Aug. 31, 2020.

(51) Int. Cl.
*A61K 35/15* (2015.01)
*A61P 25/00* (2006.01)
*C07K 14/47* (2006.01)

(52) U.S. Cl.
CPC .............. *A61K 35/15* (2013.01); *A61P 25/00* (2018.01); *C07K 14/47* (2013.01)

(58) Field of Classification Search
CPC ......... A61K 35/15; A61P 25/00; C07K 14/47; C07K 14/705; A01K 67/0275; C12N 5/0645
USPC .......... 435/320.1, 455; 530/387.3; 424/93.21
See application file for complete search history.

(56) References Cited

FOREIGN PATENT DOCUMENTS

WO   WO-2019136300 A2 * 7/2019 ............. A61K 47/68

OTHER PUBLICATIONS

Sheng et al., "3-Bromopyruvate inhibits the malignant phenotype of malignantly transformed macrophages and dendritic cells induced by glioma stem cells in the glioma microenvironment via miR-449a/MCT1". Biomed Pharmacother. Jan. 2020; 121:109610: pp. 1-7. (Year: 2020).*
Morrison et al., "Deficiency in Monocarboxylate Transporter 1 (MCT1) in Mice Delays Regeneration of Peripheral Nerves following Sciatic Nerve Crush". Exp Neurol. Jan. 2015; 263: pp. 1-24. (Year: 2015).*
Puri et al., "Monocarboxylate transporter 1 and 4 inhibitors as potential therapeutics for treating solid tumours: A review with structure activity relationship insights". Eur J Med Chem. Aug. 1, 2020; 199:112393: pp. 1-14. (Year: 2020).*
Liu et al., "Role of macrophages in peripheral nerve injury and repair". Neural Regen Res. Aug. 2019 ;14(8): pp. 1335-1342. (Year: 2019).*

* cited by examiner

*Primary Examiner* — Anne Marie S Wehbe
*Assistant Examiner* — Hanan Isam Abuzeineh
(74) *Attorney, Agent, or Firm* — DLA Piper LLP (US)

(57) ABSTRACT

Provided herein are methods and compositions for increasing nerve regeneration activity of a macrophage, and for inducing and accelerating nerve regeneration of an injured or damaged nerve. Methods and compositions provided herein include upregulating the expression of an MCT1 gene in a macrophage.

24 Claims, 23 Drawing Sheets

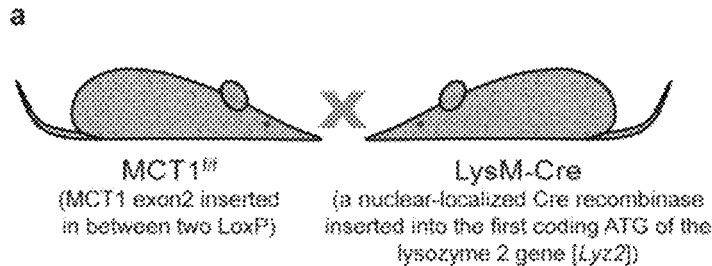
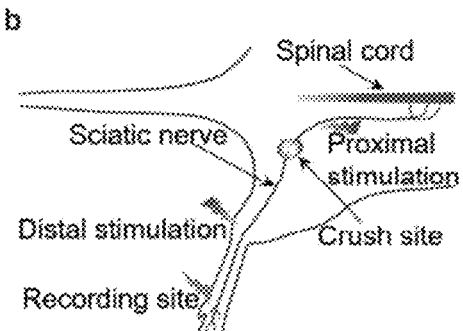
FIG. 1A
FIG. 1B
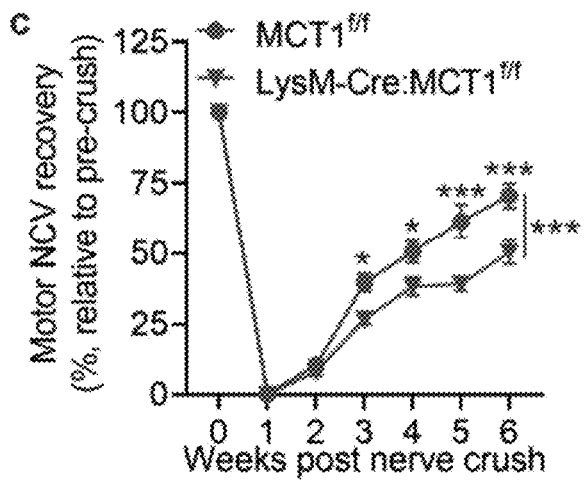
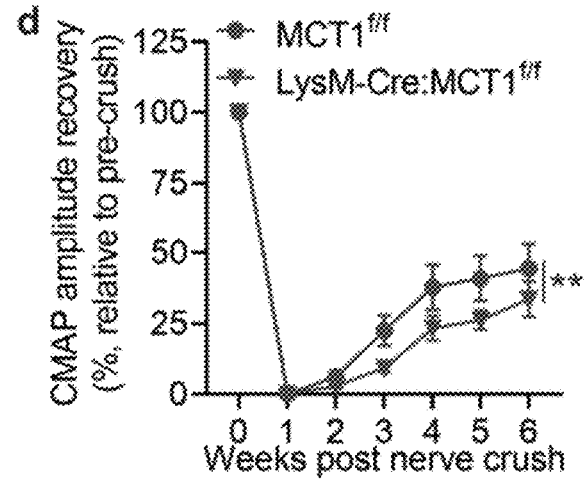
FIG. 1C
FIG. 1D
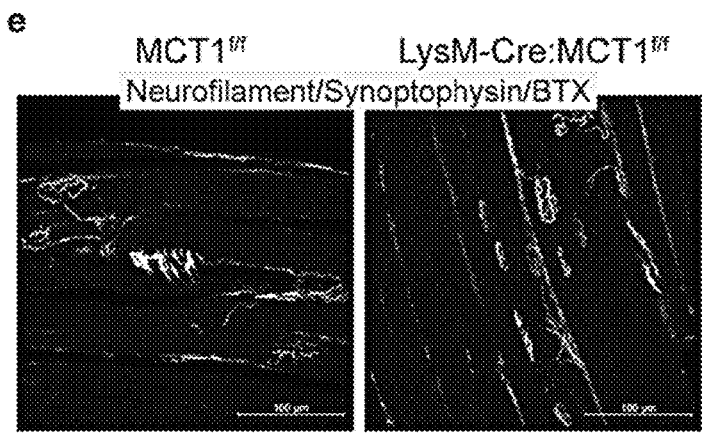
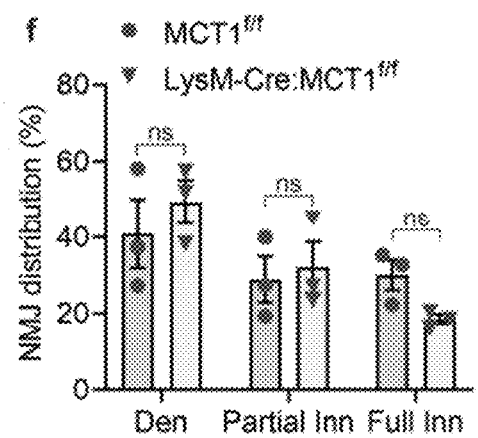
FIG. 1E
FIG. 1F

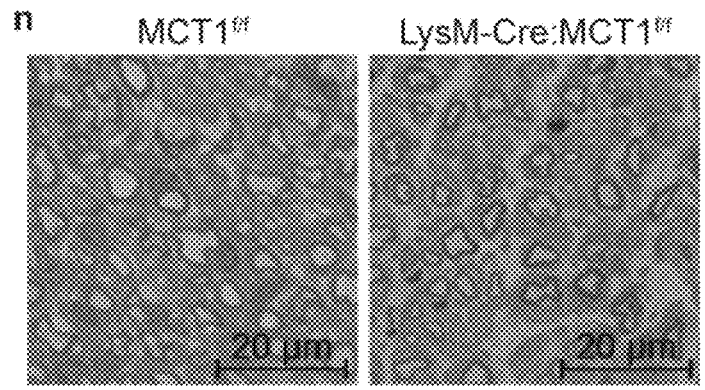
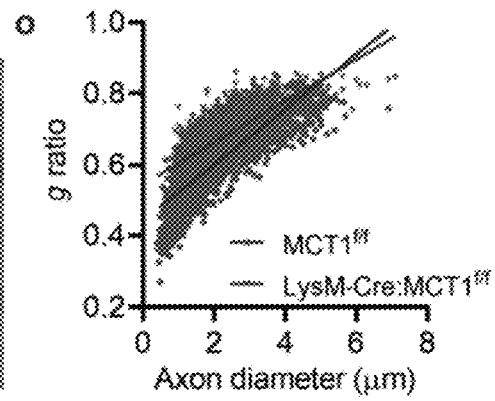
FIG. 1N  FIG. 1O
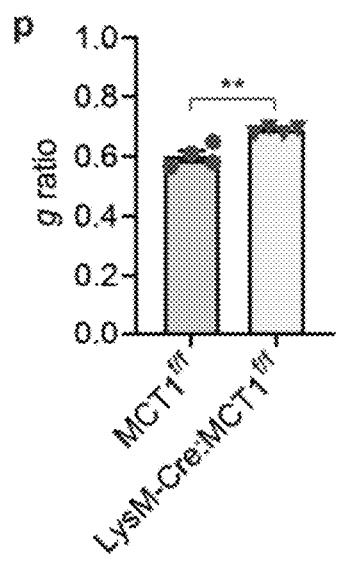
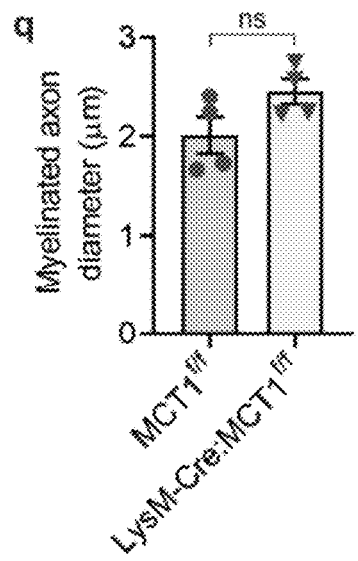
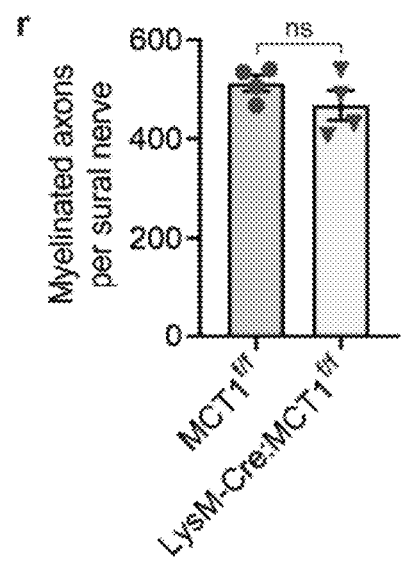
FIG. 1P  FIG. 1Q  FIG. 1R

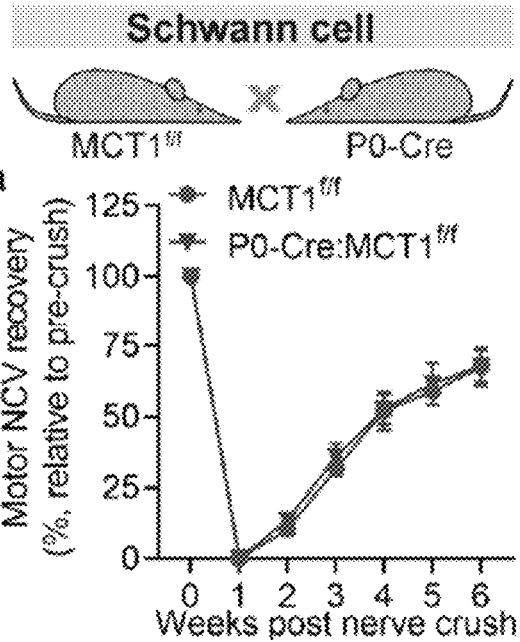
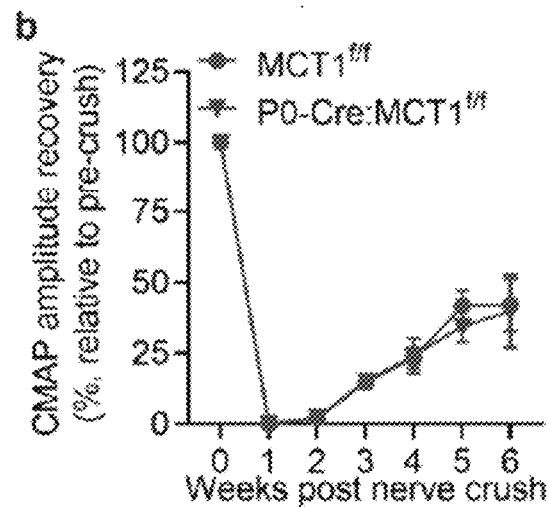
FIG. 2A  FIG. 2B
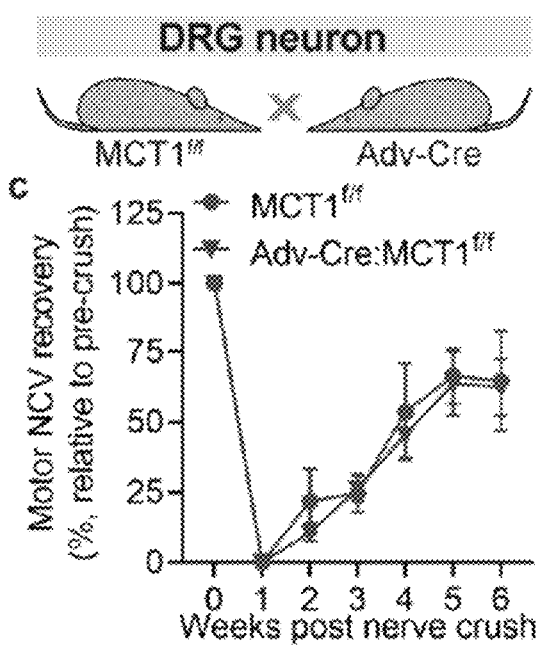
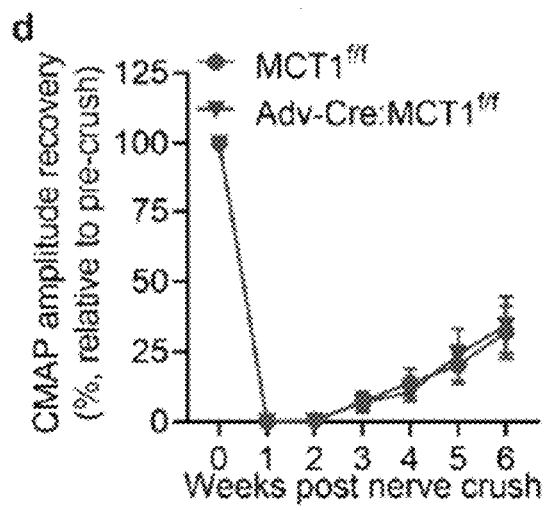
FIG. 2C  FIG. 2D

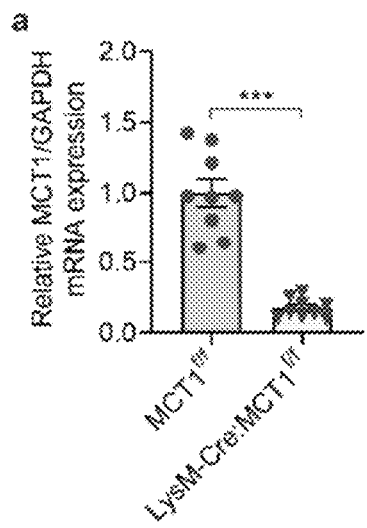
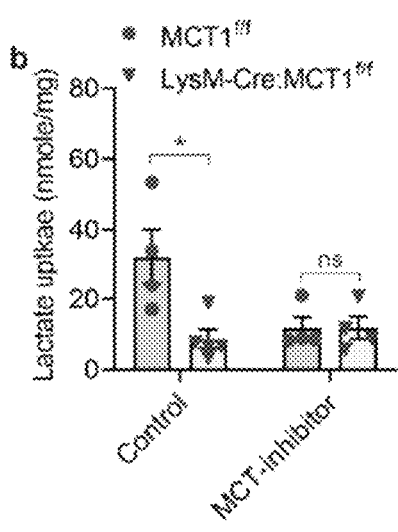
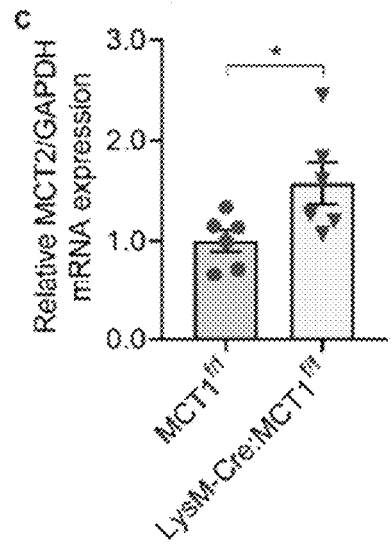
FIG. 3A　　　　　FIG. 3B　　　　　FIG. 3C
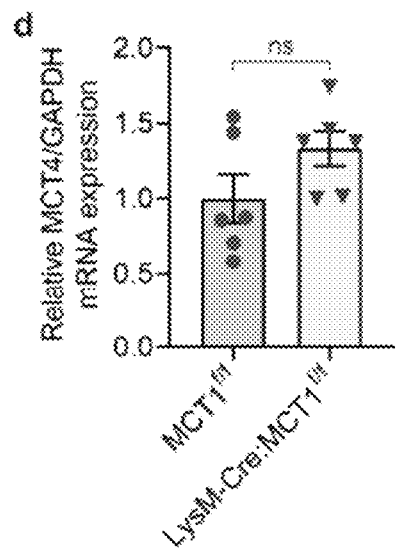
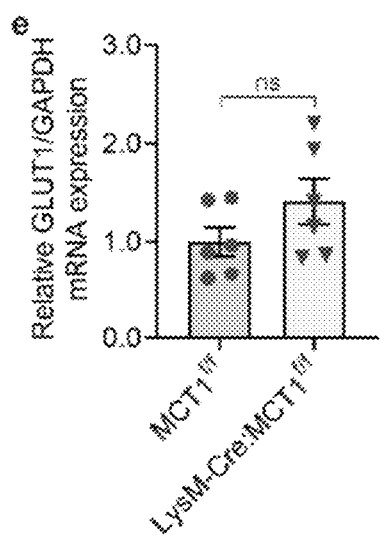
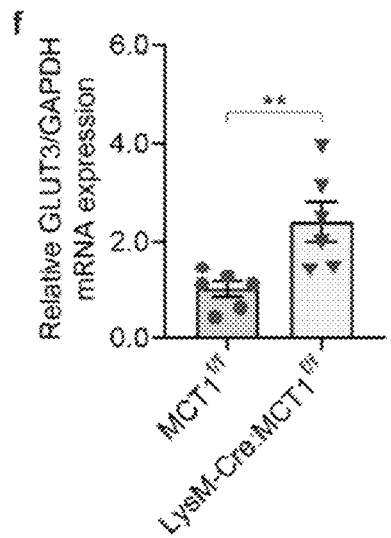
FIG. 3D　　　　　FIG. 3E　　　　　FIG. 3F

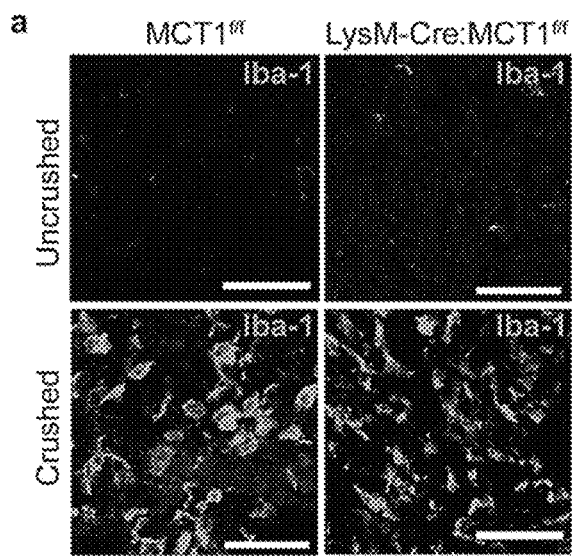
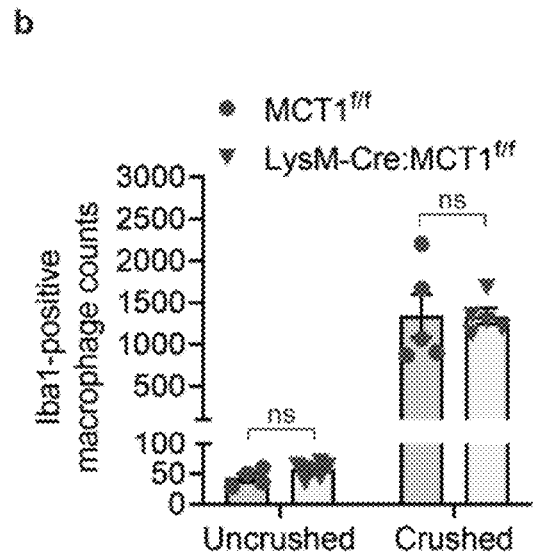
FIG. 7A
FIG. 7B
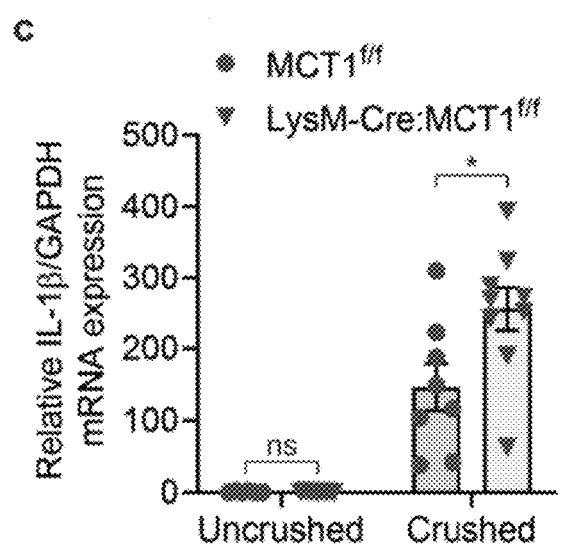
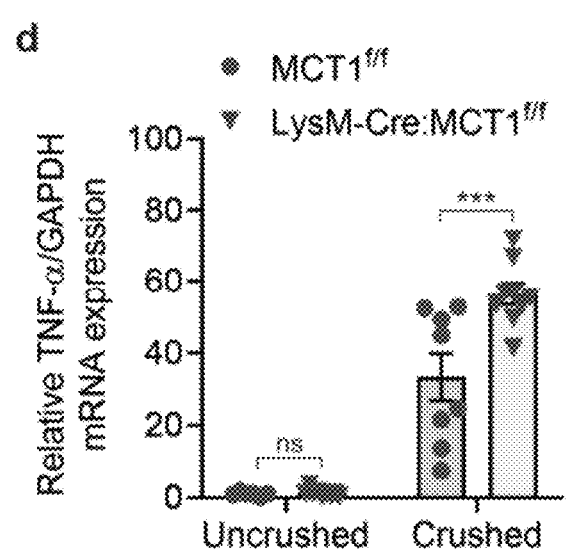
FIG. 7C
FIG. 7D

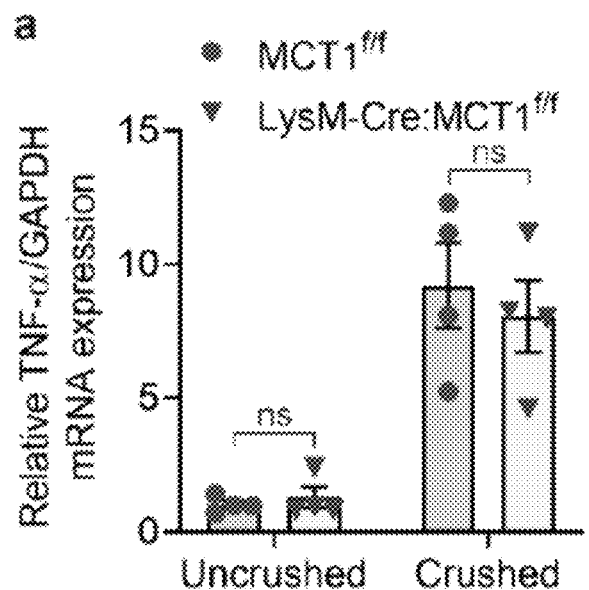
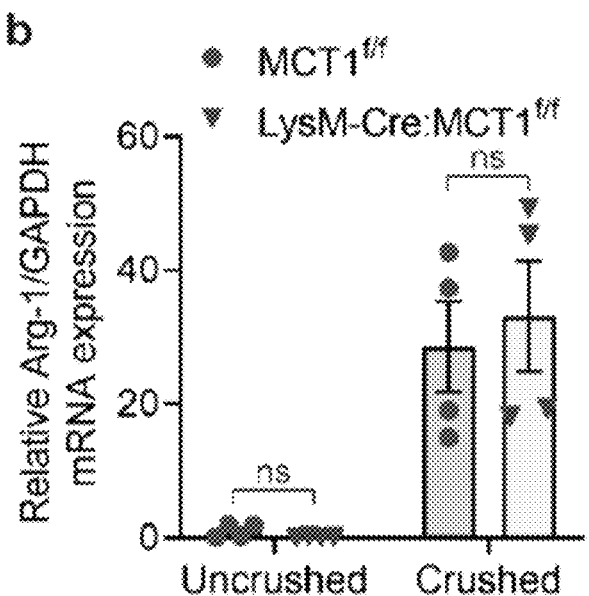
FIG. 9A
FIG. 9B
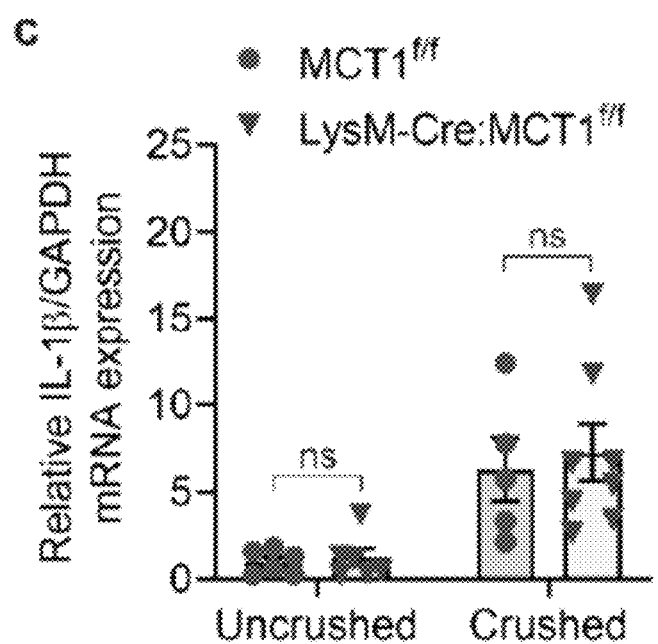
FIG. 9C

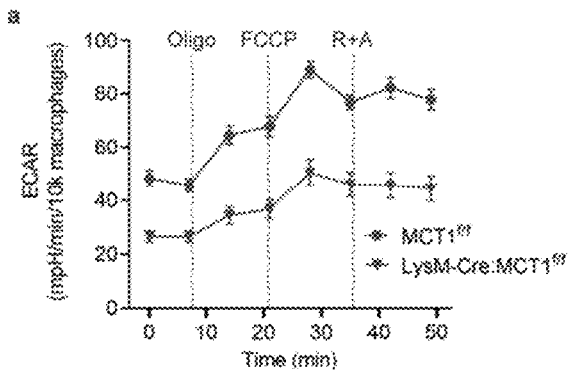
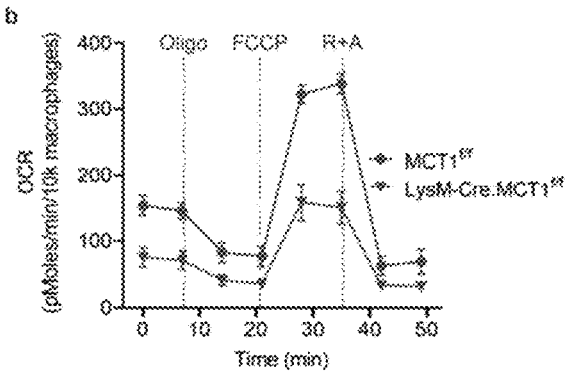
FIG. 10A    FIG. 10B
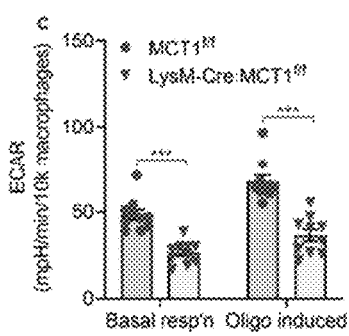
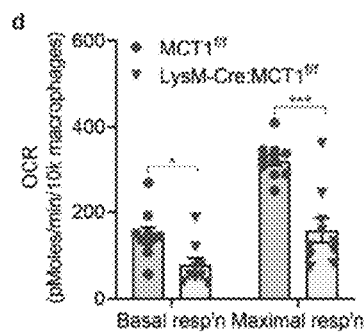
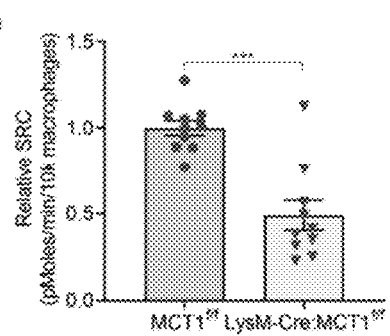
FIG. 10C    FIG. 10D    FIG. 10E
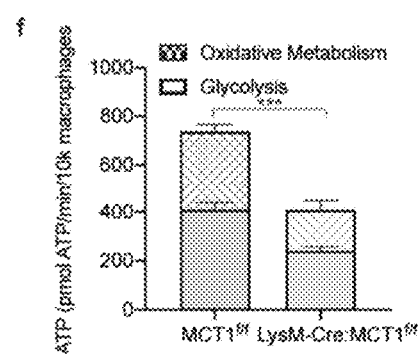
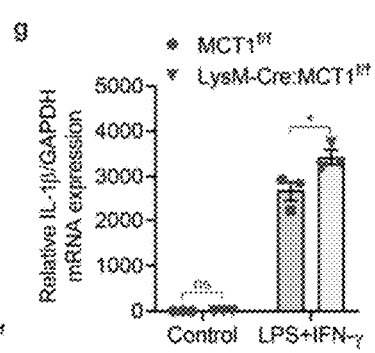
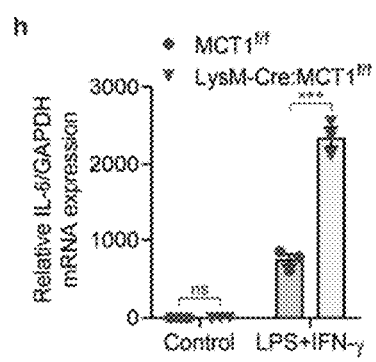
FIG. 10F    FIG. 10G    FIG. 10H

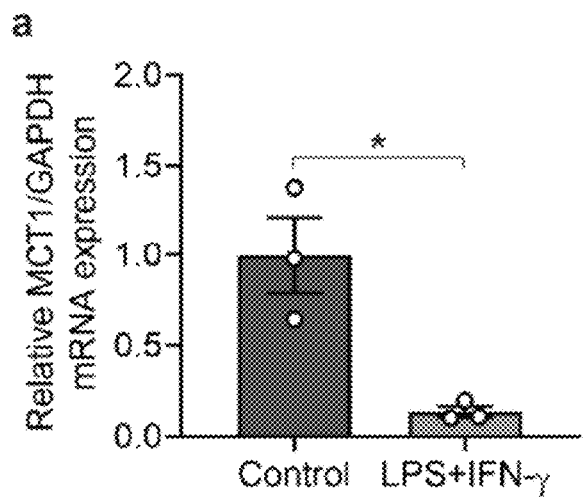
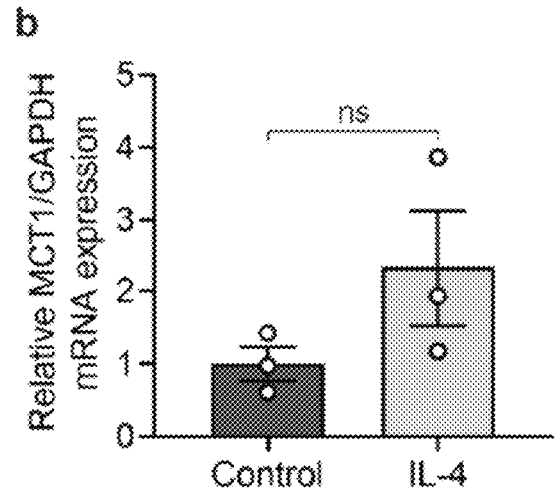
FIG. 11A  FIG. 11B
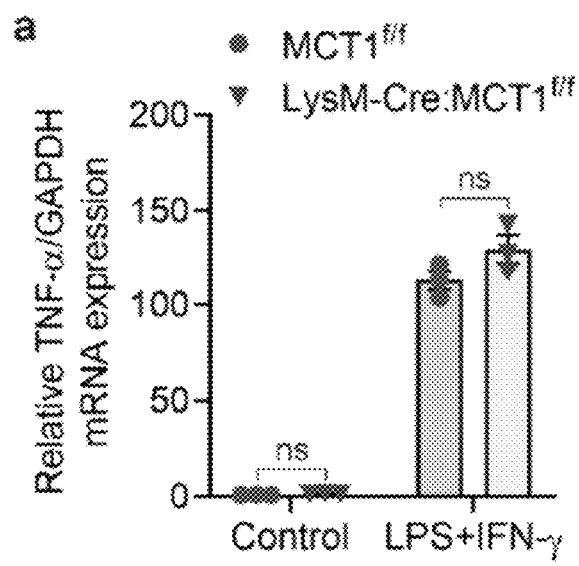
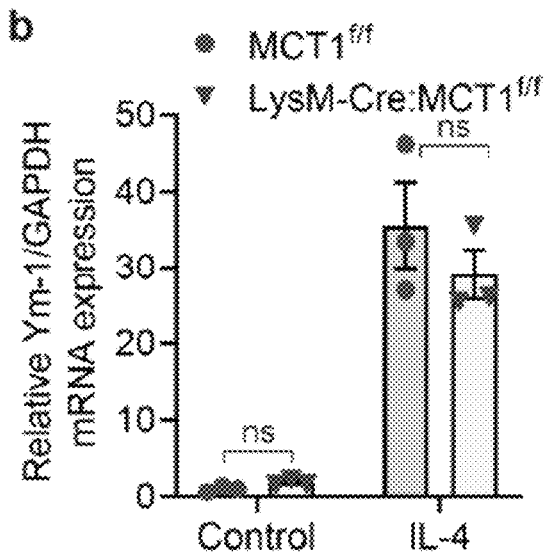
FIG. 12A  FIG. 12B

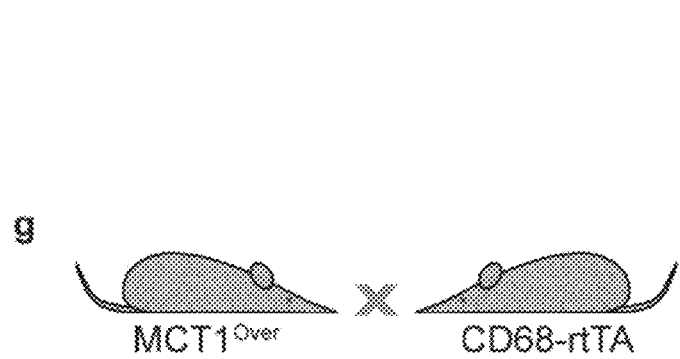
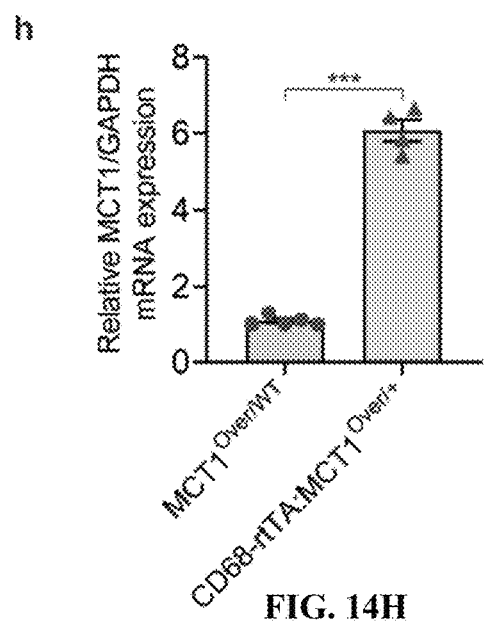
FIG. 14G
FIG. 14H
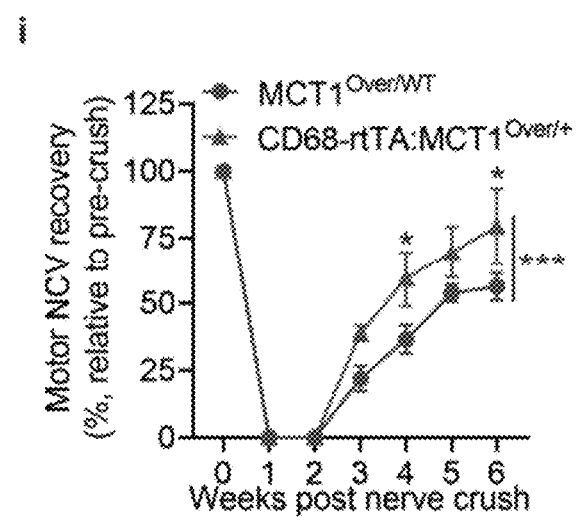
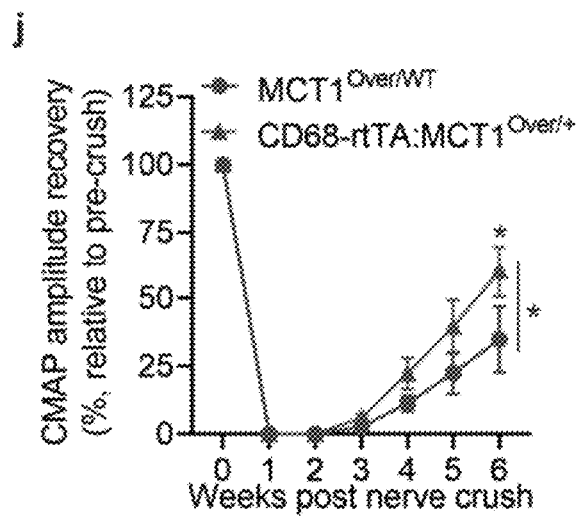
FIG. 14I
FIG. 14J

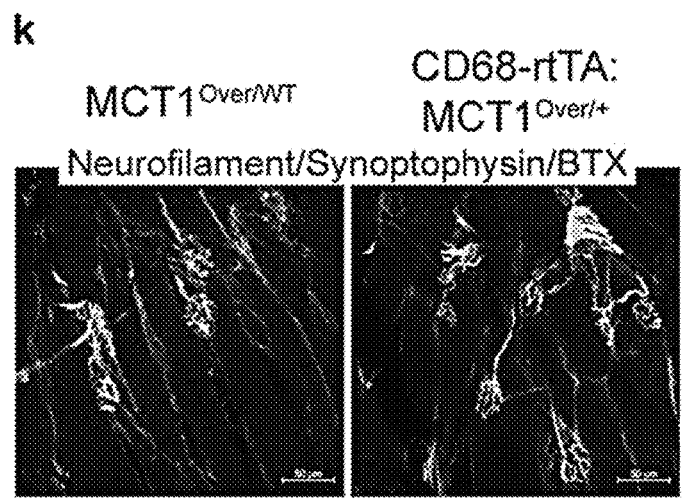
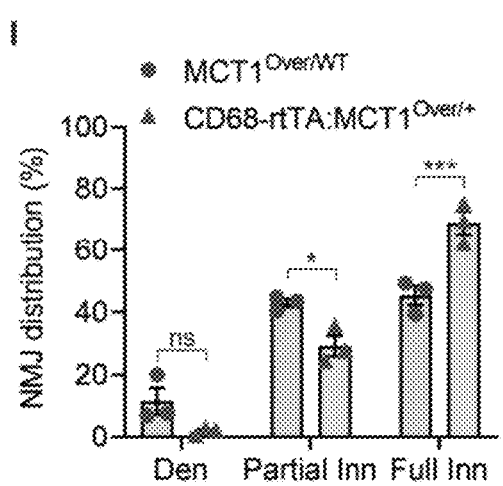
FIG. 14K
FIG. 14L

METHOD FOR ACCELERATING NERVE REGENERATION

CROSS-REFERENCE TO RELATED APPLICATIONS

This application claims benefit of priority under 35 U.S.C. § 119(e) of U.S. Ser. No. 63/072,817, filed Aug. 31, 2020, the entire contents of which is incorporated herein by reference in its entirety.

STATEMENT REGARDING FEDERALLY SPONSORED RESEARCH OR DEVELOPMENT

This invention was made with government support under NS086818 awarded by the National Institutes of Health. The government has certain rights in the invention.

BACKGROUND OF THE INVENTION

Field of the Invention

The present invention relates generally to nerve regeneration and more specifically to modifying MCT1 gene expression in macrophages and their use to accelerate nerve regeneration.

Background Information

Recovery from peripheral nerve injury, which can occur from trauma, surgical iatrogenesis, medication, or toxins, depends on a carefully orchestrated series of events within injured axons and non-neuronal cells, particularly Schwann cells (SCs) and macrophages. In the peripheral nerve distal to the site of injury, SCs release their myelin, de-differentiate, proliferate, and secrete factors to recruit inflammatory cells, axons degenerate due to multiple factors, including energy failure and reduced neurotrophic support, and circulating neutrophils and macrophages are recruited, along with resident macrophages, to phagocytose axonal and myelin debris, which assists axonal regeneration and remyelination. Though the peripheral nervous system is capable of regenerating following injury, the speed of regeneration is quite slow with a rate of approximately 5 mm/day in mice, and possibly even slower in humans. Given that human peripheral nerves are up to 1 meter long, some nerve injuries require regeneration over long distances and incomplete recover occurs due to the loss of regeneration-promoting signals prior to the nerve reaching its destination. Infiltrating and resident macrophages are critical contributors to axonal regeneration by removing inhibitory myelin and axonal debris, adopting a pro-regenerative phenotype, secreting cytokines and growth factors that impact SC function and nerve regeneration, and potentially providing metabolic support to axons. Although the contribution of macrophages to clearance of myelin debris in Wallerian degeneration has been universally acknowledged and accepted, their role in positively influencing the regeneration processes has been recognized only more recently.

Macrophages are abundant not only during nerve degeneration, but also while the nerves are regenerating. Macrophages secrete cytokines that trigger growth factor synthesis in non-neuronal cells in the nerve and produce factors that facilitate SC migration and axon regeneration. The capacity of macrophages to adopt proinflammatory (M1-like) or pro-regenerative (M2-like) states creates a favorable microenvironment for both the initial rapid infiltration of the nerve, where M1-like macrophages predominate, and the subsequent Wallerian degeneration, nerve regeneration and remyelination, when M2-like macrophages predominate. The capacity of macrophages to respond to external stimuli is not uniform, rather it is modulated by cross-talk between intracellular signaling cascades and metabolic pathways, and these pathways govern macrophage phenotype at least partly by altering gene expression that directly modifies cellular metabolism. Besides intracellular metabolic adaptation, macrophages can also impact metabolism in surrounding SCs and neurons following nerve injury by secreting factors.

Monocarboxylate transporters (MCTs), particularly MCT1 (SLC16a1), are critical for regulating diverse immune cell functions. The role of MCT1 in macrophage immune and metabolic functions and their contributions to nerve injury and regeneration biology in unknown. Macrophage phenotype and function have recently been shown to be dependent on their intracellular metabolism. There is an unmet need for elucidating the contribution of MCTs to macrophage metabolism, phenotype, and function, specifically in regard to phagocytosis and supporting peripheral nerve regeneration which can impact how peripheral nerve regeneration is cared for, and ameliorate recovery from nerve injuries. Specifically, there is an unmet need for treatments for accelerating peripheral nerve regeneration.

SUMMARY OF THE INVENTION

The present invention is based on the seminal discovery that upregulating the expression of an MCT1 gene in a macrophage increases nerve regeneration activity of the macrophage. Such macrophages having increased MCT1 gene expression can be administered to a subject having an injured nerve to induce nerve regeneration.

In one embodiment, the present invention provides a method of increasing a macrophage nerve regeneration activity including upregulating expression of an MCT1 gene in the macrophage. In one aspect, upregulating the expression of the MCT1 gene includes contacting the macrophage with a vector encoding an MCT1 gene or with a small molecule agonist of MCT1. In another aspect, the vector is a plasmid or a viral vector. In some aspects, the viral vector is a lentiviral vector. In one aspect, the macrophage nerve regeneration activity is selected from the group consisting of macrophage glycolytic and mitochondrial activities, phagocytosis activity, production of pro-regenerative cytokines, production of pro-inflammatory cytokines, modulation of nerve conduction velocity (NCV), modulation of compound muscle action potential (CMAP), modulation of neuromuscular junction (NMJ) reinnervation, and combinations thereof. In some aspects, the glycolytic and mitochondrial activity is selected from lactate uptake, extracellular acidification rate (ECAR), oxygen consumption rate (OCR), spared respiratory capacity (SRC) and/or ATP production. In other aspects, phagocytosis activity comprises axonal phagocytosis and myelin debris phagocytosis. In some aspects, the pro-regenerative cytokines are selected from the group consisting of IL-10, IL-21R, and TGF-β. In other aspects, the pro-inflammatory cytokines are selected from the group consisting of IL-1β, TNF-α, IL-6, IL-12, IL-15 and IL-23.

In another embodiment, the invention provides a method of inducing nerve regeneration of an injured nerve in a subject including: administering to the subject a macrophage composition, wherein the macrophage composition includes a macrophage having increased nerve regenerating activity as compared to a reference macrophage; and a pharmaceutically acceptable carrier. In one aspect, the macrophage composition is produced by: isolating a macrophage from the subject; and contacting the macrophage with a vector including a polynucleotide encoding MCT1 or with a small molecule agonist of MCT1 to produce a macrophage having increased nerve regenerating activity. In some aspects, the reference macrophage is a macrophage that has not been contacted with a vector including a polynucleotide encoding MCT1 or a small molecule agonist of MCT1. In some aspects, the macrophage is from a blood or bone marrow sample. In another aspect, the macrophage is an anti-inflammatory, pro-regenerative M2-macrophage. In one aspect, the macrophage has increased glycolytic and mitochondrial functions as compared to a reference macrophage that does not have an increased MCT1 gene expression. In another aspect, the macrophage has an increased phagocytosis function as compared to a reference macrophage that does not have an increased MCT1 gene expression. In other aspects, the increased phagocytosis function induces an increase in myelin thickness of a regenerated nerve, an increase in a number of myelinated axons in the regenerated nerve, and a decrease in a g ratio of the regenerated nerve. In one aspect, the macrophage has an increased production of pro-regenerative cytokines as compared to a reference macrophage that does not have an increased MCT1 gene expression. In another aspect, the macrophage has a decreased production of pro-inflammatory cytokines as compared to a reference macrophage that does not have an increased MCT1 gene expression. In one aspect, the injured nerve results from a trauma, inflammation, non-traumatic injury, or exposure to a toxin. In some aspects, the injured nerve results from Parsonage Turner syndrome, a nerve tumor, an auto-immune neuropathy, diabetes, or a toxic neuropathy. In another aspect, inducing nerve regeneration in the subject includes increasing neuroimmune interaction at a nerve injury site. In one aspect, inducing nerve regeneration in the subject comprises increasing nerve conduction velocity (NCV) after a nerve injury. In another aspect, inducing nerve regeneration in the subject comprises increasing compound muscle action potential (CMAP) after a nerve injury. In one aspect, inducing nerve regeneration in the subject comprises increasing neuromuscular junction (NMJ) reinnervation after a nerve injury. In some aspects, increasing neuromuscular junction reinnervation after nerve injury comprises increasing an amount of full NMJ reinnervation and decreasing an amount of denervated or partially reinnervated NMJ in an injured muscle. In another aspect, inducing nerve regeneration in the subject comprises accelerating nerve regeneration in the subject after a nerve injury. In one aspect, administering a macrophage composition comprises intravenous, intraperitoneal and intraarterial administrations. In another aspect, administering a macrophage composition comprises administering the composition in close proximity to the injured nerve.

In an additional embodiment, the invention provides a vector including a polynucleotide encoding MCT1 operably linked to a regulatory sequence. In one aspect, the vector is a plasmid or a viral vector. In some aspects, the viral vector is a lentiviral vector, an adenoviral vector or an adeno-associated viral (AAV) vector.

In a further embodiment, the invention provides an isolated macrophage including a vector including a polynucleotide encoding MCT1 operably linked to a regulatory sequence.

In yet another embodiment, the present invention provides a macrophage cell composition including an isolated macrophage including a vector including a polynucleotide encoding MCT1 operably linked to a regulatory sequence, and a pharmaceutically acceptable carrier.

BRIEF DESCRIPTION OF THE DRAWINGS

FIGS. 1A-1R illustrate the selective ablation of MCT1 in macrophages and its role in axon regeneration. FIG. 1A illustrates the breeding of MCT1$^{f/f}$ mice with transgenic mice with Cre recombinase driven by LysM (LysM-Cre) to generate macrophage-specific MCT1 knockout mice; LysM-Cre:MCT1$^{f/f}$, and littermate control mice; MCT1$^{f/f}$. FIG. 1B is a schematic representation of the site of sciatic nerve crush and setup of electrodes for electrophysiological stimulations and recordings. FIG. 1C is a graph illustrating motor nerve conduction velocity (NCV) of nerve after injury. Mean±SEM, n=13 (for MCT1$^{f/f}$ group) or 11 (for LysM-Cre:MCT 1$^{f/f}$ group), *p<0.05, **p<0.0001. FIG. 1D is a graph illustrating compound muscle action potential (CMAP) amplitude recovery of nerve after injury. Mean±SEM, n=13 (for MCT1$^{f/f}$ group) or 11 (for LysM-Cre:MCT1$^{f/f}$ group), p<0.01. FIG. 1E illustrates representative photomicrographs of fluorescently labelled neuromuscular junctions (NMJs) in gastrocnemius muscles 3 weeks after crush. Calibration bar: 100 μm. FIG. 1F is a bar graph illustrating the percentage of fully reinnervated, partially reinnervated, and denervated AChR clusters 3 weeks after crush. Den, Denervated AChR clusters; Partial Inn, partially reinnervated AChR clusters; Full Inn, fully reinnervated AChR clusters. Mean±SEM, n=3-4 per group, ns=not significant. FIG. 1N illustrates representative photomicrographs of sural nerve 6 weeks after sciatic nerve crush. Calibration bar: 20 μm. FIG. 1O illustrates scatter plot graph displaying g ratio (y-axis) in relation to axon diameter (x-axis) of individual fiber of sural nerve 6 weeks after sciatic nerve crush. FIG. 1P is a bar graph illustrating g ratio of sural nerve 6 weeks after sciatic nerve crush. Mean±SEM, n=3-4 per group, **p<0.01. FIG. 1Q is a bar graph illustrating myelinated axon diameter of sural nerve 6 weeks after sciatic nerve crush. Mean±SEM, n=3-4 per group, ns=not significant. FIG. 1R is a bar graph illustrating myelinated axon count of sural nerve 6 weeks after sciatic nerve crush. Mean±SEM, n=3-4 per group, ns=not significant.

FIGS. 2A-2F illustrate the selective ablation of MCT1 in Schwann cells, DRG neurons, or perineurial cells. FIG. 2A illustrates the breeding of MCT1$^{f/f}$ mice with transgenic mice with Cre recombinase driven by P0-Cre, to generate Schwann cell-specific MCT1 knockout mice and littermate control mice and a graph illustrating motor nerve conduction velocity (NCV) of nerve after injury. FIG. 2B illustrates compound muscle action potential (CMAP) amplitude recovery of nerve after injury. FIG. 2C illustrates the breeding of MCT1$^{f/f}$ mice with transgenic mice with Cre recombinase driven by Adv-Cre, to generate DRG neuron-specific MCT1 knockout mice and littermate control mice and a graph illustrating motor NCV of nerve after injury. FIG. 2D illustrates CMAP amplitude recovery of nerve after injury. FIG. 2E illustrates the breeding of MCT1$^{f/f}$ mice with transgenic mice with Cre recombinase driven by Gli1-Cre, to generate perineurial cell-specific MCT1 knockout mice and littermate control mice and a graph illustrating motor NCV of nerve after injury. FIG. 2F illustrates CMAP amplitude recovery of nerve after injury. Mean±SEM, n=6-10 per group.

FIGS. 3A-3F illustrate the validation of macrophage-specific MCT1 deficient mice. FIG. 3A is a bar graph illustrating the expression of monocarboxylate transporter MCT1 mRNA in peritoneal exudate macrophage cultures. FIG. 3B is a bar graph illustrating lactate uptake and blockade by selective MCT1 inhibitor in peritoneal exudate macrophage cultures. FIG. 3C is a bar graph illustrating the expression of monocarboxylate transporter MCT2 mRNA in peritoneal exudate macrophage cultures. FIG. 3D is a bar graph illustrating the expression of monocarboxylate transporter MCT4 mRNA in peritoneal exudate macrophage cultures. FIG. 3E is a bar graph illustrating the expression of glucose transporter GLUT1 mRNA in peritoneal exudate macrophage cultures. FIG. 3F is a bar graph illustrating the expression of glucose transporter GLUT3 mRNA in peritoneal exudate macrophage cultures. Mean±SEM, n=5-9 per group or n=4-5 per group, *p<0.05, p<0.01 *p<0.001; ns=not significant.

FIG. 4A illustrates protein level of MCT1 in sciatic nerves assessed by Western blot analysis. FIG. 4B is a bar graph illustrating the quantification of MCT1 by densitometry using β-actin as a loading control. Mean±SEM, n=3 per group, **p<0.01. FIG. 4C shows representative immunofluorescent images of Gli1-Cre:RosaYFP nerve image labelled with Claudin1. Complete nerve image (left panel); high magnification (right panel). Images are representative confocal micrographs of at least three independent experiments. Calibration bar: 20 μm. FIG. 4D shows representative immunofluorescent images of MCT1 immunoreactivity and Claudin1 in sciatic nerves from MCT1$^{f/f}$ and LysM-Cre:MCT1$^{f/f}$ mice. Complete nerve images (left panel) are presented in high magnification in right panel. Images are representative confocal micrographs of at least three independent experiments. Calibration bars: 50 μm for left panel and 10 μm for right panel.

FIG. 5A shows representative immunofluorescent images of MCT1 immunoreactivity in Adv-Cre:MCT 1$^{f/f}$. Images are representative confocal micrographs of at least three independent experiments. Calibration bar: 20 μm. FIG. 5B is a bar graph illustrating the expression of monocarboxylate transporter MCT1 in DRGs. FIG. 5C is a bar graph illustrating the expression of monocarboxylate transporter MCT2 in DRGs. FIG. 5D is a bar graph illustrating the expression of monocarboxylate transporter MCT4 in DRGs. Mean±SEM, n=3-4 per group, **p<0.01; ns=not significant.

FIG. 6A is a graph illustrating motor nerve conduction velocity (NCV) recovery of nerve after injury. FIG. 6B is a graph illustrating compound muscle action potential (CMAP) amplitude recovery of nerve after injury. Recoveries are presented as percent relative to pre-crush conditions. Mean±SEM, n=4 (for MCT1$^{f/f}$ group) or 6 (for LysM-Cre:MCT1$^{f/f}$ group), *p<0.05, p<0.01, **p<0.0001.

FIGS. 7A-7H illustrate macrophages function in the context of MCT1 deficiency. FIG. 7A shows representative immunofluorescent images illustrating the number of Iba1-positive macrophages infiltrating into crushed or uncrushed nerves (7 days post-crush). FIG. 7B is a bar graph illustrating the quantification of the total number of Iba1-positive macrophages infiltrating into crushed or uncrushed nerves. Mean±SEM, n=4-7 per group, ns=not significant. Calibration bar: 50 μm. FIG. 7C is a bar graph illustrating the mRNA expression of IL-1β at 1-day post crush. FIG. 7D is a bar graph illustrating the mRNA expression of TNF-α at 1-day post crush. FIG. 7E is a bar graph illustrating the mRNA expression of IL-1β at 3-day post crush. FIG. 7F is a bar graph illustrating the mRNA expression of Ym-1 at 3-day post crush. FIG. 7G is a bar graph illustrating the mRNA expression of Ym-1 at 10-day post crush. FIG. 7H is a bar graph illustrating the mRNA expression of Arg-1 at 10-day post crush. mRNA levels evaluated post crush in uncrushed and crushed sciatic nerves (distal to site of injury) by real-time RT-PCR. Mean±SEM, n=3-9 per group, *p<0.05; p<0.01; *p<0.001; ns=not significant.

FIGS. 9A-9C illustrate the impact of MCT1 deficiency in macrophages on inflammatory cytokine expression in injured sciatic nerves. FIG. 9A is a bar graph illustrating the mRNA expression of TNF-α at 3 days post crush. FIG. 9B is a bar graph illustrating the mRNA expression of Arg-1 at 3 days post crush. FIG. 9C is a bar graph illustrating the mRNA expression of IL-1β at 10 days post crush. mRNA levels were evaluated post crush in uncrushed and crushed sciatic nerves (distal to site of injury) by real-time RT-PCR. Mean±SEM, n=4-8 per group, ns=not significant.

FIGS. 10A-10K illustrate the effect of MCT1 ablation on metabolic functions, expression of inflammatory cytokines, and phagocytic activity of macrophages in vitro. FIG. 10A illustrates real-time extracellular acidification (ECAR) in peritoneal exudate macrophages.

FIG. 10B illustrates oxygen consumption in peritoneal exudate macrophages. FIG. 10C is a bar graph illustrating the ECAR of macrophages during basal condition and following oligomycin treatment. ***p<0.001. FIG. 10D is a bar graph illustrating the OCR of macrophages during basal respiration and FCCP-induced maximal respiration. *p<0.05; *p<0.001. FIG. 10E is a bar graph illustrating spare respiratory capacity (SRC) of macrophages. *p<0.001. FIG. 10F is a bar graph illustrating total ATP generated by oxidative metabolism and glycolysis in macrophages. Mean±SEM, n=10 per group. ***p<0.001. ECAR, extracellular acidification rate; FCCP, carbonyl cyanide-4 (trifluoromethoxy) phenylhydrazone; OCR, oxygen consumption rate; Oligo, oligomycin; R+A; Rotenone and Antimycin. FIG. 10G is a bar graph illustrating mRNA levels of M1-related genes IL-1β assessed by real-time RT-PCR in peritoneal exudate macrophage cultures treated with LPS (100 ng/ml) plus IFN-γ (50 U/ml) for 3 hours. FIG.

10H is a bar graph illustrating mRNA levels of M1-related genes IL-6 assessed by real-time RT-PCR in peritoneal exudate macrophage treated with LPS (100 ng/ml) plus IFN-γ (50 U/ml) for 3 hours. FIG. 10I is a bar graph illustrating mRNA levels of Arg-1 assessed by real-time RT-PCR in peritoneal exudate macrophages treated with IL-4 (10 ng/ml) for 3 hours. Mean±SEM, n=3 per group, *p<0.05; ***p<0.001; ns=not significant, two-way ANOVA with Bonferroni's multiple comparisons test. FIG. 10J shows representative images of peritoneal exudate macrophages incubated with fluorescent microspheres for 2 hours. Representative images from at least five independent experiments. FIG. 10K is a bar graph illustrating the quantification of the number of cells with internalized fluorescent microspheres presented as a percentage. Mean±SEM, n=5-7 per group, *p<0.05; unpaired t test. Calibration bar: 50 µm.

FIGS. 11A-11B illustrate the expression of MCT1 in M1 and M2 phenotypes of macrophages. FIG. 11A is a bar graph illustrating MCT1 mRNA expression assessed by real-time RT-PCR in peritoneal exudate macrophage cultures treated with LPS (100 ng/ml) plus IFN-γ (50 U/ml) for 3 h. FIG. 11B is a bar graph illustrating MCT1 mRNA expression assessed by real-time RT-PCR in peritoneal exudate macrophage cultures treated with IL-4 (10 ng/ml) for 3 h. Mean±SEM, n=3 per group, *p<0.05; ns=not significant.

FIGS. 12A-12B illustrate the impact of MCT1 ablation expression of inflammatory cytokines on macrophages. FIG. 12A is a bar graph illustrating mRNA levels of TNF-α assessed by real-time RT-PCR in peritoneal exudate macrophage cultures treated with LPS (100 ng/ml) plus IFN-γ (50 U/ml) for 3 h. FIG. 12B is a bar graph illustrating mRNA levels of Ym-1 assessed by real-time RT-PCR in peritoneal exudate macrophage cultures treated with IL-4 (10 ng/ml) for 3 h. Mean±SEM, n=3 per group, ns=not significant.

FIG. 13A is a schematic representation of the experimental procedure. FIG. 13B shows representative immunofluorescent images of the localization of bone marrow-derived macrophages (BMDMs) in injured and uninjured sciatic nerve 3 days post crush. FIG. 13C shows representative immunofluorescent images of F4/80 expressing BMDMs in injured sciatic nerve 7 days following tail vein injection. Images are representative confocal micrographs of three independent experiments. Calibration bar: 20 µm. FIG. 13D is a schematic representation of the experimental procedure. FIG. 13E is a bar graph illustrating motor nerve conduction velocity (NCV) recovery of nerve after injury. FIG. 13F is a bar graph illustrating compound muscle action potential (CMAP) amplitude recovery of nerve after injury. Recoveries are presented as percent relative to pre-crush conditions. Mean±SEM, n=4 per group, *p<0.05, p<0.01, *p<0.001.

FIGS. 14A-14L illustrate the effect of the selective overexpression of MCT1 in macrophages on the regeneration of injured peripheral nerves. FIG. 14A illustrated the breeding of LysM-Cre mice with lox-stop-lox tTA mice and a tet-responsive MCT1 overexpressor mouse to generate transgenic mice with upregulation of MCT1 selectively in macrophages (LysM-Cre:tTA$^{+/-}$:MCT1$^{Over/+}$). FIG. 14B is a bar graph illustrating the expression of MCT1 mRNA in peritoneal exudate macrophage cultures assessed by real-time RT-PC. Mean±SEM, n=3-8 per group, ***p<0.001. FIG. 14C is a graph illustrating motor nerve conduction velocity (NCV) recovery of nerve after injury. FIG. 14D is a graph illustrating compound muscle action potential (CMAP) amplitude recovery of nerve after injury. Mean±SEM, n=8 (for MCT1$^{Over/WT}$ group) or 6 (for LysM-Cre:tTA$^{+/-}$:MCT1$^{Over/WT}$ group), *p<0.05, p<0.01, *p<0.001. FIG. 14E shows representative immunofluorescent images illustrating labelled neuromuscular junctions (NMJs) in gastrocnemius muscles 6 weeks after crush. Calibration bar: 50 µm. FIG. 14F is a bar graph illustrating AChR clusters in mice with macrophage-specific MCT1 overexpression. Mean±SEM, n=3-4 per group, *p<0.05; ns=not significant. FIG. 14G is a schematic representation of the breeding of CD68-rtTa mice with MCT1$^{Over}$ to generate transgenic mice with macrophage specific, doxycycline-inducible MCT1 expression, (CD68-rtTA:MCT1$^{Over/+}$). FIG. 14H is a bar graph illustrating the expression of MCT1 mRNA in peritoneal exudate macrophage cultures assessed by real-time RT-PCR. Mean±SEM, n=4-5 per group, ***p<0.001. FIG. 14I is a graph illustrating motor nerve conduction velocity (NCV) recovery of nerve before and after injury. FIG. 14J is a graph illustrating CMAP amplitude recovery of nerve before and after injury. Mean±SEM, n=9 (for MCT1$^{Over/WT}$ group) or 5 (for CD68-rtTA:MCT1Over/+ group), *p<0.05, ***p<0.001. FIG. 14K shows representative immunofluorescent images illustrating fluorescently labelled NMJs in gastrocnemius muscles 6 weeks after crush. Calibration bar: 50 µm. FIG. 14L is a bar graph illustrating AChR clusters in mice with macrophage-specific MCT1 overexpression 6 weeks after crush. Den, Denervated AChR clusters; Partial Inn, partially reinnervated AChR clusters; Full Inn, fully reinnervated AChR clusters. Mean±SEM, n=3 per group, *p<0.05, ***p<0.001; ns=not significant.

DETAILED DESCRIPTION OF THE INVENTION

Figure 1G:
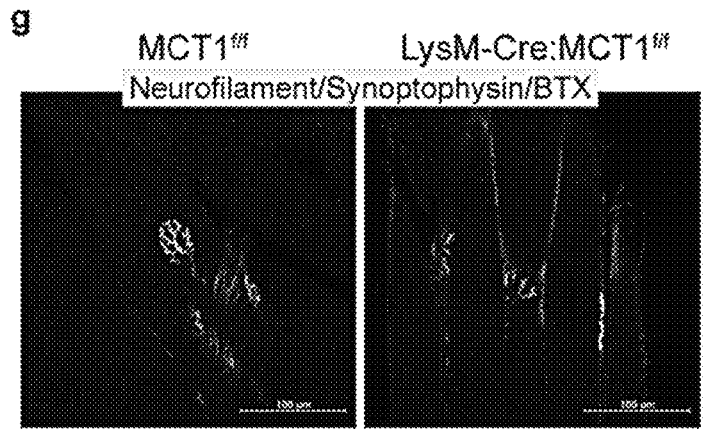
FIG. 1G representative photomicrographs of fluorescently labelled NMJs in gastrocnemius muscles 6 weeks after crush. Calibration bar: 100 μm.
Figure 1H:
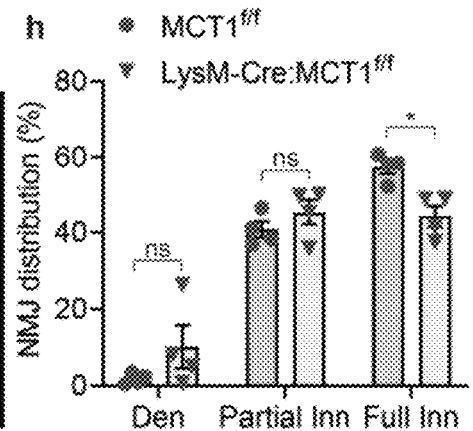
FIG. 1H is a bar graph illustrating the percentage of fully reinnervated, partially reinnervated, and denervated AChR clusters 6 weeks after crush. Den, Denervated AChR clusters; Partial Inn, partially reinnervated AChR clusters; Full Inn, fully reinnervated AChR clusters. Mean±SEM, n=3-4 per group, *p<0.05; ns=not significant.
Figure 1I:
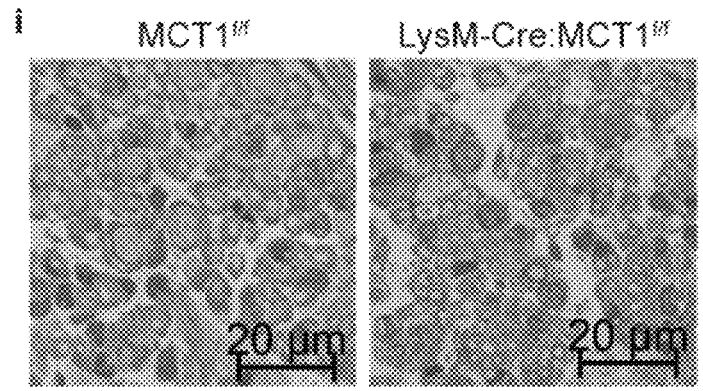
FIG. 1I illustrates representative photomicrographs of sural nerve 3 weeks after sciatic nerve crush. Calibration bar: 20 μm.
Figure 1J:
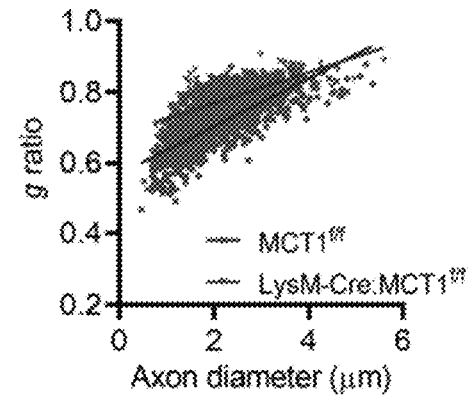
FIG. 1J illustrates scatter plot graph displaying g ratio (y-axis) in relation to axon diameter (x-axis) of individual fiber of sural nerve 3 weeks after sciatic nerve crush.
Figure 1K:
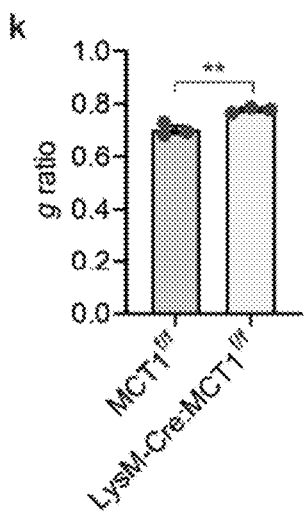
FIG. 1K is a bar graph illustrating g ratio of sural nerve 3 weeks after sciatic nerve crush. Mean±SEM, n=3-4 per group, **p<0.01.

The present invention is based on the seminal discovery that upregulating the expression of an MCT1 gene in a macrophage increases the nerve regeneration activity of the macrophage. Such macrophages having increased MCT1 gene expression can be administered to a subject having an injured nerve to induce nerve regeneration.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

In one embodiment, the present invention provides a method of increasing macrophage nerve regeneration activity including upregulating an expression of an MCT1 gene in the macrophage.

Macrophages are white blood cells of the immune system specialized in phagocytosis found in essentially all tissues, where they patrol for potential pathogens by amoeboid movement. They take various forms and various names throughout the body (e.g., histiocytes, Kupffer cells, alveolar macrophages, microglia, and others), but all are part of the mononuclear phagocyte system. Macrophages are phagocytes and are highly specialized in removal of dying or dead cells and cellular debris; which render them critical during chronic inflammation. Neutrophils are first attracted to a site of inflammation, where they perform their function and die, before being phagocytized by macrophages. The removal of dying cells is, to a greater extent, handled by fixed macrophages, which will stay at strategic locations such as the lungs, liver, neural tissue, bone, spleen and connective tissue, ingesting foreign materials such as pathogens and recruiting additional macrophages if needed.

There are two macrophage subtypes designated M1 and M2, which have different metabolism. Macrophages that encourage inflammation are called M1 macrophages, whereas those that decrease inflammation and encourage tissue repair are called M2 macrophages. Pro-regenerative macrophages are well known for their role in promoting tissue repair; however, their specific roles in promoting regeneration of the injured nerve are not well defined. After injury, macrophages function to clear debris and persist within the nerve microenvironment where they regulate Schwann cell function during nerve regeneration and remyelination. In Human, peripheral nerves regrow at a very slow rate and only over the first 1-2 years, preventing proximal nerve injuries from recovering. Although depletion of macrophages following peripheral nervous system injury has been shown to impair regeneration and to result in worsened outcomes, the identity and the extent of their contribution to the regenerative process remained unclear.

MCT1 gene, also known as SLC16A1 (accession number NM_003051) encodes a monocarboxylate transporter (MCT), which catalyzes the bidirectional proton-linked transport of short-chain monocarboxylates such as L-lactate, ketone bodies and pyruvate across the plasma membrane of mammalian cells. In humans, there are four MCT lactate transporter, MCT1, MCT2 (or SLC16A7, accession number NM_004731), MCT3 (or SLC16A8, accession number NM_0013356) and MCT4 (or SLC16A3, accession number NM_004207), present in many cells in the body. MCT1 catalyzes the rapid transport across the plasma membrane of many monocarboxylates such as lactate, pyruvate, branched-chain oxo acids derived from leucine, valine and isoleucine, and the ketone bodies acetoacetate, beta-hydroxybutyrate and acetate. Depending on the tissue and on circumstances, MCT1 mediates the import or export of lactic acid and ketone bodies, and modulates the cellular levels of lactate and pyruvate, small molecules that contribute to the regulation of central metabolic pathways and insulin secretion, with concomitant effects on plasma insulin levels and blood glucose homeostasis.

The present invention relies on the discovery that the upregulation of an MCT1 gene in macrophages alters numerous cellular functions in macrophages associated with nerve regeneration activity of the macrophage. As used herein, the phrase "increasing a macrophage nerve regeneration activity" refers to the increase, improvement, or induction, of a cellular activity of a macrophage that results in the macrophage being more effective at inducing nerve regeneration. For example, a cellular activity of a macrophage that results in an increased nerve regeneration activity of a macrophage can be induced or promoted by the upregulation of MCT1, resulting in an increase or improvement of the nerve regeneration activity of the macrophage.

The effectiveness of a macrophage to induce nerve regeneration can include induction of nerve regeneration, the increase in nerve regeneration, or the acceleration of the process of nerve regeneration. There are numerous cellular macrophage activities that can impact a macrophage ability to induce nerve regeneration. Non-limiting examples of macrophage nerve regeneration activities include macrophage glycolytic and mitochondrial activities, phagocytosis activity, production of pro-regenerative cytokines, production of pro-inflammatory cytokines, modulation of nerve conduction velocity (NCV), modulation of compound muscle action potential (CMAP), modulation of neuromuscular junction (NMJ) reinnervation, and combinations thereof.

As used herein, the phrase "upregulating the expression of MCT1 gene" is meant to include any means that can result in increased expression of an MCT1 gene, including using gene therapy, protein therapy, or using small molecules. For example, genetically modified cell therapy, which relies on the incorporation of a nucleic acid molecule (e.g., a gene) in a cell to provides expression of the protein encoded by the gene can be used to induce transient expression of an MCT1 gene, stable expression of an MCT1 gene, or transient or stable expression of another MCT gene such as MCT2, MCT3 or MCT4 in a macrophage. Any means known in the art to incorporate nucleic acid molecule into a cell can be used to incorporate an MCT1 gene in a macrophage. Protein therapy, which relies on the introduction of a polypeptide (e.g., a protein) in a cell can be used directly to increase the level of an MCT1 protein or another MCT protein such as MCT2, MCT3, or MCT4 in a macrophage.

MCT1 gene expression can also be increased using small molecule agents. As used herein the term "small molecules" refers to any low molecular weight organic or inorganic compound that may regulate a biological process. Small molecules are capable of binding specific biological macromolecules and act as an effector, altering the activity or function of the target. These compounds can be natural or artificial (such as drugs). Non-limiting examples of small molecules that can be used to increase MCT1 gene expression include small molecules that increase MCT1 gene expression, MCT1 agonists, and small molecules that inhibit an MCT1 antagonist.

In one aspect, upregulating the expression of the MCT1 gene includes contacting the macrophage with a vector encoding an MCT1 protein or with a small molecule agonist of MCT1.

A nucleic acid molecule including a gene of interest, such as an MCT1 gene encoding an MCT protein can be incorporated into an expression cassette (e.g., a circular or linear polynucleotide including one or more genes or interest operably linked to one or more regulatory sequences) to be delivered to a cell in a vector. A vector can be an integrating or non-integrating vector, referring to the ability of the vector to integrate the expression cassette into a genome of a cell. Integrating vector and non-integrating vector can be used to deliver an expression cassette containing a gene operably linked to a regulatory element into a cell, to induce the expression of the recombinant nucleic acid construct. Regulatory elements can include promoter, protein tags, functional domains, regulatory sequences and the like. Examples of vectors include, but are not limited to, (a) non-viral vectors such as nucleic acid vectors including linear oligonucleotides and circular plasmids; and (b) viral vectors such as retroviral vectors, lentiviral vectors, adenoviral vectors, and AAV vectors. Viruses have several advantages for delivery of nucleic acids, including high infectivity and/or tropism for certain target cells or tissues. In a specific embodiment, the protein of the present invention includes MCT1. In another aspect, the vector is a plasmid or a viral vector. In some aspects, the viral vector is a lentiviral vector, an adenovirus vector or an AAV vector.

As used herein, macrophage "glycolytic and mitochondrial activities" refer to any activity that reflects how the glycolysis pathway and mitochondrial respiration occur in the macrophage. Glycolysis is the metabolic pathway that converts glucose, into pyruvate, and releases energy in the forms of the high-energy molecules ATP (adenosine triphosphate) and NADH (reduced nicotinamide adenine dinucleotide) in the process. Glycolysis is a sequence of ten enzyme-catalyzed reactions. Most monosaccharides, such as fructose and galactose, can be converted to one of these intermediates. The intermediates may also be directly useful rather than just utilized as steps in the overall reaction. For example, the intermediate dihydroxyacetone phosphate (DHAP) is a source of the glycerol that combines with fatty acids to form fat. Cellular respiration, or mitochondrial respiration, is a set of metabolic reactions and processes that take place in the mitochondria of cells to convert chemical energy from oxygen molecules or nutrients into adenosine triphosphate (ATP), and then release waste products. The reactions involved in respiration are catabolic reactions, which break large molecules into smaller ones, releasing energy because weak high-energy bonds, in particular in molecular oxygen, are replaced by stronger bonds in the products. Respiration is one of the key ways a cell releases chemical energy to fuel cellular activity. The overall reaction occurs in a series of biochemical steps, some of which are redox reactions. Although cellular respiration is technically a combustion reaction, it clearly does not resemble one when it occurs in a living cell because of the slow, controlled release of energy from the series of reactions.

Glycolysis and mitochondrial rely on transforming a subtract into a product, there are multiple well-known ways to measure and evaluate glycolysis and mitochondrial activity in a cell. In some aspects, the glycolytic and mitochondrial activity assessed to evaluate a macrophage nerve regeneration activity is selected from lactate uptake, extracellular acidification rate (ECAR), oxygen consumption rate (OCR), spared respiratory capacity (SRC) and/or ATP production.

As used herein, macrophage "phagocytosis activity" refers to any activity that reflects how the process by which a cell uses its plasma membrane to engulf a large particle (≥0.5 μm), giving rise to an internal compartment called the phagosome (e.g., phagocytosis, a type of endocytosis). In a multicellular organism's immune system, phagocytosis is a major mechanism used to remove pathogens and cell debris. The ingested material is then digested in the phagosome. Bacteria, dead tissue cells, and small mineral particles are all examples of objects that may be phagocytized. Phagocytosis is one of the main mechanisms of the innate immune defense. It is one of the first processes responding to infection, and is also one of the initiating branches of an adaptive immune response. Although most cells are capable of phagocytosis, some cell types perform it as part of their main function. Neutrophils, macrophages, monocytes, dendritic cells, osteoclasts and eosinophils can be classified as professional phagocytes, performing phagocytosis as their main function. Monocytes, and the macrophages that mature from them, leave blood circulation to migrate through tissues. There, they are resident cells and form a resting barrier. Macrophages initiate phagocytosis by mannose receptors, scavenger receptors, Fcγ receptors and complement receptors 1, 3 and 4. Macrophages are long-lived and can continue phagocytosis by forming new lysosomes.

There are multiple well-known ways to measure and evaluate phagocytosis activity in a cell (for example detailed in Chow et al., Current Protocols in Cell Biology 2014). In some aspects, the phagocytosis activity assessed to evaluate a macrophage nerve regeneration activity refers to the ability of a macrophage to clear Wallerian degeneration debris; which can be evaluated by assessing axonal phagocytosis or myelin debris phagocytosis.

As used herein, macrophage "production of cytokine" refers to both the type and the amount of cytokines produced by a macrophage. Cytokines are a broad and loose category of small proteins (~5-20 kDa) important in cell signaling, by being involved in autocrine, paracrine and endocrine signaling as immunomodulating agents. The term "cytokine" includes chemokines, interferons, interleukins, lymphokines, and tumor necrosis factors. Cytokines are produced by a broad range of cells, including immune cells like macrophages, B lymphocytes, T lymphocytes and mast cells, as well as endothelial cells, fibroblasts, and various stromal cells; a given cytokine may be produced by more than one type of cell. They act through cell surface receptors and are especially important in the immune system where they modulate the balance between humoral and cell-based immune responses, and regulate the maturation, growth, and responsiveness of particular cell populations. Some cytokines enhance or inhibit the action of other cytokines in complex ways. Macrophages for examples can secrete various type of cytokines, responsible for different cellular responses. In the context of tissue regeneration, and specifically nerve regeneration, macrophages can produce pro-regenerative cytokines or pro-inflammatory cytokines.

As used herein, a "pro-regenerative cytokine", or "anti-inflammatory cytokine" refers to a cytokine that supports nerve regeneration, which can include a cytokine that supports pro-regenerative macrophage, or a cytokine that inhibits pro-inflammatory responses. Non-limiting examples of anti-inflammatory cytokines include interleukin (IL)-1 receptor antagonist (IL1ra), IL-4, IL-10, IL-11, IL-13 and transforming growth factor-β (TGF-β). In some aspects, the pro-regenerative cytokines are selected from the group consisting of IL-10, IL-21R, and TGF-β.

As used herein, a "pro-inflammatory cytokine", or "inflammatory cytokine" refers to a cytokine that supports inflammation, which can include a cytokine that supports pro-inflammatory macrophage, or a cytokine that inhibits regenerative responses. Non-limiting examples of pro-inflammatory cytokines include: interleukin-1 (IL-1), IL-1β, IL-6, IL-12, IL-15, IL-17, IL-18, IL-23, tumor necrosis factor alpha (TNF-α), interferon gamma (IFNγ), and granulocyte-macrophage colony stimulating factor (GM-CSF). In some aspects, the pro-inflammatory cytokines are selected from the group consisting of IL-1β, TNF-α, IL-6, IL-12, IL-15 and IL-23.

Macrophage nerve regeneration activity can also be evaluated by measuring nerve parameters variation upon exposure to macrophages having an increased MCT1 expression. There are numerous well-known measurement that can be evaluated to assess nerve regeneration; for example nerve conduction velocity (NCV), compound muscle action potential (CMAP), and modulation of neuromuscular junction (NMJ) reinnervation can be measured.

In another embodiment, the invention provides a method of inducing nerve regeneration of an injured nerve in a subject including administering to the subject a macrophage composition, wherein the macrophage composition includes a macrophage having increased nerve regenerating activity as compared to a reference macrophage; and a pharmaceutically acceptable carrier.

The method can be applied to any subject in need thereof, such as a subject having an injured nerve. The term "subject" as used herein refers to any individual or patient to which the subject methods are performed. Generally, the subject is human, although as will be appreciated by those in the art, the subject may be an animal. Thus other animals, including vertebrate such as rodents (including mice, rats, hamsters and guinea pigs), cats, dogs, rabbits, farm animals including cows, horses, goats, sheep, pigs, chickens, etc., and primates (including monkeys, chimpanzees, orangutans and gorillas) are included within the definition of subject.

The term "treatment" is used interchangeably herein with the term "therapeutic method" and refers to therapeutic treatments or measures that cure, slow down, lessen symptoms of, and/or halt progression of a diagnosed pathologic conditions or disorder (e.g., induce or accelerate nerve regeneration).

The terms "therapeutically effective amount", "effective dose," "therapeutically effective dose", "effective amount," or the like refer to that amount of the subject compound that will elicit the biological or medical response of a tissue, system, animal or human that is being sought by the researcher, veterinarian, medical doctor or other clinician. Generally, the response is either amelioration of symptoms in a patient or a desired biological outcome (e.g., nerve regeneration, or acceleration of the nerve regeneration). Such amount should be sufficient to induce, improve or accelerate nerve regeneration in a subject. The effective amount can be determined as described herein.

A macrophage composition includes a macrophage modified to have an increased nerve regenerating activity as compared to a reference macrophage. To increase a nerve regenerating activity of a macrophage, a macrophage is first isolated, and then modified to upregulate its MCT1 gene expression thereby increasing its nerve regenerating activity.

In one aspect, the macrophage composition is produced by: isolating a macrophage from the subject; and contacting the macrophage with a vector including a polynucleotide encoding MCT1 or with a small molecule agonist of MCT1 to produce a macrophage having increased nerve regenerating activity.

As used herein a "reference macrophage" refers to a macrophage that has not been modified to have an increased nerve regeneration activity, which can include a macrophage that has not been modified at all, or a macrophage that has been modified, but the modification does not or fails to increase nerve regeneration activity to the macrophage. As discussed above, there are several ways to measure nerve regeneration activity of a macrophage. In some aspects, the reference macrophage is a macrophage that has not been contacted with a vector including a polynucleotide encoding MCT1 or a small molecule agonist of MCT1. For example, a reference macrophage can include a macrophage that does have an increased MCT1 gene expression.

A "sample" or "biological sample" is meant to refer to any "biological specimen" collected from a subject, and that is representative of the content or composition of the source of the sample, considered in its entirety. A sample can be collected and processed directly for analysis, or be stored under proper storage conditions to maintain sample quality until analyses are completed. Ideally, a stored sample remains equivalent to a freshly-collected specimen. The source of the sample can be an internal organ, vein, artery, or even a fluid. Non-limiting examples of sample include blood, plasma, urine, saliva, sweat, organ biopsy, cerebrospinal fluid (CSF), bone marrow, tear, semen, vaginal fluid, and breast milk.

Human macrophages are produced by the differentiation of monocytes in tissues, and can be identified and isolated using flow cytometry based on their specific expression of proteins such as CD14, CD40, CD11b, CD64, EMR1, lysozyme M, MAC-1/MAC-3 and CD68. Suitable samples include any sample that can be collected from a subject, and that includes monocytes or macrophages that can be isolated from the sample. For example, a sample can include monocytes that can further be differentiated into macrophages using well-known methods in the art; or a sample can include macrophages that can directly be isolated from the sample. In some aspects, the macrophage is from a blood or bone marrow sample.

The blood of bone marrow sample can be collected by known method in the art from a subject having a nerve injury, and in need of an administration of the macrophage composition of the present invention. In one aspect, a blood or bone marrow sample can be collected from the subject, macrophages can be isolated from the sample; the macrophages can be modified to increase MCT1 expression in the macrophage; a macrophage composition can then be generated including the modified macrophage and a pharmaceutically acceptable carrier, and administered to the subject. A portion of the collected macrophages can be kept unmodified, and used as reference macrophage. In another aspect, a blood or bone marrow sample can be collected from the subject, monocytes can be isolated from the sample and differentiated into macrophages; the macrophages can be modified to increase MCT1 expression in the macrophage; a macrophage composition can be generated including the modified macrophage and a pharmaceutically acceptable carrier, and administered to the subject. A portion of the collected macrophages can be kept unmodified, and used as reference macrophage. In other aspects, a reference macrophage can be a macrophage isolated from a donor, which is not the subject in need of an administration of the macrophage composition.

There are two types of macrophages, M1, pro-inflammatory "killer" macrophages, and M2, anti-inflammatory, pro-regenerative macrophages. M1 "killer" macrophages are activated by LPS and IFN-gamma, and secrete high levels of IL-12 and low levels of IL-10. M1 macrophages have pro-inflammatory, bactericidal, and phagocytic functions. In contrast, the M2 "repair" designation (also referred to as alternatively activated macrophages) broadly refers to macrophages that function in constructive processes like wound healing and tissue repair, and those that turn off damaging immune system activation by producing anti-inflammatory cytokines like IL-10. M2 is the phenotype of resident tissue macrophages, and can be further elevated by IL-4. M2 macrophages produce high levels of IL-10, TGF-beta and low levels of IL-12. M1 macrophages are the dominating phenotype observed in the early stages of inflammation and are activated by four key mediators: interferon-γ (IFN-γ), tumor necrosis factor (TNF), and damage associated molecular patterns (DAMPs). These mediator molecules create a pro-inflammatory response that in return produce pro-inflammatory cytokines like Interleukin-6 and TNF. Unlike M1 macrophages, M2 macrophages secrete an anti-inflammatory response via the addition of Interleukin-4 or Interleukin-13. They also play a role in wound healing and are needed for revascularization and re-epithelialization. M2 macrophages are divided into four major types based on their roles and cytokine production: M2a, M2b, M2c, and M2d. How M2 phenotypes are determined is still up for discussion but studies have shown that their environment allows them to adjust to whichever phenotype is most appropriate to efficiently heal the wound. In some aspects, the macrophage is an anti-inflammatory, pro-regenerative M2-macrophage.

As discussed above, the nerve regeneration activity of a macrophage can be assessed by evaluating glycolytic and mitochondrial activity, phagocytosis activity, production of pro-regenerative and production of pro-inflammatory cytokines, as compared to a reference macrophage. In one aspect, the macrophage has increased glycolytic and mitochondrial functions as compared to a reference macrophage that does not have an increased MCT1 gene expression.

In another aspect, the macrophage has an increased phagocytosis function as compared to a reference macrophage that does not have an increased MCT1 gene expression. Phagocytosis activity of the macrophage, in the context of nerve regeneration can be evaluated by assessing the ability of the macrophage to perform axonal phagocytosis, and myelin debris phagocytosis (Wallerian degeneration debris clearance), which reflect the ability of the macrophage to remove axonal skeleton, axonal membrane fragments, myelin sheath debris, and any other dead cells (such as neutrophils or macrophages), or cell fragments resulting from axonal degeneration after axonal nerve injury. In some aspects, the increased phagocytosis function comprises an increased axonal phagocytosis and an increased myelin debris phagocytosis (an increased Wallerian degeneration debris clearance).

In another aspect, the macrophage has an increased production of pro-regenerative cytokines as compared to a reference macrophage that does not have an increased MCT1 gene expression. In one aspect, the macrophage has a decreased production of pro-inflammatory cytokines as compared to a reference macrophage that does not have an increased MCT1 gene expression.

Following nerve injury and degeneration, macrophages can also support other cell types, such as Schwann cells, which are involved in the re-myelinization process. The nerve regeneration activity of a macrophage can therefore also be assessed by evaluating its ability to support re-myelinization, which reflects regeneration, and/or accelerated regeneration. There are various well-known methods that can be used to measure axonal regeneration. For example, myelin thickness of the regenerated nerve, the number of myelinated axons in a regenerated nerve, and g ratio of the regenerated nerve are parameters than can be evaluated. In some aspects, the increased phagocytosis function induces an increase in myelin thickness of the regenerated nerve, an increase in a number of myelinated axons in the regenerated nerve, and a decrease in a g ratio of the regenerated nerve.

Peripheral nerves can be damaged in several ways. As used herein "injured nerve" or "damaged nerve" include damaged, compressed, crushed, or sectioned nerves. Injury from an accident, a fall, sports, or any trauma can stretch, compress, crush or cut nerves. Non-traumatic conditions, such as medical conditions or certain diseases can lead to nerve damage or injury. Medical conditions, such as diabetes, Guillain-Barre syndrome Parsonage Turner syndrome and carpal tunnel syndrome can induce nerve injury. Auto-immune diseases including lupus, rheumatoid arthritis and Sjogren's syndrome can cause nerve damage. Inflammation and other medical conditions such as nerve tumor can result in nerve damage. The exposure to certain toxin such as exposure to lead, mercury, arsenic and thallium or other neurotoxins can also lead to nerve injury. In one aspect, the injured nerve results from a trauma, inflammation, non-traumatic injury, or exposure to a toxin. In some aspects, the injured or damaged nerve results from Parsonage Turner syndrome, a nerve tumor, an auto-immune neuropathy, diabetes, or a toxic neuropathy. Any injured nerve can benefit from the administration of the composition of the present invention, and from the methods described herein.

In another aspect, inducing nerve regeneration in the subject includes increasing neuroimmune interaction at a nerve injury site.

In one aspect, inducing nerve regeneration in the subject comprises increasing nerve conduction velocity (NCV) after a nerve injury. In another aspect, inducing nerve regeneration in the subject comprises increasing compound muscle action potential (CMAP) after a nerve injury. In one aspect, inducing nerve regeneration in the subject comprises increasing neuromuscular junction (NMJ) reinnervation after a nerve injury. In some aspects, increasing neuromuscular junction reinnervation after nerve injury comprises increasing an amount of full NMJ reinnervation and decreasing an amount of denervated or partially reinnervated NMJ in an injured muscle.

In another aspect, inducing nerve regeneration in the subject comprises accelerating nerve regeneration in the subject after a nerve injury.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, sub arachnoid, intraspinal and intrasternalas well infusion. The phrases "parenteral administration" and "administered parenterally" as used herein means modes of administration other than enteral and topical administration. In one aspect, administering a macrophage composition comprises intravenous, intraperitoneal and intraarterial administrations. In a preferred embodiment, the macrophage is administered to a site adjacent to or at the site of nerve damage or injury.

In some aspects, administration can be in combination with one or more additional therapeutic agents. The phrases "combination therapy", "combined with" and the like refer to the use of more than one medication or treatment simultaneously to increase the response. The composition of the present invention might for example be used in combination with other drugs or treatment in use to treat nerve degeneration or nerve damage or injury, to promote nerve regeneration, or to limit or reduce nerve further degeneration. Specifically, the administration of the macrophage composition of the invention to a subject having an injured nerve can be in combination with pro-regenerative cytokines, or anti-inflammatory cytokines. Such therapies can be administered prior to, simultaneously with, or following administration of the composition of the present invention.

Macrophages are mobiles cells, which functions include patrolling tissues to detect inflammation, infection, or pathogens. The macrophage composition of the invention can therefore be administered systemically at a distant site from the injury, or locally, at close proximity to the injured site. In some aspect, administering a macrophage composition comprises administering the composition in close proximity to the injured nerve.

In an additional embodiment, the invention provides a vector including a polynucleotide encoding MCT1 operably linked to a regulatory sequence.

Expression vectors can include regulatory elements to control transcription of the polynucleotide of interest. Non-limiting examples of regulatory elements include promoter, polyadenylation sequences, translation control sequences (e.g., an internal ribosome entry segment, IRES), enhancers, or introns. Such elements may not be necessary, although they may increase expression by affecting transcription, stability of the mRNA, translational efficiency, or the like. Such elements can be included in a nucleic acid construct as desired to obtain optimal expression of the nucleic acids in the cell(s). Vectors also can include other elements. For example, a vector can include a nucleic acid that encodes a signal peptide such that the encoded polypeptide is directed to a particular cellular location (e.g., a signal secretion sequence to cause the protein to be secreted by the cell) or a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Regulatory sequences can generally be derived from mammalian, microbial, viral or insect genes. The ability to replicate in a host, usually conferred by an origin of replication, and a selection gene to facilitate recognition of transformants. Those of skill in the art can select a suitable regulatory region to be included in such a vector.

A vector can be a genomic integrated vector, or "integrated vector," which can become integrated into the chromosomal DNA of the host cell; or an episomal vector, e.g., a nucleic acid capable of extra-chromosomal replication. Vectors capable of directing the expression of genes to which they are operatively linked are referred to herein as "expression vectors." Viral vectors include adenovirus, adeno-associated virus (AAV), retroviruses, lentiviruses, vaccinia virus, measles viruses, herpes viruses, and bovine papilloma virus vectors (see, Kay et al., Proc. Natl. Acad. Sci. USA 94:12744-12746 (1997) for a review of viral and non-viral vectors). Viral vectors are modified so the native tropism and pathogenicity of the virus has been altered or removed. The genome of a virus also can be modified to increase its infectivity and to accommodate packaging of the nucleic acid encoding the polypeptide of interest.

The term "AAV" is an abbreviation for adeno-associated virus, and can be used to refer to the virus itself or a derivative thereof. The term covers all serotypes, subtypes, and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV1, AAV2, AAV3, AAV4, AAV5, AAV6, AAV7, AAV8, AAV9, AAV10, AAV11, AAV 12, rh10, and hybrids thereof, avian AAV, bovine AAV, canine AAV, equine AAV, primate AAV, non-primate AAV, and ovine AAV.

The use of "lentiviral vector" in gene therapy refers to a method by which genes can be inserted, modified, or deleted in organisms using lentivirus. Lentivirus are a family of viruses which infect by inserting DNA into their host cells' genome. Many such viruses have been the basis of research using viruses in gene therapy, but the lentivirus is unique in its ability to infect non-dividing cells, and therefore has a wider range of potential applications. Lentiviruses can become endogenous (ERV), integrating their genome into the host germline genome, so that the virus is henceforth inherited by the host's descendants. To be effective in gene therapy, there must be insertion, alteration and/or removal of host cell genes. To do this scientists use the lentivirus' mechanisms of infection to achieve a desired outcome to gene therapy. Non-limiting examples or lentivirus that can be used for gene therapy include those derived from bovine immunodeficiency virus, caprine arthritis encephalitis virus, equine infectious anemia virus, feline immunodeficiency virus, Human immunodeficiency virus 1, Human immunodeficiency virus 2, Jembrana disease virus, puma lentivirus, simian immunodeficiency virus or Visna-maedi virus.

In some aspects, the viral vector is a lentiviral vector, an adenoviral vector or an adeno-associated viral (AAV) vector.

In a further embodiment, the invention provides an isolated macrophage including a vector having a polynucleotide encoding MCT1 operably linked to a regulatory sequence.

A nucleic acid construct (e.g., the polynucleotide encoding an MCT1, operably linked to a regulatory sequence of the present invention) may be introduced into a cell to be altered thus allowing expression of the protein within the cell. A variety of methods are known in the art and suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

In yet another embodiment, the present invention provides a macrophage cell composition including an isolated macrophage including a vector including a polynucleotide encoding MCT1 operably linked to a regulatory sequence, and a pharmaceutically acceptable carrier.

As used herein, "pharmaceutical composition" refers to a formulation comprising an active ingredient, and optionally a pharmaceutically acceptable carrier, diluent or excipient. The term "active ingredient" can interchangeably refer to an "effective ingredient", and is meant to refer to any agent that is capable of inducing a sought-after effect upon administration. In one embodiment, the active ingredient includes a macrophage including a vector including a polynucleotide encoding MCT1 operably linked to a regulatory sequence.

By "pharmaceutically acceptable" it is meant the carrier, diluent or excipient must be compatible with the other ingredients of the formulation and not deleterious to the recipient thereof, nor to the activity of the active ingredient of the formulation. Pharmaceutically acceptable carriers, excipients or stabilizers are well known in the art, for example Remington's Pharmaceutical Sciences, 16th edition, Osol, A. Ed. (1980). Pharmaceutically acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG). Examples of carrier include, but are not limited to, liposome, nanoparticles, ointment, micelles, microsphere, microparticle, cream, emulsion, and gel. Examples of excipient include, but are not limited to, anti-adherents such as magnesium stearate, binders such as saccharides and their derivatives (sucrose, lactose, starches, cellulose, sugar alcohols and the like) protein like gelatin and synthetic polymers, lubricants such as talc and silica, and preservatives such as antioxidants, vitamin A, vitamin E, vitamin C, retinyl palmitate, selenium, cysteine, methionine, citric acid, sodium sulfate and parabens. Examples of diluent include, but are not limited to, water, alcohol, saline solution, glycol, mineral oil and dimethyl sulfoxide (DMSO).

Presented below are examples discussing macrophages having an increased MCT1 expression contemplated for the discussed applications. The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Material and Methods

Transgenic mice with partial MCT1 deficiency in all cells (MCT1 heterozygous null mice) have impaired nerve regeneration after injury; but with MCT1 being expressed in virtually all cells; this does not provide further understanding of the cell-specific function of MCT1 in the cascade of cellular and molecular events following peripheral nerve injury. In order to dissect the specific role for MCT1 in peripheral nerve regeneration, MCT1 was selectively ablated from perineurial cells, Schwann cells, DRG neurons, and macrophages, all of which participate in nerve regeneration and express MCT1, by mating conditional MCT1 null mouse (MCT1$^{f/f}$) with 4 different cell-specific Cre mouse lines. With the exception of the Schwann cell-specific deletion of MCT1, the other mice were validated prior to being evaluated for nerve regeneration (see FIGS. 3, 4 and 5).

MCT1$^{f/f}$ mice (previously developed and validated) were bred with transgenic mice with Cre recombinase driven by LysM-Cre (Jackson Laboratory; stock no: 004781), P0-Cre (Jackson Laboratory; stock no. 017927), Adv-Cre (published previously; obtained from the Laboratory of Ahmet Hoke at Johns Hopkins University), and Gli1-CreER$^{T2}$ (Jackson Laboratory; stock no. 007913) to generate cell-specific ablation of MCT1 from macrophages (LysM-Cre: MCT1$^{f/f}$), Schwann cells (P0-Cre:MCT1$^{f/f}$), DRG neurons (Adv-Cre:MCT1$^{f/f}$), or perineurial cells (Gli1-Cre$^{ER72}$: MCT1$^{f/f}$) and littermate controls (see FIGS. 1A, 2A, 2C and 2E). With the exception of the adoptive cell transfer experiments, the mice in all experiments were mixed background composed of C57Bl6 and SJL mice. As detailed below, both mixed and C57Bl6 congenic background mice had delayed nerve regeneration following ablation of macrophage MCT1. Gli1-Cre$^{ER72}$:MCT1$^{f/f}$ mice were treated with tamoxifen (125 mg/kg/body weight, i.p.) every alternate day over 7 days at approximately 2 months of age, as described previously, to induce recombination of MCT1 gene. Gli1-Cre$^{ER72}$:MCT1$^{f/f}$ mice were used for studies at least two weeks after tamoxifen treatment. Animals were monitored for adverse effects of treatment, but none were noted during or after the course of treatment that required euthanasia. Transgenic mice with upregulation of MCT1 selectively in macrophages (LysM-Cre:tTA$^{+/-}$:MCT1$^{Over/+}$) were produced by crossing LysM-Cre mice with ROSA LNL tTA (tet-off) mice (Jackson Laboratory; stock no: 011008) and a tet-responsive MCT1 overexpressor mouse (MCT1Over/+ published previously[50]. Additionally, transgenic mice with macrophage-specific, doxycycline-inducible MCT1 expression, (CD68-rtTA:MCT 1$^{Over/+}$) were produced by mating CD68-rtTA (tet-on; The Jackson Laboratory; MMRRC stock no: 32044-JAX) mice with MCT1$^{Over/+}$ mice. MCT1 overexpression was induced by providing mice with doxycycline ad libitum in their mouse chow (VWR, #89067-462) for at least two weeks. Genotypes for knockout or overexpressor mice and littermate control mice were performed as described previously[62,65] and/or by using the protocols obtained from the providers. At baseline, none of these knockout or overexpressor mice and littermate control mice showed any signs of peripheral neuropathy.

All surgical experiments were performed under 2% isoflurane on adult male or female littermate mice (~100 days old). As published previously, and as illustrated in FIG. 1B, sciatic nerve crush injury was performed by exposing right sciatic nerve at mid-thigh level, crushing sciatic nerve with smooth forceps for 20 seconds, closing the skin incision with surgical staples, and allowing the animals to recover on a warming blanket.

At various time point after recovery, nerve conduction studies, nerve immunohistochemistry and morphometry studies were performed. Electrophysiologic recordings were performed to measure compound muscle action potentials (CMAPs) by using a Neurosoft-Evidence 3102evo electromyograph system (Schreiber & Tholen Medizintechnik, Stade, Germany). During all recording sessions, mice were anesthetized with 2% isoflurane and positioned face down. CMAPs were determined by placing stimulating electrodes (27 G stainless steel needle electrodes, Natus Medical, Inc., San Carlos, CA) at the sciatic notch and Achilles tendon, and recording electrodes in the lateral plantar muscles of the foot. Stimulation of each nerve segment was performed, with increasing voltage, until the maximal response was achieved, as evidenced by no further increase or decrease in CMAP amplitude, despite an increase in stimulation voltage. Nerves were stimulated by very short (<0.2 ms) electrical impulses. Response latency for each proximal or distal stimulation was measured from stimulus onset, and peak-to-peak amplitudes were calculated. Motor NCV was calculated by dividing the distance between sciatic notch and Achilles tendon by the difference between the response latencies. Unless otherwise stated, all nerve conduction studies were conducted at room temperature. The investigator performing electrophysiologic recordings was blinded to mice genotypes throughout the study. Deeply anesthetized mice were transcardially perfused with 0.1 M phosphate-buffered saline followed by 4% paraformaldehyde fixative and nerves or DRGs were dissected. Tissue for immunofluorescence staining was post-fixed for 4 hours in 4% paraformaldehyde, cryoprotected in 30% sucrose and sectioned on a Leica CM1900 cryostat. Sections (20 µm thickness) were immunostained on slides for MCT1 (generated for our laboratory[32]; 1:200), Iba-1 (Wako; 1:2000), F4/80 (ThermoFisher; 1:500)), or Claudin1 (Novus; 1:200) either alone or in combination. Photomicrographs were acquired with ZEN Digital Imaging for LSM 800 (Zeiss). For the quantification of infiltrated macrophages in injured sciatic nerves, Z-stack of images were acquired, and the number of Iba-1-positive cells were counted per 20 µm thick cross-section. Tissue for semi-thin nerve histology was post-fixed with 2.5% glutaraldehyde in 4% paraformaldehyde for at least 3 days and embedded in Epon 812 resin. Embedded nerves were cut semi-thin (1 µm) and stained with toluidine blue. Toluidine blue-stained sections were used for quantification of myelinated axon number, myelinated axon diameter, or g ratio. Our technique is well supported in the literature, as an identical procedure has been followed in a number of publications. For each of these histologic features, photomicrographs of nerves were taken on Nikon E800, imported and quantified manually with Zeiss Axio-Vision 4.8 software. g ratio was calculated as the ratio of the diameter of axons divided by the diameter of myelin sheaths. If more than one fascicle was present in a sample, the largest nerve fascicle was quantified in its entirety. An experimenter, who was blinded to animal genotypes, performed all morphometric analyses.

NMJ morphology was studied in the gastrocnemius muscle. Gastrocnemius muscles were isolated from deeply anesthetized mice after perfusion through the aorta with ice-cold 0.1 M phosphate-buffered saline followed by 4% PFA fixative, post-fixed in the same PFA fixative for 2 hours at 4° C., and cryoprotected in 30% sucrose in 0.1 M phosphate-buffered saline overnight at 4° C. Muscles were frozen at −80° C. in cryo-embedding medium (Tissue-Tek O.C.T. compound), cut into 50 µm longitudinal sections on a cryostat, and placed in 0.1 M phosphate-buffered saline. Sections were washed in 0.3% Triton X-100 in phosphate-buffered saline and incubated for 2 hours at room temperature in a blocking solution (phosphate-buffered saline supplemented with 3% bovine serum albumin, 5% normal goat serum, 0.3% Triton-X100). The sections were then incubated for two overnights at 4° C. with a mixture of anti-SMI 312 (mouse monoclonal; 1:1000; Catalog #837904; Biolegend), and synaptophysin (rabbit monoclonal; 1:500; Catalog #MA5-14532; Thermo Fisher Scientific) diluted in the blocking solution. After washing 4 times for 1 hour each with 0.3% Triton X-100 in phosphate-buffered saline at room temperature, sections were incubated with secondary antibodies against Fluorescein isothiocyanate Goat-anti-Mouse IgG1 (FGM, 1:200; Jackson Immuno), Alexa Fluor 647 Goat-anti-Rabbit (1:1000; Thermo Fisher Scientific), α-Bungarotoxin (Alexa Fluor™ 555 conjugate; 1:500; Catalog #B35451; Thermo Fisher Scientific) diluted in blocking solution overnight at 4° C. After washing 4 times for 1 hour each with 0.3% Triton X-100 in phosphate-buffered saline at room temperature, sections were transferred on slides, and slides were mounted with Prolong Gold anti-fade mountant media (Thermo Fisher Scientific). Z-stack of images were acquired at ×20 magnification with ZEN Digital Imaging for LSM 800 (Zeiss) and analyzed by using ZEN blue edition software (Zeiss) as described previously. Briefly, between 150 and 200 endplates were evaluated for each muscle at each time point. Reinnervated acetylcholine receptor (AChR) clusters were categorized as fully reinnervated AChR clusters (Full Inn; 80%-100% overlap), partially reinnervated AChR clusters (Partial Inn; 10%-80% overlap), and denervated AChR clusters (Den; <10% overlap).

For mRNA expression evaluation, RNA was isolated and prepared for quantitative real-time reverse transcription-PCR reactions. Deeply anesthetized mice were transcardially perfused with 0.1 M phosphate-buffered saline to remove the blood, and the sciatic nerves were rapidly dissected. RNA was isolated by an RNeasy Mini Kit (Qiagen), reverse transcribed to cDNA with a High Capacity cDNA Reverse Transcription Kit (Applied Biosystems) and quantified by real-time RT PCR using Taqman probes (Applied Biosystems) for MCT1 (Thermo Fisher Scientific; Catalog #4351372), MCT2 (Thermo Fisher Scientific; Catalog #4331182), MCT4 (Thermo Fisher Scientific; Catalog #4331182), GLUT1 (Thermo Fisher Scientific; Catalog #4331182), GLUT3 (Thermo Fisher Scientific; Catalog #4331182), TNF-α (Thermo Fisher Scientific; Catalog #4331182), IL-1β (Thermo Fisher Scientific; Catalog #4351372), IL-6 (Thermo Fisher Scientific; Catalog #4351372), Ym1 (Chil3) (Thermo Fisher Scientific; Catalog #4351372), Arg-1 (Thermo Fisher Scientific; Catalog #4351372), Ly6G (Thermo Fisher Scientific; Catalog #4331182), or GAPDH (Thermo Fisher Scientific; Catalog #4352339E) on a StepOne Plus RT-PCR System (Applied Biosystems).

Peritoneal exudate macrophages were isolated as described previously. Briefly, mice were intraperitoneally injected with 3 ml of 3% sterile thioglycolate (BD Biosciences), and 4 days later, peritoneal exudate cells were collected by lavage with phosphate-buffered saline. Aliquots of 1×10$^6$ cells were seeded in 6-well polystyrene culture plates at 37° C. and 5% CO2 atmosphere and allowed to adhere for 3 hours before washing. Afterward, nonadherent cells were removed by vigorous washing three times with phosphate-buffered saline and incubated for an additional 24 hours under the same conditions before any treatment or analysis. Cells were untreated or incubated with LPS (100 ng/ml) plus IFN-γ (50 U/ml) or IL-4 (10 ng/ml) for a desired period of time and then used for total RNA or protein extraction. The entire procedure was performed under sterile conditions.

For measurements of oxygen consumption and extracellular acidification (Seahorse bioenergetic analysis), peritoneal exudate macrophages were analyzed using XF96 extracellular flux analyzer (Seahorse Bioscience, North Billerica, MA) following the manufacturer's instructions. Macrophages were grown in the Seahorse XF96 cell culture microplate at 10,000 cells/well. Bioenergetic analysis was performed by sequentially injecting 2 µM oligomycin, 4 µM carbonyl cyanide p-(trifluoromethoxy) phenylhydrazone (FCCP), 0.5 µM rotenone and 4 µM antimycin. Data are expressed as oxygen consumption rate (OCR) in picomole per minute and extracellular acidification rate (ECAR) in milli pH per minute for 10,000 cells. Total ATP generated from oxidative metabolism was estimated by the following formula: ATPoxid=(OCRmito×P/OTCA+OCRcoupled×P/Ooxid)×2. OCRmito=OCRtotal−OCRrot. P/OTCA ratio is 0.121. OCRcoupled=(OCRtotal−OCRoligo)×0.908. P/Ooxid ratio is 2.486. Total ATP generated from glycolysis was estimated by the following formula: ATPglyc=PPRglyc+OCRmito×2ATP/lactate×P/Oglyc. PPRglyc=PPRtot−PPRresp. PPRtot=ECAR×0.1 (buffering power for DMEM). PPRresp=$(10^{(pH-pK)}/1+10^{(pH-pK)})\times$ OCRmito. ATP/lactate=1. P/Oglyc ratio is 0.242. oxid; oxidative phosphorylation; mito: mitochondrial; P/O ratio: yield of ATP per Oxygen atom consumed; rot: rotenone; TCA: tricarboxylic acid cycle; oligo: oligomycin; PPR: proton production rate. The rationale and explanation for these formulas has been published previously.

Protein expression was analyzed by western blotting. Peripheral nerves dissected after transcardial perfusion of deeply anesthetized mice with 0.1 M phosphate-buffered saline were homogenized in T-PER (Thermo Scientific) and run on Mini-Protean TGX Gels (10%; Bio-Rad) and transferred to nitrocellulose membranes (Bio-Rad). For all Western blots, 15-30 µg of proteins were separated on the gel. Membranes were incubated overnight with MCT1 (generated for laboratory[32]; 1:200) and visualized with Amersham ECL Reagant (GE Healthcare) on ImageQuant LAS 4000 (GE Healthcare). After visualizing for above primary antibodies, blots were stripped with Restore Western Blot Stripping Buffer (Thermo Scientific), reprobed overnight with β-Actin (Millipore Sigma; catalog #A5316; monoclonal anti-β-actin antibody; 1:5,000), and again visualized by ECL reagent, as described above.

The lactate uptake assay was completed as described previously. In brief, cells were incubated with 0.5 µCi ml$^{-1}$ L-[1-$^{14}$C] lactic acid (Perkin-Elmer) in HEPES-buffered, Earl's balanced salt solution (HEBSS) buffer, pH 6.0, containing 150 mM NaCl, 5 mM KCl, 1 mM KH2PO4, 0.2 mM CaCl2·2H2O, 3.3 mM MOPS, 10 mM HEPES, 1 mM MgSO4·7H2O. After incubation, uptake was stopped by quickly chilling the cultures to 4° C. Cells were washed with ice-cold HEPES buffer, homogenized in 0.1 M NaOH and 0.1% Triton X-100, and centrifuged at 13,780 g for 10 min. Radioactivity was measured by scintillation counting and corrected by protein amount.

Phagocytosis assay of macrophages was performed as described previously. Peritoneal exudate macrophages were plated in collagen-coated 8-well chamber slides at about 70% confluency. To prepare FluoSpheres Carboxylate-Modified Microsphere (1 µm, red fluorescent; Life Technologies F-8826), 2 µL microspheres were suspended in 100 µL phosphate-buffered saline with 1 mg/mL bovine serum albumin. Then 20 µL were added per well. Microspheres were allowed to settle onto cells for 2 hours in 37° C. and 5% CO2 atmosphere. Media was removed, and cells were gently washed 3 times with phosphate-buffered saline then fixed with 4% PFA for minutes. Macrophages were immunostained with anti-CD68 antibody (anti-macrophages/monocytes antibody; mouse monoclonal antibody; 1:200; Millipore Sigma). Confocal analysis was performed to visualize and count the number of cells with internalized fluorescent microspheres and was presented in percent.

Bone marrow-derived macrophages (BMDMs) were generated as described previously for adoptive cell transfer experiments. Briefly, bone marrow cell suspension was prepared by flushing bone marrow with DMEM supplemented with 10% fetal bovine serum (FBS), 1% penicillin/streptomycin and 2 mM L-glutamine plus 20% L929-conditioned medium. The cells were incubated at 37° C. and 5% CO2 atmosphere, and on day 4, non-adherent cells were removed, and the medium was replenished. On day 7, BMDMs were lifted using Cellstripper (Mediatech, Manassas, VA) and dispersed in phosphate-buffered saline. BMDMs (5×10$^6$ cells/100 µL/mouse) were injected via tail vein 3 days after sciatic nerve crush.

Analyses were performed blinded to animal genotype and treatment. Although no statistical tests were performed to predetermine sample size, samples sizes were similar to previously published studies in the field. Statistical analyses were performed with GraphPad Prism 8 (GraphPad Software) by using unpaired t test with two tails with unequal variance or two-way ANOVA with post hoc test when required conditions were met. The number of animals per group or independent repeats (n), the statistical test used for comparison, and the statistical significance (p value) was stated for each figure panel in the respective legend. All data were presented as the mean±SEM unless otherwise noted. Differences in the p values of <0.05 were considered statistically significant.

Example 2

Macrophage-Selective MCT1 Ablation and Peripheral Nerve Regeneration Following Injury In order to dissect the specific role for MCT1 in peripheral nerve regeneration, MCT1 was selectively ablated from perineurial cells, Schwann cells, DRG neurons, and macrophages, all of which participate in nerve regeneration and express MCT1, by mating conditional MCT1 null mouse (MCT1$^{f/f}$) with 4 different cell-specific Cre mouse lines. With the exception of the Schwann cell-specific deletion of MCT1, the other mice were validated prior to being evaluated for nerve regeneration (see FIGS. 3, 4 and 5).

As detailed in FIG. 4, the validation of perineurial cell-specific MCT1 deficient mice shown significantly reduced protein level of MCT1 in sciatic nerves from Gli1-Cre:MCT1$^{f/f}$ and littermate control mice; as assessed by Western blot analysis (full-length Western blots for MCT1 and β-actin, used as a loading control; and complete co-localization of Gli1-Cre expression (GFP) with Claudin1, a marker for perineurial cells. MCT1 protein quantified by densitometry of lower 3 bands, as detailed previously, was normalized to β-actin and presented as fold change relative to control (MCT1$^{f/f}$). Mean±SEM, n=3 per group, **p<0.01; unpaired t test (FIGS. 4A and 4B). Gli1-Cre:RosaYFP nerve images were representative confocal micrographs of at least three independent experiments. Calibration bar: 20 µm (FIG. 4C). MCT1 and Claudin1 immunoreactivity images in sciatic nerves from MCT1$^{f/f}$ and LysM-Cre:MCT1$^{f/f}$ mice were representative confocal micrographs of at least three independent experiments. Calibration bars: 50 µm for left panel and 10 µm for right panel (FIG. 4D).

Figure 5A:
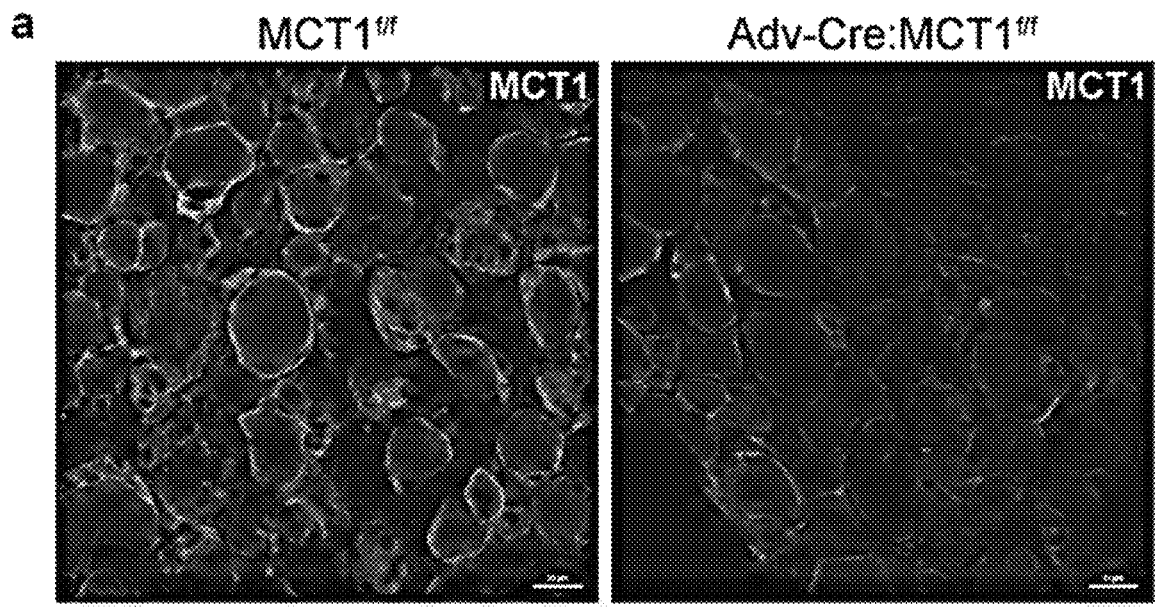
FIGS. 5A-5D illustrate the validation of DRG neuron-specific MCT1 deficient mice.
Figure 5B:
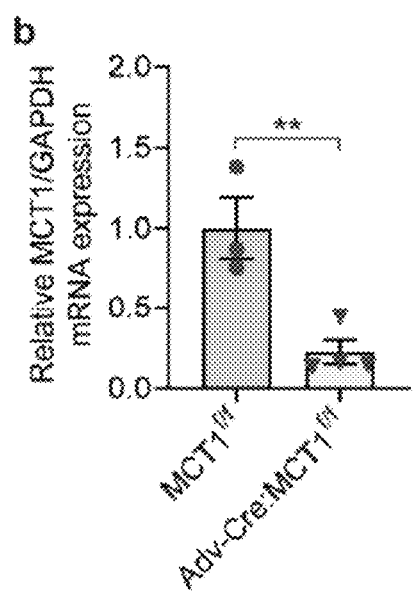
Figure 5C:
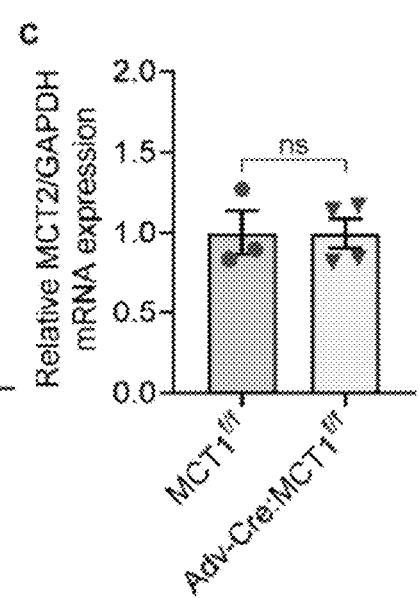
Figure 5D:
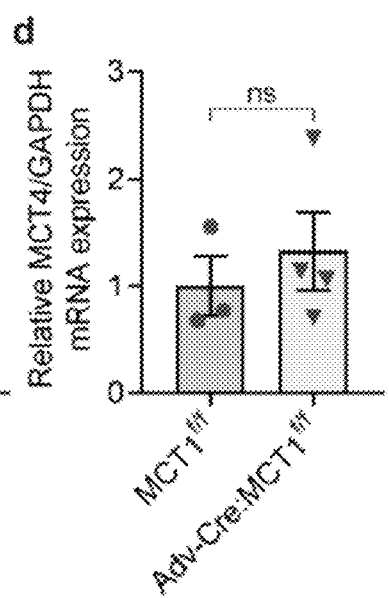

As further detailed in FIG. 5, the validation of DRG neuron-specific MCT1 deficient mice shown significant reduction of both MCT1 immunoreactivity in Adv-Cre:MCT1$^{f/f}$ compared with their littermate control mice (MCT1$^{f/f}$) (FIG. 5A), and MCT1 levels of expression, with no effect on MCT2 or MCT4 mRNAs (FIGS. 5B, 5C and 5D). Sections were processed and imaged together and under identical conditions. Images are representative confocal micrographs of at least three independent experiments. mRNAs levels were evaluated in DRGs dissected from Adv-Cre:MCT 1$^{f/f}$ and littermate control mice. Levels of mRNAs were depicted as fold change compared with littermate control mice normalized to their corresponding GAPDH mRNA levels. Mean±SEM, n=3-4 per group, **p<0.01; ns=not significant; unpaired t test.

For all cell types, with the exception of macrophages, the conditional deletion of MCT1 had no impact on nerve regeneration following sciatic nerve crush in proximal thigh, measured electro-physiologically by recovery of motor nerve condition velocity (NCV) and compound muscle action potentials (CMAPs) (FIGS. 1A, 1B and 1C and FIGS. 2A, 2B, 2C, 2D, 2E and 2F). Specifically, as shown in FIG. 2, were recoveries are presented as percent relative to pre-crush conditions, no significant difference in NCV or CMAP recovery was found at any time-point due to any cell-specific MCT1 deficiency. Mean±SEM, n=6-10 per group, two-way ANOVA with Bonferroni's multiple comparisons test.

Peritoneal exudative macrophages isolated from mice with macrophage-specific MCT1 deficiency (LysM-Cre:MCT$^{f/f}$) have both reduced expression of MCT1 and lactate transport (FIGS. 3A and 3B). A compensatory increase in MCT2 and GluT3, but not MCT4 or GluT1, were seen in peritoneal exudative macrophages isolated from LysM-Cre:MCT1$^{f/f}$ mice (FIGS. 3C, 3D, 3E and 3F). For the validation of macrophage-specific MCT1 deficient mice, the expression of monocarboxylate transporters, MCT1, MCT2, and MCT4, and glucose transporters, GLUT1 and GLUT3, mRNAs were evaluated in peritoneal exudate macrophage cultures prepared from LysM-Cre:MCT1$^{f/f}$ and littermate control mice. Levels of mRNAs are depicted as fold change compared with littermate control mice normalized to their corresponding GAPDH mRNA levels. Mean±SEM, n=5-9 per group, *p<0.05, p<0.01 *p<0.001; ns=not significant; unpaired t test. The lactate uptake and blockade by selective MCT1 inhibitor in peritoneal exudate macrophage cultures was prepared from LysM-Cre:MCT1$^{f/f}$ and littermate control mice. Mean±SEM, n=4-5 per group, *p<0.05; ns=not significant; two-way ANOVA with Bonferroni's multiple comparisons test.

Figure 6A:
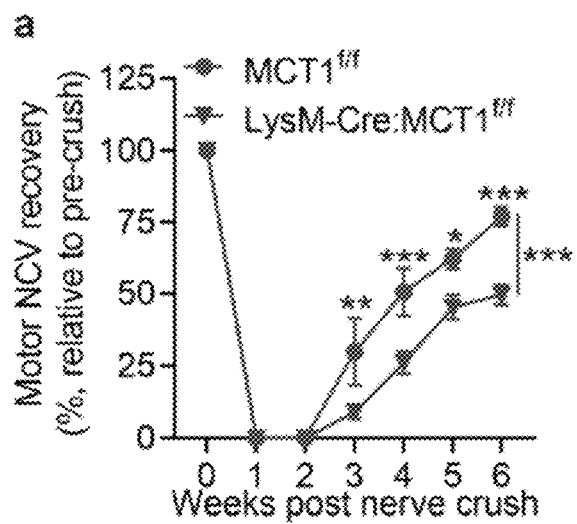
FIGS. 6A-6B illustrate nerve regeneration in macrophages in the context of MCT1 deficiency.
Figure 6B:
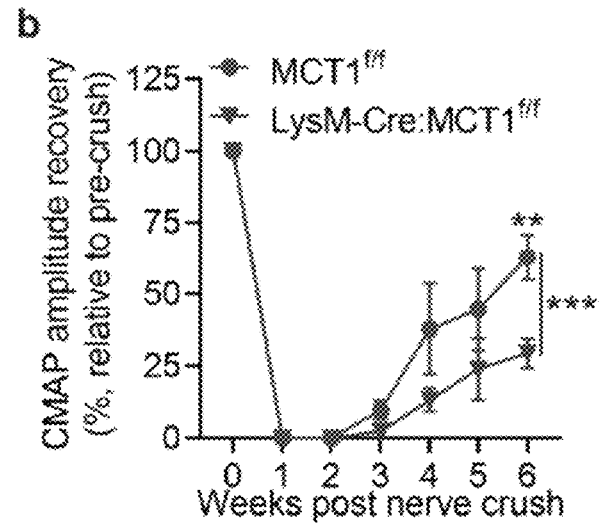

Following sciatic nerve crush, there was a delay in nerve regeneration, measured by slowed recovery of both nerve conduction velocity (FIG. 1C) and CMAP amplitude (FIG. 1D) in male LysM-Cre:MCT$^{f/f}$ mice. Recoveries were presented as percent relative to pre-crush conditions. Mean±SEM, n=13 (for MCT1$^{f/f}$ group) or 11 (for LysM-Cre:MCT1$^{f/f}$ group), *p<0.05, p<0.01, **p<0.0001; two-way ANOVA with Bonferroni's multiple comparisons test. Slow electrophysiological recovery after nerve injury was also confirmed in female mice, suggesting that the delayed regeneration after nerve injury observed due to MCT1 deficiency in macrophages is independent of gender (FIGS. 6A and 6B). Recoveries were presented as percent relative to pre-crush conditions. Mean±SEM, n=4 (for MCT1$^{f/f}$ group) or 6 (for LysM-Cre:MCT 1$^{f/f}$ group), *p<0.05, p<0.01, **p<0.0001; two-way ANOVA with Bonferroni's multiple comparisons test.

The degree of motor and sensory recovery were further measured by evaluating NMJ distribution in gastrocnemius muscle and morphometric analysis of sural nerves, respectively. At 6 weeks after nerve crush, NMJ full reinnervation was significantly less in LysM-Cre:MCT$^{f/f}$ mice (FIGS. 1E, 1F, 1G and 1H). Neuromuscular junctions (NMJs) in gastrocnemius muscles were visualized by staining the muscles with α-Bungarotoxin (BTX, Alexa Fluor™ 555 conjugate) to visualize AChRs, anti-SMI312 antibody to visualize neurofilaments, and anti-synaptophysin antibody to visualize nerve terminals. The percentage of fully reinnervated, partially reinnervated, and denervated AChR clusters in mice with macrophage-specific MCT1 deficiency were compared with their littermate controls 3 weeks and 6 weeks after crush. Mean±SEM, n=3-4 per group, *p<0.05; ns=not significant; two-way ANOVA with Bonferroni's multiple comparisons test.

Figure 1L:
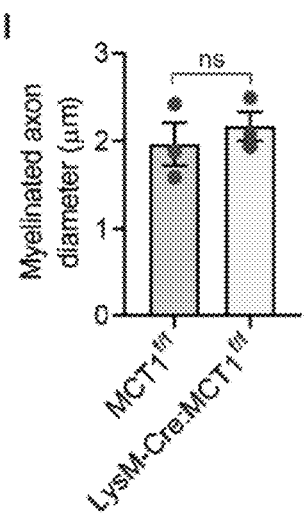
FIG. 1L is a bar graph illustrating myelinated axon diameter of sural nerve 3 weeks after sciatic nerve crush. Mean±SEM, n=3-4 per group, ns=not significant.
Figure 1M:
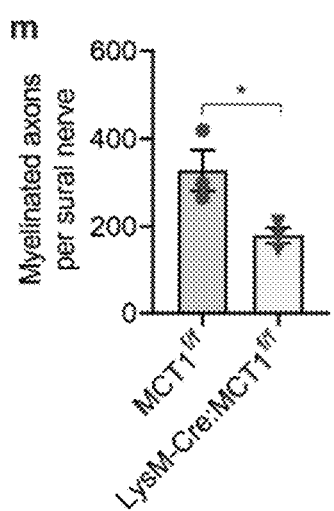
FIG. 1M is a bar graph illustrating myelinated axon count of sural nerve 3 weeks after sciatic nerve crush. Mean±SEM, n=3-4 per group, *p<0.05.
Figure 2E:
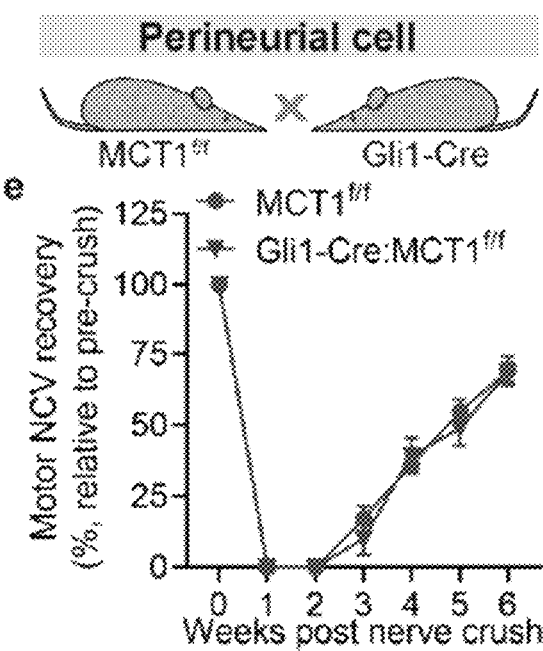
Figure 2F:
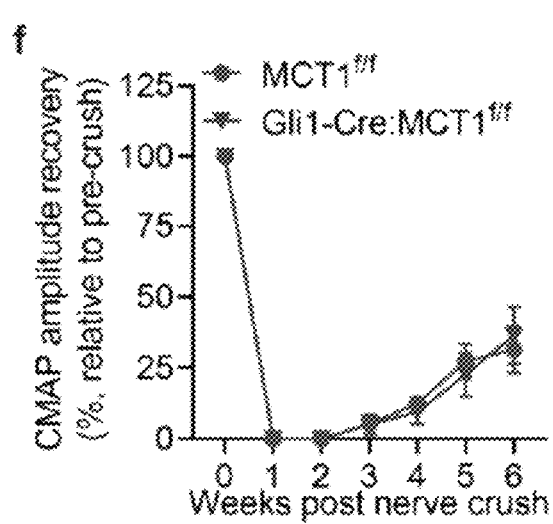
Figure 4A:
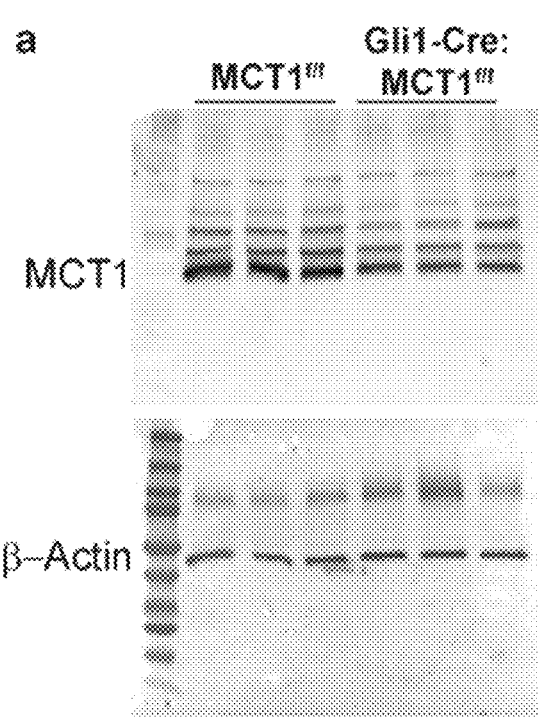
FIGS. 4A-4D illustrate the validation of perineurial cell-specific MCT1 deficient mice.
Figure 4B:
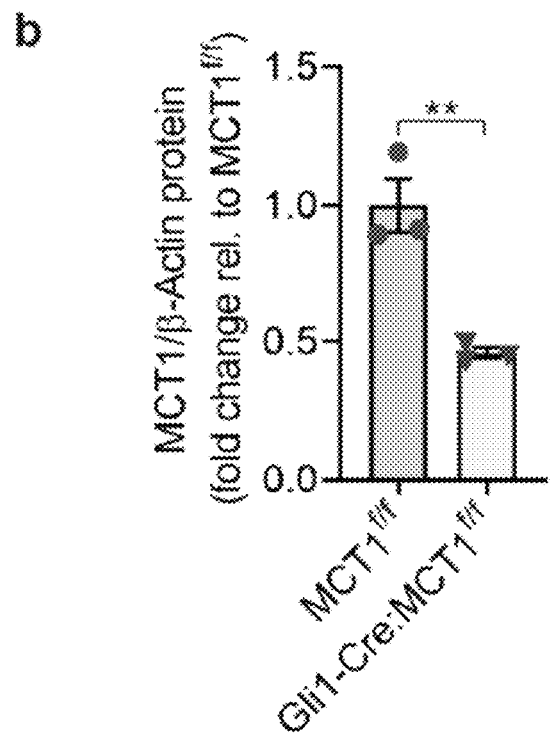
Figure 4C:
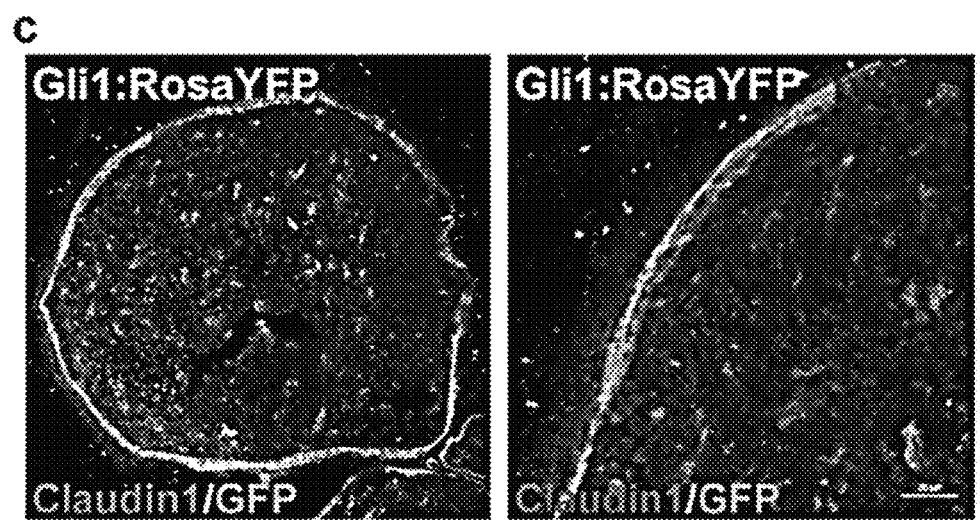
Figure 4D:
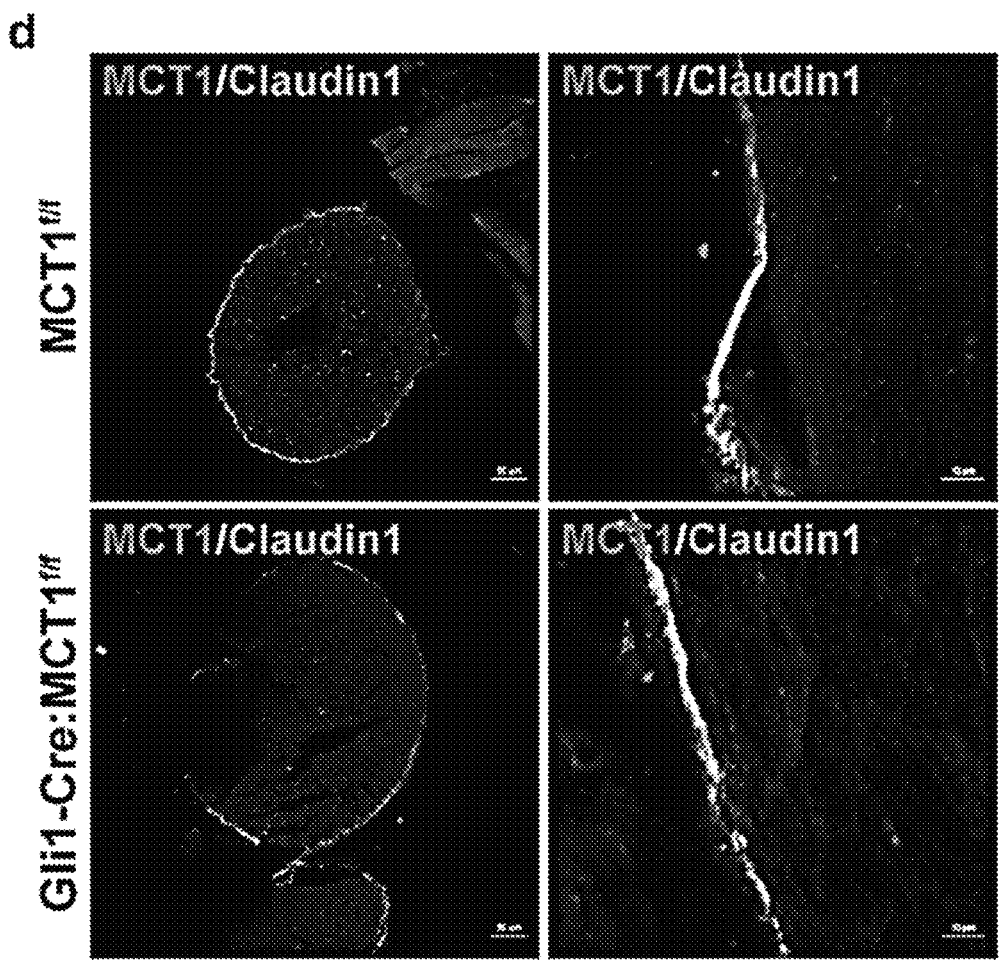

Myelin was thinner (reflected by increased g ratio) at 3 and 6 weeks (FIGS. 1I, 1J, 1K and 1N, 1O, 1P, respectively) and the number of regenerated axons was reduced at 3 weeks (FIG. 1M) after sciatic nerve crush in LysM-Cre:MCT$^{f/f}$ mice. There was not significant difference at any time in the myelinated axon diameter (FIGS. 1L and 1Q). Importantly, neither LysM-Cre:MCT$^{f/f}$ nor MCT$^{f/f}$ control mice showed any sign of peripheral neuropathy during the study, since electrophysiology and histology from the uncrushed nerves was unaltered throughout the study (data not shown). Light microscope photomicrographs and subsequent analysis were completed on toluidine blue-stained sections. Mean±SEM, n=3-4 per group, *p<0.05; **p<0.01; ns=not significant, unpaired t test. From these studies, it was concluded that MCT1 expressed in macrophages, but not in perineurial cells, Schwann cells, or DRG neurons, plays a role in peripheral nerve regeneration and its deficiency impairs recovery following nerve injury. Furthermore, LysM-Cre:MCT$^{f/f}$ mice can be used to examine the role of MCT1 in macrophage immunometabolism.

Example 3

Effects of Macrophage MCT1 on Inflammatory Cytokine Expression in Injured Peripheral Nerves and Macrophage Recruitment Neuroimmune interactions play a crucial role in peripheral nerve regeneration after injury. Pro-regenerative macrophages are active participants in tissue repair and remodeling, and have a crucial role in peripheral nerve regeneration after injury as well. Nerve injury disrupts the axon/Schwann cell nerve unit, which results in production of chemokines and cytokines to activate resident nerve macrophages and recruit circulating monocytes/macrophages. Recruited macrophages are crucial to remove debris (Wallerian degeneration) and promote regeneration.

Figure 7E:
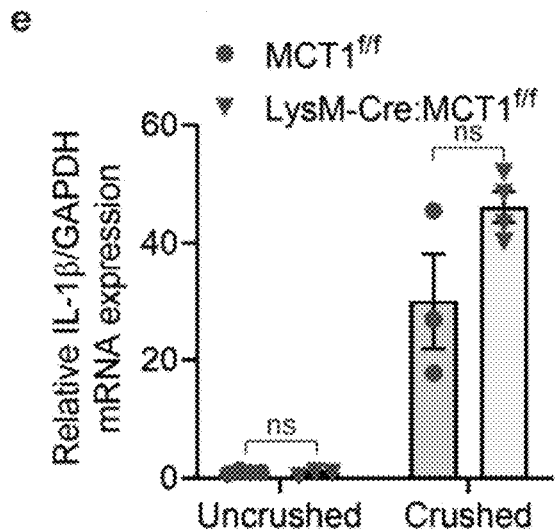
Figure 7F:
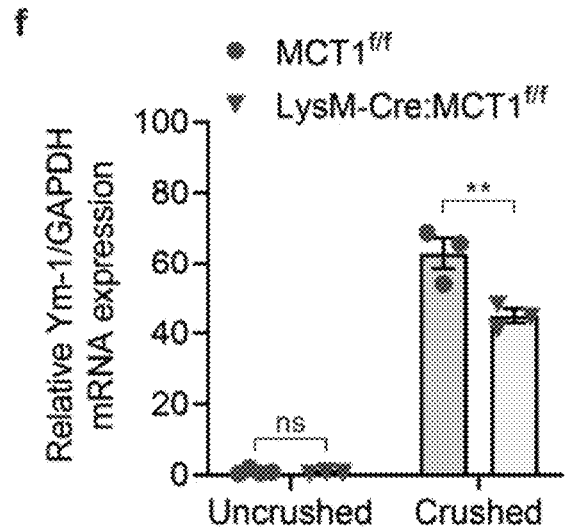
Figure 7G:
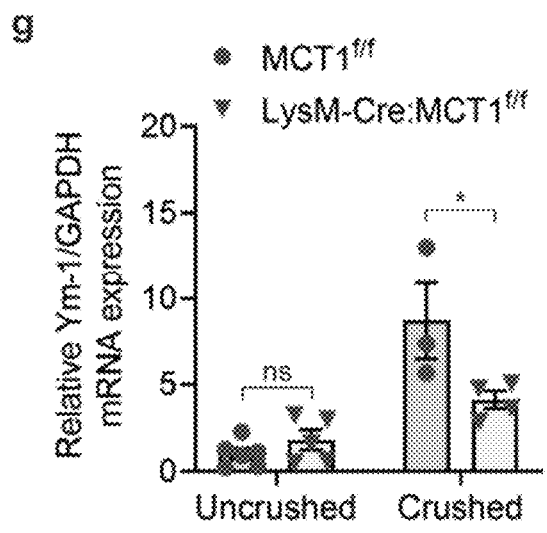
Figure 7H:
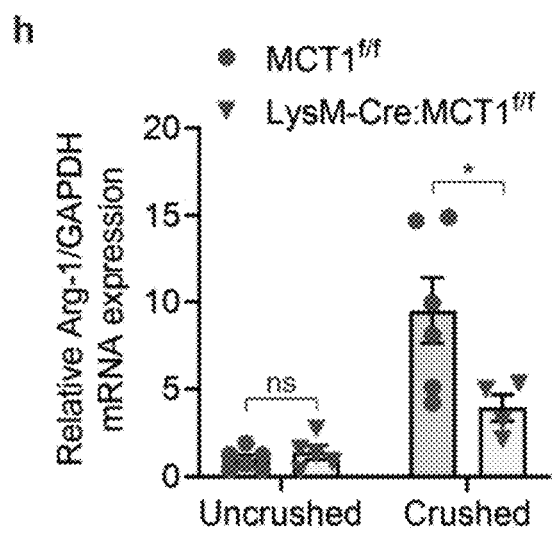

As illustrated in FIGS. 7A and 7B, it was found that removing MCT1 from macrophages in LysM-Cre:MCT$^{f/f}$ mice had no impact on the number of macrophages infiltrating the injured nerve. Total Iba1-positive macrophage counts were obtained from Z-stack of images of 20 µm thick complete cross-sections of nerve. Mean±SEM, n=4-7 per group, ns=not significant, two-way ANOVA with Bonferroni's multiple comparisons test.

Figure 8:
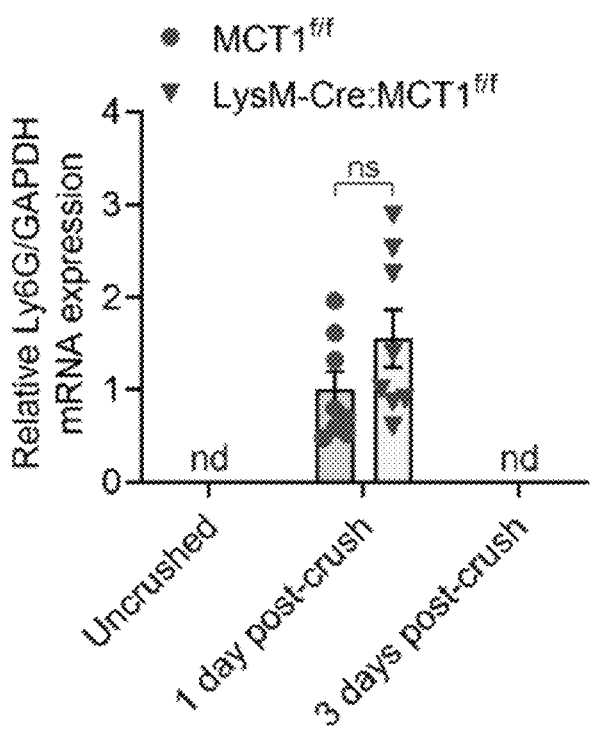
FIG. 8 is a bar graph illustrating the mRNA expression of Ly6G in uncrushed and crushed sciatic nerves (distal to site of injury) evaluated by real-time RT-PCR. Mean±SEM, nd, not detected; n=5-8 per group, ns=not significant.

In addition to expressing highly and recombining in macrophages, LysM-Cre is also expressed in neutrophils. Since neutrophils also express MCT1 and have been shown to play a role in Wallerian degeneration following nerve injury, whether neutrophil migration following nerve injury was evaluated in LysM-Cre:MCT$^{f/f}$ mice. Neutrophils are recruited to the endoneurium immediately after injury and persist for 2-3 days, where they are important for cytokine generation and modulating macrophage phenotype and function. Hence, the expression of Ly6G, which is expressed most highly in murine neutrophils was measured. Ly6G expression was not detected in uninjured sciatic nerves, but was present 1 day following sciatic nerve crush (FIG. 8). The mRNA expression of Ly6G in uncrushed and crushed sciatic nerves (distal to site of injury) was evaluated by real-time RT-PCR and depicted as fold change compared with crushed sciatic nerve (1-day post crush) isolated from control mice (MCT1$^{f/f}$) normalized to their corresponding GAPDH mRNA levels. Mean±SEM, nd, not detected; n=5-8 per group, ns=not significant, unpaired t test. Neutrophils, as measured by Ly6G expression, were gone 3 days following nerve crush. Importantly, there was no change in Ly6G expression between LysM-Cre:MCT$^{f/f}$ and MCT$^{f/f}$ mice, suggesting no discrepancy in neutrophil infiltration to the site of injury following MCT1 deletion.

In order to assess for alterations in macrophage or neutrophil phenotype, select pro-inflammatory and pro-regenerative cytokines from sciatic nerve at 1, 3, and 10 days following crush were quantified (FIGS. 7C, 7D, 7E, 7F, 7G and 7H). These specific time points were chosen because 1 day represents activation of neutrophils and nerve resident macrophages, 3 days is the time for maximal pro-inflammatory cytokines from circulating macrophages, and 10 days is the stage of maximal pre-regenerative cytokines from circulating macrophages. As expected, uncrushed nerves had minimal expression of cytokines at any time point and there was no difference between LysM-Cre:MCT$^{f/f}$ and MCT$^{f/f}$ mice.

At 1 day following crush, two prototypic pro-inflammatory cytokines that have been implicated as main effectors of the functional consequences in diverse inflammatory cascades, interleukin-1β (IL-1β) and tumor necrosis factor-α (TNF-α), were significantly increased in LysM-Cre:MCT$^{f/f}$ mice (FIGS. 7C and 7D).

At 3 days after crush, IL-1β was increased, though this change was not statistically significant (FIG. 7E), while TNF-α was not changed in LysM-Cre:MCT$^{f/f}$ mice (FIG. 9A). By 10-day post-crush, IL-1β was not different between LysM-Cre:MCT$^{f/f}$ and MCT$^{f/f}$ mice (FIG. 9C). For the assessment of impact on pro-regenerative macrophages, we measured the expression of chitinase-like 3 (Ym-1) and arginase, type I (Arg-1), which are markers for murine, but not human, alternatively activate myeloid cells. In contrast to the overall increased expression of pro-inflammatory cytokines, these pro-regenerative cytokines were generally reduced in LysM-Cre:MCT$^{f/f}$ mice. Ym-1 was reduced in the sciatic nerve of LysM-Cre:MCT$^{f/f}$ mice at 3 and 10 days and Arg-1 at 10 days following crush (FIGS. 7F, 7G, 7H and FIG. 9B). These findings suggest that MCT1 contributes to macrophage phenotype and the cytokine microenvironment of injured nerves. Levels of mRNAs were depicted as fold change compared with uncrushed sciatic nerve isolated from control mice (MCT1$^{f/f}$) normalized to their corresponding GAPDH mRNA levels. Mean±SEM, n=3-9 per group, *p<0.05; p<0.01; *p<0.001; ns=not significant, two-way ANOVA with Bonferroni's multiple comparisons test.

Example 4

Contribution of MCT1 to Metabolic Function of Macrophages In Vitro

Intracellular metabolism has been acknowledged as a key determinant of macrophage phenotype and function. To understand the metabolic impact of MCT1 deletion, the capacity for glycolysis and oxidative metabolism of macrophages with and without MCT1 was measured by quantifying the rate of extracellular cellular acidification rate (ECAR; FIG. 10A) and real-time oxygen consumption (OCR; FIG. 10B), respectively, in a live cell assay with the Seahorse extracellular flux analyzer. Macrophages derived from LysM-Cre:MCT$^{f/f}$ mice have significantly reduced ECAR during basal respiration as well as oligomycin-induced ECAR, an indicator of glycolytic activity (FIG. 10C). Similarly, basal oxygen consumption and uncoupled respiration (the maximal mitochondrial oxygen consumption capacity following the addition of FCCP), which mimics a physiologic "energy demand," was significantly decreased in macrophages isolated from LysM-Cre:MCT$^{f/f}$ mice (FIGS. 10A and 10D). Importantly, macrophages from LysM-Cre:MCT$^{f/f}$ mice have significantly reduced spared respiratory capacity (SRC) (FIG. 10E), which is defined as the difference between maximal and basal respiration, indicating reduced capacity to respond properly to increased energy demand. As would be expected, the overall ATP production for macrophages isolated from LysM-Cre:MCT$^{f/f}$ mice was reduced (FIG. 10F). Interestingly, the percentage of ATP produced from glycolysis (55.8% MCT$^{f/f}$ versus 62.4% for LysM-Cre:MCT$^{f/f}$) and oxidative metabolism (44.2% MCT$^{f/f}$ versus 37.6% for LysM-Cre:MCT$^{f/f}$) was unaltered (2-way ANOVA, genotype factor ns). These findings demonstrate that MCT1 ablation in macrophages impairs both glycolytic and mitochondrial functions, reduces ATP production, and worsens metabolic adaptability to tackle stress stimuli and/or high metabolic demands.

Real-time extracellular acidification and oxygen consumption were measured in peritoneal exudate macrophages isolated from mice of both genotypes with the Seahorse extracellular flux analyzer. The ECAR of macrophages was compared between LysM-Cre:MCT1$^{f/f}$ and littermate control during basal condition and following oligomycin treatment. The OCR of macrophages was compared between LysM-Cre:MCT1$^{f/f}$ and littermate control during basal respiration and FCCP-induced maximal respiration. Spare respiratory capacity (SRC) of macrophages was calculated as the difference between maximal respiration and basal respiration. Total ATP generated by oxidative metabolism and glycolysis was calculated for macrophages isolated from LysM-Cre:MCT1$^{f/f}$ and littermate control mice. Mean±SEM, n=10 per group, p<0.01; *p<0.001; two-way ANOVA with Bonferroni's multiple comparisons test for (c) and (d); unpaired t test for (e, f).

Example 5

Role of MCT1 on Macrophage Phenotype and Phagocytosis

The impaired intracellular metabolism and worsened metabolic adaptability of macrophages due to MCT1 ablation led to the investigation of the role of MCT1 in determining macrophage phenotypes and capacity for phagocytosis. Reducing MCT1 likely contributes to the induction of the M1 phenotype since macrophages isolated from control mice exposed to M1 phenotype inducer for 3 hours had significantly reduced expression of MCT1, while exposure to M2 phenotype inducer led to an insignificant trend toward increased MCT1 expression (FIGS. 11A and 11B). MCT1 mRNA expression was assessed by real-time RT-PCR in peritoneal exudate macrophage cultures prepared from wild-type mice (control mice; MCT1$^{f/f}$) treated with M1-phenotype inducer mixture [LPS (100 ng/ml) plus IFN-γ (50 U/ml)] or M2-phenotype inducer [IL-4 (10 ng/ml)] for 3 h. Levels of mRNAs are depicted as fold change compared with untreated control macrophage cultures normalized to their corresponding GAPDH mRNA levels. Mean±SEM, n=3 per group, *p<0.05; ns=not significant, unpaired t test.

Figure 10I:
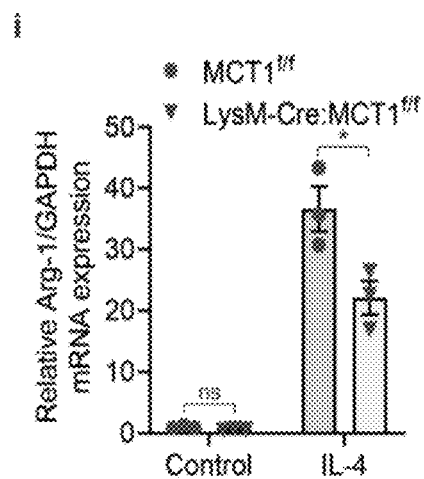

The importance of MCT1 for determining macrophage phenotype was confirmed in macrophage cultures prepared from LysM-Cre:MCT$^{f/f}$ and MCT$^{f/f}$ mice. These cultured macrophages were challenged with either LPS plus IFN-γ or IL-4, well-known inducers of M1 and M2 phenotypes, respectively, for 3 hours and assessed for the expression of M1- or M2-related genes. Interestingly, the mRNA levels of M1-related genes, IL-1β and IL-6, which were similar at basal condition, were significantly increased in macrophages isolated from LysM-Cre:MCT$^{f/f}$ compared to MCT$^{f/f}$ mice after stimulation with LPS plus IFN-γ (FIGS. 10G and 10H). In contrast, the expression of M2-related gene Arg-1, which was also similar at basal condition, was lower in macrophages isolated from LysM-Cre:MCT$^{f/f}$ compared to MCT$^{f/f}$ mice after stimulation with IL-4 (FIG. 10I). Other genes that have been associated with specific macrophage phenotypes (i.e., M1-related gene TNF-α and M2-related gene Ym-1) were independent of MCT1 expression after this acute stimulation with M1 and M2 phenotype inducers (FIGS. 12A and 12B). Peritoneal exudate macrophage cultures prepared from LysM-Cre:MCT1$^{f/f}$ and littermate control mice were treated with M1-phenotype inducer mixture [LPS (100 ng/ml) plus IFN-γ (50 U/ml)] for 3 h. The mRNA levels of M1-related gene TNF-α were assessed by real-time RT-PCR. Similarly, peritoneal exudate macrophage cultures prepared from LysM-Cre:MCT1$^{f/f}$ and littermate control mice were treated with M2-phenotype inducer [IL-4 (10 ng/ml)] for 3 h, and the mRNA levels of M2-related gene Ym-1 were assessed by real-time RT-PCR. Levels of mRNAs are depicted as fold change compared with untreated macrophage cultures isolated from control mice (MCT1$^{f/f}$) normalized to their corresponding GAPDH mRNA levels. Mean±SEM, n=3 per group, ns=not significant, two-way ANOVA with Bonferroni's multiple comparisons test.

Peritoneal exudate macrophage cultures prepared from LysM-Cre:MCT1$^{f/f}$ and littermate control mice were treated with M1-phenotype inducing mixture [LPS (100 ng/ml) plus IFN-γ (50 U/ml)] for 3 hours. The mRNA levels of M1-related genes IL-1β and IL-6 were assessed by real-time RT-PCR. Similarly, peritoneal exudate macrophage cultures prepared from LysM-Cre:MCT1$^{f/f}$ and littermate control mice were treated with M2-phenotype inducer [IL-4 (10 ng/ml)] for 3 hours, and the mRNA levels of M2-related gene Arg-1 was assessed by real-time RT-PCR. Levels of mRNAs are depicted as fold change compared with untreated macrophage cultures isolated from control mice (MCT1$^{f/f}$) normalized to their corresponding GAPDH mRNA levels. Mean±SEM, n=3 per group, *p<0.05; ***p<0.001; ns=not significant, two-way ANOVA with Bonferroni's multiple comparisons test.

Figure 10J:
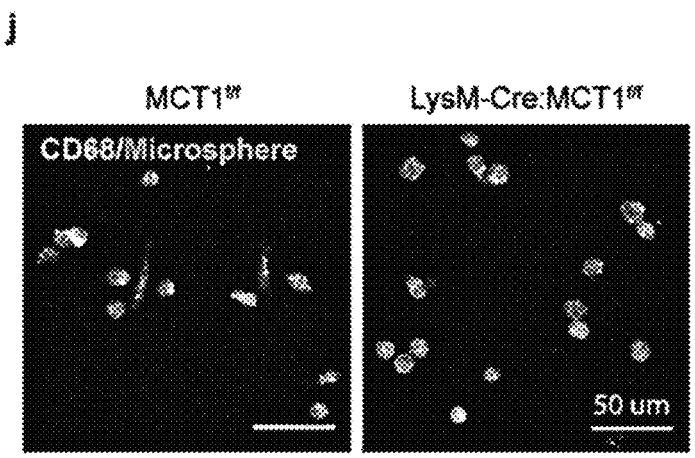
Figure 10K:
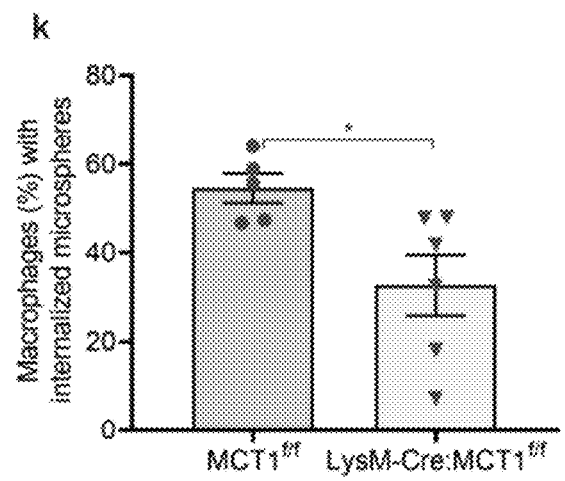

A critical function of macrophages in nerve regeneration is to phagocytose axonal and myelin debris. Thus, the impact of MCT1 deficiency on the phagocytic activity of macrophages at basal condition was examined. It was found that macrophages isolated from LysM-Cre:MCT$^{f/f}$ mice have significantly lower phagocytic capacity than the macrophages isolated from littermate control mice (FIGS. 10J and 10K). Peritoneal exudate macrophage cultures (30,000 cells per well for the 8-well chamber slide) prepared from LysM-Cre:MCT1$^{f/f}$ and littermate control mice were incubated with fluorescent microspheres for 2 hours, visualized by immunostaining with anti-CD68 antibody, and were imaged by confocal microscopy; representative images from at least five independent experiments to determine internalization by counting the number of cells with internalized fluorescent microspheres were analyzed presented as a percentage. Mean±SEM, n=5-7 per group, *p<0.05; unpaired t test. Calibration bar: 50 μm. These findings suggest that MCT1 is an important determinant of macrophage phenotype during inflammation, both for shaping the cytokine microenvironment and contributing to the critical function of macrophage phagocytosis.

Example 6

Impact of Adoptive Cell Transfer of Macrophages with Intact MCT1 on Nerve Regeneration Adoptive cell transfer of chimeric antigen receptor-modified T cells (e.g., CAR-T cells) is well established for treatment of hematologic malignancies and is being considered for solid tumors, infections, and autoimmune conditions, as well. To date, adoptive cell transfer of macrophages has proven safe, but not yet effective, in treating cancer patients. Adoptive cell transfer of macrophages following peripheral nerve injury has never previously been reported.

Figure 13A:
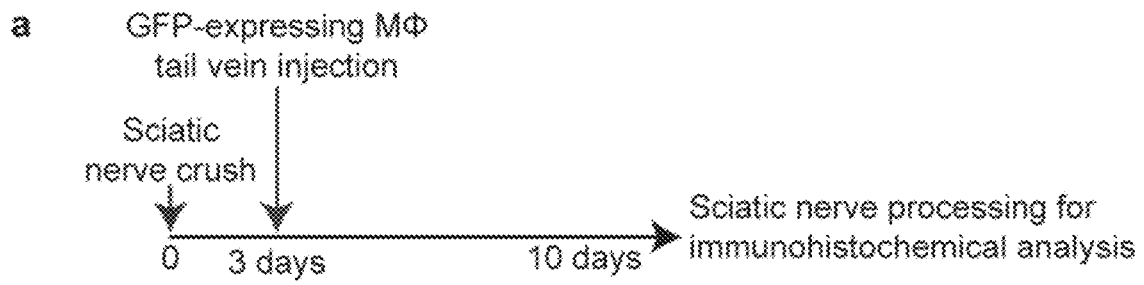
FIGS. 13A-13F illustrate the effect of the adoptive cell transfer of macrophages with intact MCT1 on nerve regeneration in macrophage-specific MCT1 deficient mice.
Figure 13B:
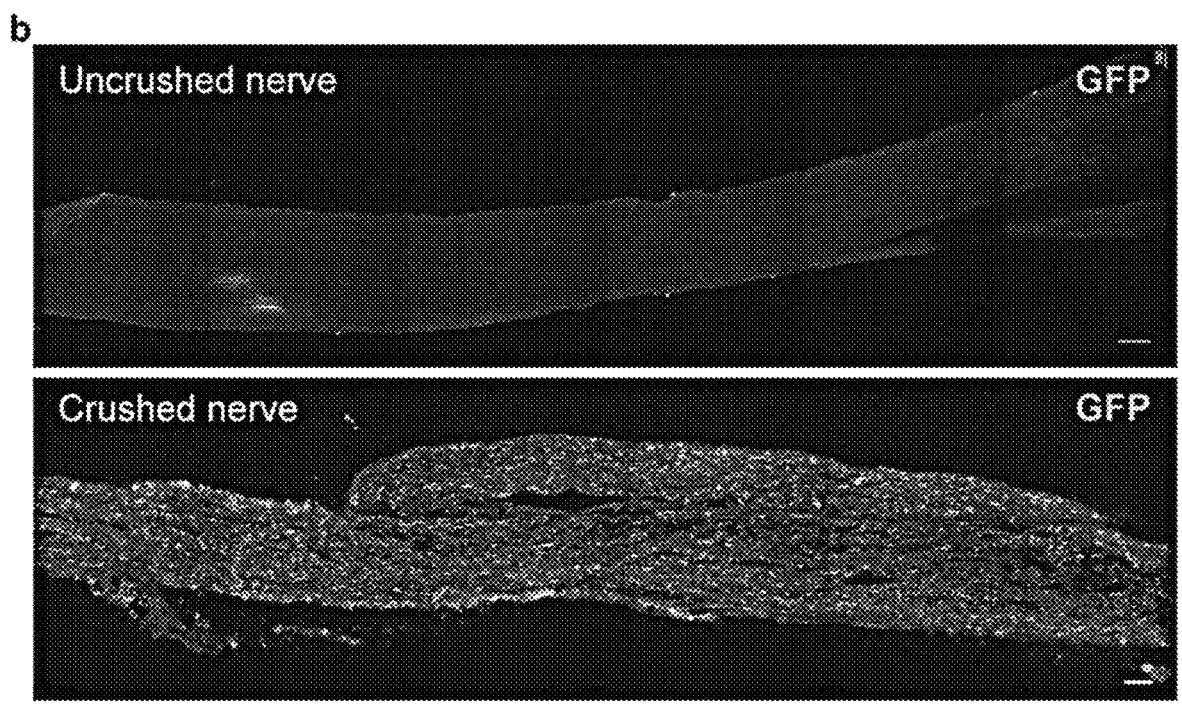
Figure 13C:
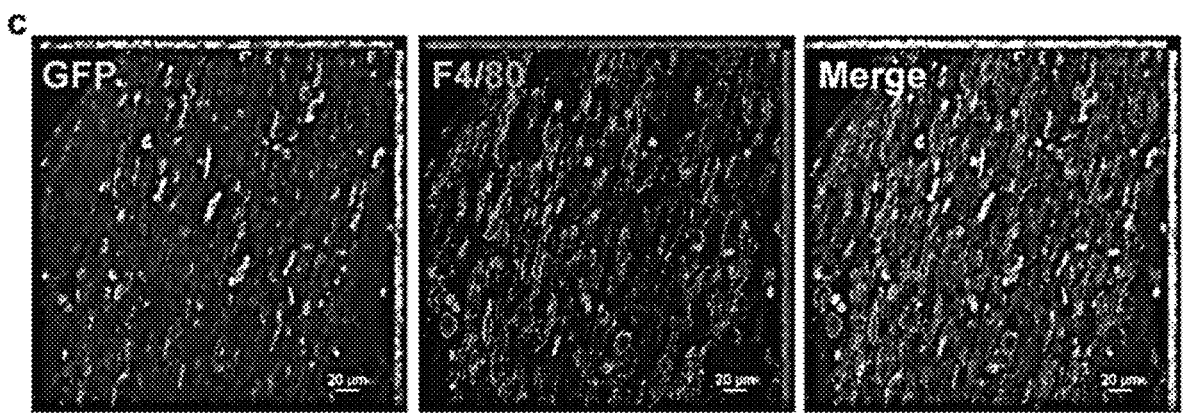

First, it was confirmed that macrophages injected intravenously targeted crushed sciatic nerve. Bone marrow-derived macrophages (BMDMs) obtained from Bl6:LysM-Cre:RosaYFP mice were injected into the tail-vein of control Bl6 mice 3 days following unilateral sciatic nerve crush. BMDMs, which express macrophage marker F4/80, targeted and survived in injured, but not uninjured, sciatic nerves (FIGS. 13A, 13B and 13C). Both donors and recipients of same background (C57BL/6J) were used in these studies. BMDMs target the injured, but not the uninjured sciatic nerve following the intravenous injection. Nerve samples harvested 7 days following tail vein injection showed that many of the GFP-positive cells express F4/80, a specific macrophage marker, as can be seen in merged image. Images are representative confocal micrographs of three independent experiments. Calibration bar: 20 μm.

Figure 13D:
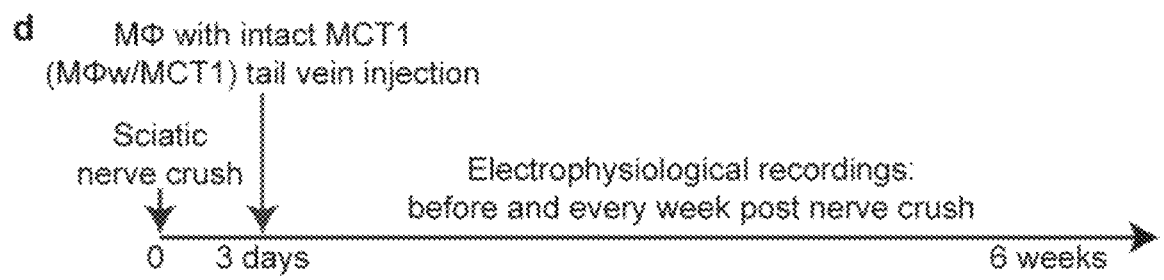
Figure 13E:
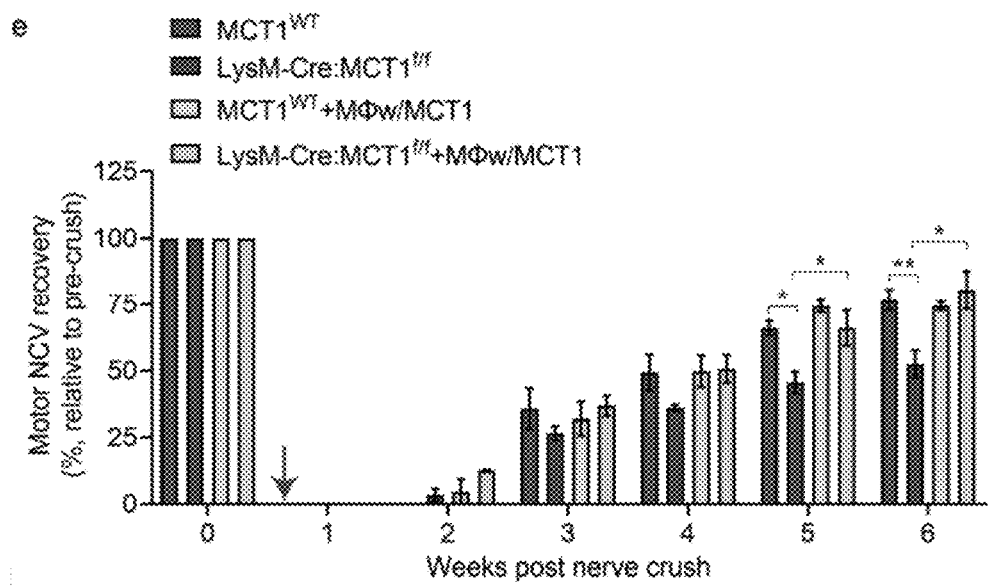
Figure 13F:
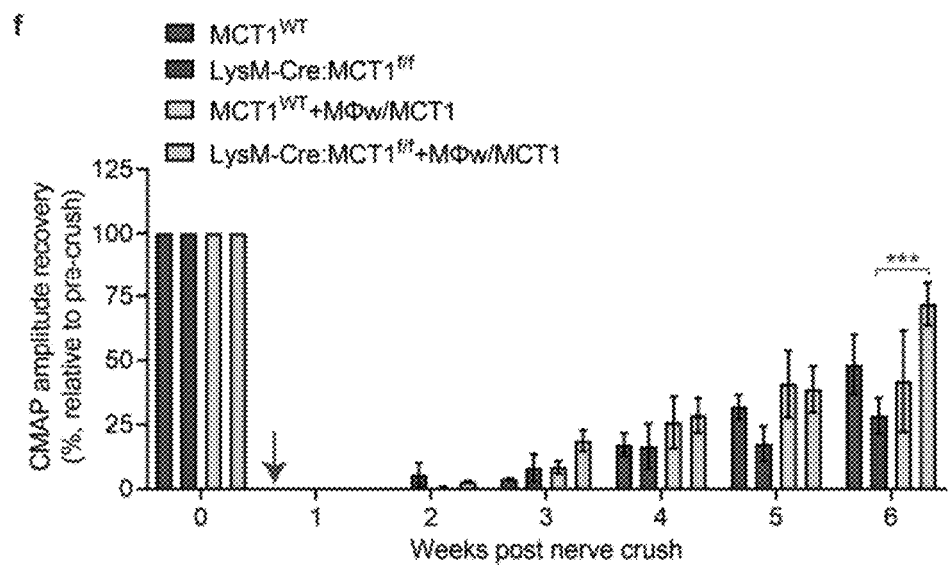

BMDMs were injected 3 days following sciatic nerve crush because this is the timepoint when circulating macrophages infiltrate the injured nerve. To measure the impact of adoptive cell transfer of macrophages on nerve regeneration, MCT1$^{f/f}$ mice were backcrossed for 8 generations to C57Bl/6J mice and mated with B6:LysM-Cre mice to produce macrophage-specific MCT1 knockout mice on C57BL/6J background (B6:LysM-Cre: MCT1$^{f/f}$). These congenic knockout mice did not reveal any sign of peripheral neuropathy at all age points relevant to this study (data not shown). Following sciatic nerve crush, B6:LysM-Cre: MCT1$^{f/f}$ mice showed a similar impairment in nerve regeneration, as measured by electrophysiology (FIGS. 13D, 13E and 13F), as the mixed background LysM-Cre: MCT1$^{f/f}$ mice investigated previously (FIG. 1). Additionally, and more importantly, tail-vein injection of BMDMs derived from C57BL/6J wild-type mice 3 days following sciatic nerve crush led to complete recovery of the impaired regeneration in B6:LysM-Cre:MCT 1$^{f/f}$ mice, while having no impact on C57Bl6 wild-type mice. These results confirm that the ablation of MCT1 within macrophages was responsible for the impaired regeneration in LysM-Cre:MCT 1$^{f/f}$ mice. They also suggest that adoptive cell transfer of macrophages may be a useful strategy for treating nerve injuries in patients.

Both donors and recipients of same background (C57BL/6J) were used in these studies. Motor nerve conduction velocity (NCV) and compound muscle action potential (CMAP) amplitude recovery of nerve after injury were evaluated in the following groups: C57Bl6 wild-type mice (MCT1$^{WT}$), C57Bl6 macrophage-selective MCT1 null mice (LysM-Cre:MCT1$^{f/f}$), MCT1$^{WT}$ mice following tail-vein injection of BMDMs isolated from MCT1$^{WT}$ mice (MCT1WT+ MOw/MCT1), and LysM-Cre:MCT1$^{f/f}$ mice following tail-vein injection of BMDMs isolated from MCT1$^{WT}$ mice (LysM-Cre:MCT1$^{f/f}$+MOw/MCT1). Recoveries are presented as percent relative to pre-crush condi-

Example 7

Impact of MCT1 Overexpression in Macrophage on Peripheral Nerve Regeneration

Figure 14A:
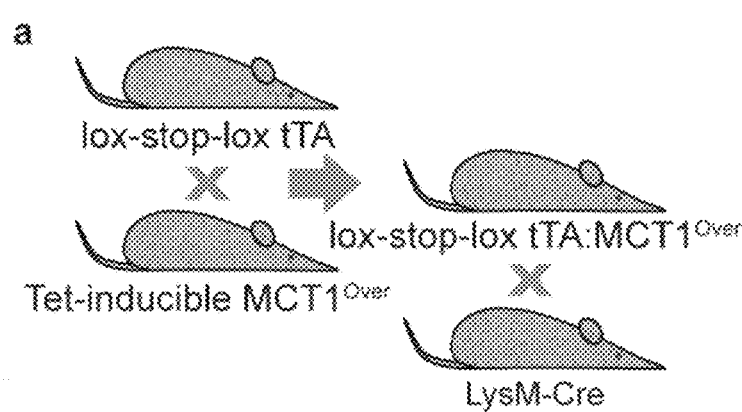
Figure 14B:
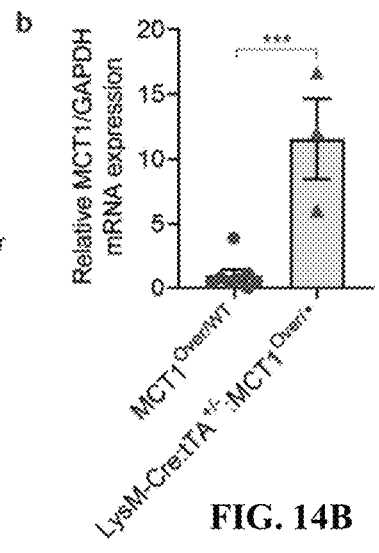

The experiments in transgenic mice and macrophage cultures with ablation of macrophage MCT1 provided knowledge of the specific role this transporter plays in macrophage cell biology and nerve regeneration. To explore the translational significance of these findings, peripheral nerve regeneration was tested in two different transgenic mice with upregulated expression of MCT1 only in macrophages. In the first mouse, tet-inducible MCT1 overexpressor mice (MCT1$^{Over/WT}$), were mated with ROSA:LNL:tTA (tTA; from Jackson Laboratories) and LysM-Cre mice to produce LysM-Cre:tTA$^{+/-}$:MCT1$^{Over/+}$ and littermate control (MCT1$^{Over/WT}$) mice (FIG. 14A). Macrophages isolated from these mice have increased MCT1 expression compared to littermate controls (FIG. 14B). Macrophage specific MCT1 overexpression was confirmed by evaluating the expression of MCT1 mRNA in peritoneal exudate macrophage cultures prepared from LysM-Cre:tTA$^{+/-}$:MCT1$^{Over/+}$ and control littermate mice by real-time RT-PCR. Levels of mRNA were depicted as fold change compared with macrophage cultures isolated from control mice normalized to their corresponding GAPDH mRNA levels. Mean±SEM, n=3-8 per group, ***p<0.001; unpaired t test.

Figure 14C:
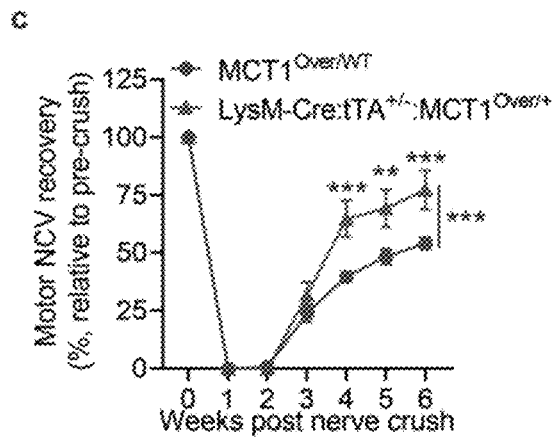
Figure 14D:
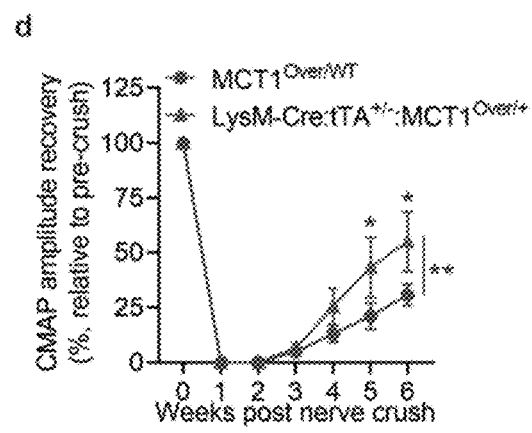
Figure 14E:
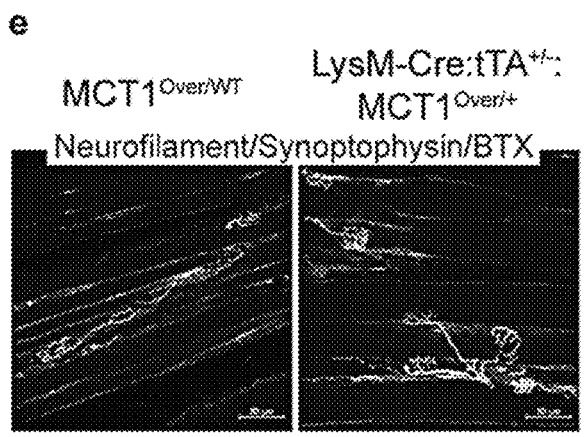
Figure 14F:
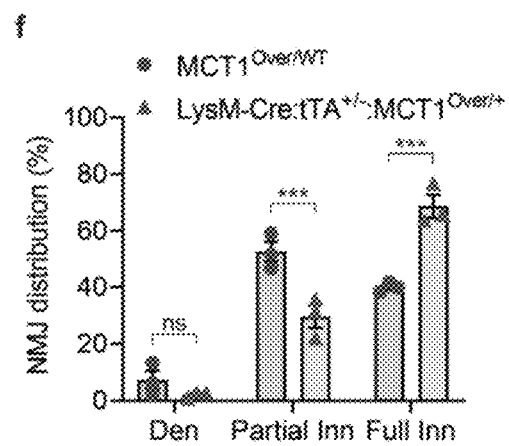

LysM-Cre:tTA$^{+/-}$:MCT1$^{Over/+}$ mice have improved nerve regeneration following crush compared to MCT1$^{Over/+}$ mice, as measured by electrophysiology (FIGS. 14C and 14D) and neuromuscular junction (NMJ) reinnervation (FIGS. 14E and 14F). (c-d) Motor nerve conduction velocity (NCV) recovery and compound muscle action potential (CMAP) amplitude recovery of nerve after injury were presented as percent relative to pre-crush conditions. Mean±SEM, n=8 (for MCT1$^{Over/WT}$ group) or 6 (for LysM-Cre:tTA$^{+/-}$:MCT1$^{Over/WT}$ group), *p<0.05, p<0.01, *p<0.001; two-way ANOVA with Bonferroni's multiple comparisons test. Representative photomicrographs of fluorescently labelled neuromuscular junctions (NMJs) in gastrocnemius muscles 6 weeks after crush were selected from muscles stained with α-Bungarotoxin (BTX, Alexa Fluor™ 555 conjugate) to visualize AChRs, anti-SMI312 antibody to visualize neurofilaments, and anti-synaptophysin antibody to visualize nerve terminals. Calibration bar: 50 µm. Increased fully reinnervated and decreased denervated and/or partially reinnervated AChR clusters in mice with macrophage-specific MCT1 overexpression were compared with their littermate controls 6 weeks after crush. Mean±SEM, n=3-4 per group, *p<0.05; ns=not significant; two-way ANOVA with Bonferroni's multiple comparisons test.

These results were confirmed in a second transgenic line, in which MCT1$^{Over/WT}$ mice were mated with CD68-rtTA (FIG. 14G). Transgenic mice with macrophage specific, doxycycline-inducible MCT1 expression, (CD68-rtTA:MCT1$^{Over/+}$) were produced by using CD68-rtTa mice that are a Tet-On tool that allows conditional, doxycycline-inducible expression of MCT1 in mature macrophages. With doxycycline treatment, these mice also showed upregulation of MCT1 in macrophages and improved nerve regeneration by electrophysiology and NMJ reinnervation (FIGS. 14H, 14I, 14J, 14K and 14L). These experiments demonstrated that macrophage MCT1 is not only necessary for nerve regeneration, but that upregulation of this transporter can accelerate nerve regeneration and may potentially be a target for treatment of nerve injuries in patients. Macrophage specific MCT1 overexpression was confirmed by evaluating the expression of MCT1 mRNA in peritoneal exudate macrophage cultures prepared from CD68-rtTA:MCT 1Over/+ and control littermate mice by real-time RT-PCR. Levels of mRNA were depicted as fold change compared with macrophage cultures isolated from control mice normalized to their corresponding GAPDH mRNA levels. Mean±SEM, n=4-5 per group, ***p<0.001; unpaired t test. Motor nerve conduction velocity (NCV) recovery and CMAP amplitude recovery of nerve before and after injury were presented as percent relative to pre-crush conditions. Mean±SEM, n=9 (for MCT1$^{Over/WT}$ group) or 5 (for CD68-rtTA:MCT1Over/+ group), *p<0.05, ***p<0.001; two-way ANOVA with Bonferroni's multiple comparisons test. Representative photomicrographs of fluorescently labelled NMJs in gastrocnemius muscles 6 weeks after crush were selected from muscles stained with α-Bungarotoxin (BTX, Alexa Fluor™ 555 conjugate) to visualize AChRs, anti-SMI312 antibody to visualize neurofilaments, and anti-synaptophysin antibody to visualize nerve terminals. Calibration bar: 50 µm. Increased fully reinnervated and decreased denervated and/or partially reinnervated AChR clusters in mice with macrophage-specific MCT1 overexpression were compared with their littermate controls 6 weeks after crush. Mean±SEM, n=3 per group, *p<0.05, ***p<0.001; ns=not significant; two-way ANOVA with Bonferroni's multiple comparisons test.

Example 7

Discussion

Despite having the capacity to regenerate, the functional recovery following peripheral nerve injury is slow and often incomplete. Though macrophages have been known to participate in peripheral nerve regeneration and repair for decades, almost nothing is known about the role that intracellular metabolism plays in this function. Several seminal studies published recently indicate that macrophage function, at least in vitro, is dependent on specific alteration of macrophage intracellular metabolism. Combining an analysis of macrophage intracellular metabolism and immune responses, along with its impact on an experimental model of peripheral nerve regeneration, the results presented in Examples 2-6 show that MCT1 is an important contributor to macrophage cellular function and their biologic role in recovery from nerve injury.

The distinct functional states of macrophages depend on their intracellular metabolic program, which is governed by the cross-talk between intracellular signaling cascades, metabolic mediators, and their metabolites. Emerging evidence suggests that immune effector functions, particularly cytokine production, are directly coupled to specific changes in cellular metabolism. Macrophages stimulated in vitro to a pro-inflammatory state have blockade of the TCA cycle at two sites, causing a reduction of oxidative metabolism and simultaneous upregulation of genes that mediate the pentose phosphate pathway, glycolysis, and lactate production in order to produce sufficient ATP for cell survival. In contrast, macrophages stimulated in vitro to a pro-regenerative state upregulate glycolysis and fatty acid oxidation to support an activated TCA cycle. The results presented in Examples 2-6 suggest that MCT1 is an important mediator of macrophage intracellular metabolism and function. Both glycolysis and mitochondrial metabolism are impaired in macrophages with conditionally ablated MCT1. Additionally, macrophages without MCT1 have increased expression of pro-inflammatory and decreased expression of pro-regenerative cytokines. This was observed both in macrophages isolated in vitro and in peripheral nerve isolated following nerve injury. Finally, ablation of MCT1 from macrophages reduces their phagocytic capacity. Given the recently identified role of MCT1 and lactate in macrophage efferocytosis, which is the engulfment of dead or injured cells, the phagocytosis of axons and myelin may also similarly be dependent on this transporter. Interestingly, not all functions of macrophages are impacted by loss of MCT1, as macrophage survival, migration, and infiltration of the injured nerve is not altered in LysM-Cre: MCT1$^{f/f}$ mice. The disruption of these critical functions of macrophages, particularly cytokine production and phagocytosis, likely contribute to the disruption of peripheral nerve regeneration observed in LysM-Cre: MCT1$^{f/f}$ mice.

To date, there are no approved therapies for accelerating nerve regeneration and patients with proximal nerve injuries, from either trauma or other conditions (e.g., Parsonage Turner syndrome, nerve tumors, or severe auto-immune or toxic neuropathies), have little hope of functional improvement since unaided peripheral nerve regeneration is slow and incomplete. Besides evaluating the impact of ablating MCT1 from macrophages in vitro and in vivo, the present results demonstrate for the first time that manipulating macrophage metabolism can actually accelerate peripheral nerve regeneration. Using two different conditional transgenic mice that upregulate MCT1 only in macrophages, acceleration of nerve regeneration was demonstrated, with clear improvements in both CMAP amplitude and NMJ reinnervation, which are electrophysiologic and histologic markers for successful axon regeneration, respectively. These studies suggest that upregulation of macrophage MCT1, or perhaps other metabolic targets, is an exciting pathway that could potentially be manipulated in patients to treat peripheral nerve injuries.

Thus far, virtually all of the efforts to improve nerve regeneration have focused on neurons and Schwann cells. Though some genes have been found to accelerate nerve regeneration, described as regeneration-associated genes or RAGs, these genes have not been clinically useful targets due to being known oncogenes. In contrast to these studies, MCT1 is not an oncogene, and the focus on macrophages is novel. Unlike neurons and Schwann cell, for which there are no easy techniques for effective transplantation, macrophages are a cell type that can be safely transfused into patients. In fact, it was demonstrated here for the first time the feasibility of macrophage adoptive cell transfer for the treatment of peripheral nerve injuries. Given this, it is not far-fetched to imagine treating acute peripheral nerve injuries in patients with infusion of macrophages that have been isolated from patients and modified to upregulate MCT1 or other targets to alter their cellular metabolism and function. The field of immunometabolism is very exciting and has thus far primarily been focused on cancer therapeutics. The experiments detailed here open up the field to other disciplines and may represent the first of many medical conditions being amenable to treatment with metabolically altered macrophages.

Indeed, using macrophage-selective MCT1 ablation or upregulation mice and adoptive cell transfer of macrophages, a crucial role for MCT1 in determining macrophage intracellular metabolism and immune functions in the peripheral nerve response to injury was identified. It was found that macrophage-specific MCT1 deletion impaired axon regeneration by reducing the phagocytic capacity of macrophages and inhibiting the formation of pro-regenerative microenvironment in injured nerves. Importantly, the adoptive cell transfer of macrophages with intact MCT1 was able to completely ameliorate the impaired peripheral nerve regeneration in mice with macrophage-selective ablation of MCT1. Of particular clinical interest, it was observed that MCT1 upregulation in macrophages accelerates peripheral nerve regeneration following injury, which may be a promising pathway for treating peripheral nerve injuries, a common clinical problem worldwide with no therapeutic options.

Example 8

Ex Vivo Upregulation of MCT1 in Cells

In order to further evaluate how the results observed in Examples 1-7 could be translated into patients having a nerve injury, ex vivo upregulation of MCT1 in cells was performed. Cells were isolated from a sample collected from a donor, and infected with a lentivirus encoding a GFP protein (as a control) or with a lentivirus encoding an MCT1 protein.

Figure 15:
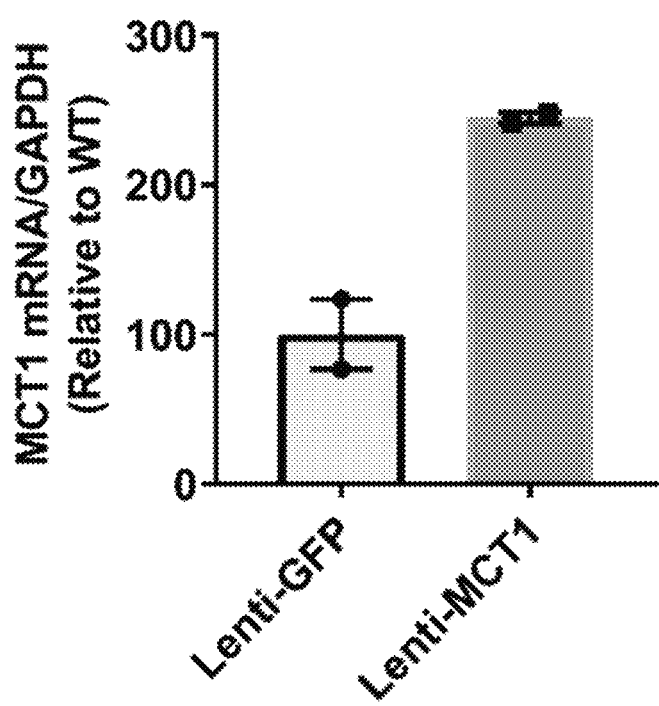
FIG. 15 is a bar graph illustrating the relative MCT1 expression in bone marrow-derived macrophages after infection with a lentivirus encoding MCT1.

The expression of MCT1 in the cells was assessed, and evaluated relatively to GAPDH. As illustrated in FIG. 15, MCT1 expression was upregulated ex vivo in cells after infecting cells with a lentivirus encoding an MCT1 protein. This results suggested that MCT1 can be upregulated ex vivo in macrophages isolated from patients, before being re-administered to the patient after a nerve injury occurred.

Although the invention has been described with reference to the above examples, it will be understood that modifications and variations are encompassed within the spirit and scope of the invention. Accordingly, the invention is limited only by the following claims.

Embodiments of the present invention include the following:

1. A method of increasing macrophage nerve regeneration activity comprising upregulating expression of an MCT1 gene in the macrophage, thereby increasing macrophage nerve regeneration activity.

2. The method of claim 1, wherein upregulating the expression of the MCT1 gene comprises contacting the macrophage with a vector encoding an MCT1 gene or with a small molecule agonist of MCT1, thereby increasing the expression of MCT1 gene in the macrophage.

3. The method of claim 2, wherein the vector is a plasmid or a viral vector.

4. The method of claim 3, wherein the viral vector is a lentiviral vector.

5. The method of claim 1, wherein the macrophage nerve regeneration activity is selected from the group consisting of macrophage glycolytic and mitochondrial activities, phagocytosis activity, production of pro-regenerative cytokines, production of pro-inflammatory cytokines, modulation of nerve conduction velocity (NCV), modulation of compound muscle action potential (CMAP), modulation of neuromuscular junction (NMJ) reinnervation, and combinations thereof.

6. The method of claim 5, wherein the glycolytic and mitochondrial activity is selected from lactate uptake, extracellular acidification rate (ECAR), oxygen consumption rate (OCR), spared respiratory capacity (SRC) and/or ATP production.

7. The method of claim 5, wherein phagocytosis activity comprises axonal phagocytosis and myelin debris phagocytosis.

8. The method of claim 5, wherein the pro-regenerative cytokines are selected from the group consisting of IL-10, IL-21R, and TGF-β.

9. The method of claim 5, wherein the pro-inflammatory cytokines are selected from the group consisting of IL-1β, TNF-α, IL-6, IL-12, IL-15 and IL-23.

10. A method of inducing nerve regeneration of an injured nerve in a subject comprising:
   administering to the subject a macrophage composition, wherein the macrophage composition comprises:
   (a) a macrophage having increased nerve regenerating activity as compared to a reference macrophage; and
   (b) a pharmaceutically acceptable carrier,
   thereby inducing nerve regeneration of an injured nerve in the subject.

11. The method of claim 10, wherein the macrophage composition is produced by:
   (a) isolating a macrophage from the subject; and
   (b) contacting the macrophage with a vector comprising a polynucleotide encoding MCT1 or with a small molecule agonist of MCT1 to produce a macrophage having increased nerve regenerating activity.

12. The method of claim 10, wherein the reference macrophage is a macrophage that has not been contacted with a vector comprising a polynucleotide encoding MCT1 or a small molecule agonist of MCT1.

13. The method of claim 11, wherein the vector is a plasmid or a viral vector.

14. The method of claim 13, wherein the viral vector is a lentiviral vector.

15. The method of claim 11, wherein the macrophage is from a blood or bone marrow sample.

16. The method of claim 10, wherein the macrophage is an anti-inflammatory, pro-regenerative M2-macrophage.

17. The method of claim 10, wherein the macrophage has increased glycolytic and mitochondrial functions as compared to a reference macrophage that does not have an increased MCT1 gene expression.

18. The method of claim 10, wherein the macrophage has an increased phagocytosis function as compared to a reference macrophage that does not have an increased MCT1 gene expression.

19. The method of claim 18, wherein the increased phagocytosis function comprises an increased axonal phagocytosis and an increased myelin debris phagocytosis.

20. The method of claim 18, wherein the increased phagocytosis function induces an increase in myelin thickness of a regenerated nerve, an increase in a number of myelinated axons in the regenerated nerve, and a decrease in a g ratio of the regenerated nerve.

21. The method of claim 10, wherein the macrophage has an increased production of pro-regenerative cytokines as compared to a reference macrophage that does not have an increased MCT1 gene expression.

22. The method of claim 10, wherein the macrophage has a decreased production of pro-inflammatory cytokines as compared to a reference macrophage that does not have an increased MCT1 gene expression.

23. The method of claim 10, wherein the injured nerve results from a trauma, inflammation, non-traumatic injury, or exposure to a toxin.

24. The method of claim 23, wherein the injured nerve results from Parsonage Turner syndrome, a nerve tumor, an auto-immune neuropathy, diabetes, or a toxic neuropathy.

25. The method of claim 10, wherein inducing nerve regeneration in the subject comprises increasing neuroimmune interaction at a nerve injury site.

26. The method of claim 10, wherein inducing nerve regeneration in the subject comprises increasing nerve conduction velocity (NCV) after a nerve injury.

27. The method of claim 10, wherein inducing nerve regeneration in the subject comprises increasing compound muscle action potential (CMAP) after a nerve injury.

28. The method of claim 10, wherein inducing nerve regeneration in the subject comprises increasing neuromuscular junction (NMJ) reinnervation after a nerve injury.

29. The method of claim 28, wherein increasing neuromuscular junction reinnervation after nerve injury comprises increasing an amount of full NMJ reinnervation and decreasing an amount of denervated or partially reinnervated NMJ in an injured muscle.

30. The method of claim 10, wherein inducing nerve regeneration in the subject comprises accelerating nerve regeneration in the subject after a nerve injury.

31. The method of claim 10, wherein administering a macrophage composition comprises intravenous, intraperitoneal and intraarterial administrations.

32. The method of claim 10, wherein administering a macrophage composition comprises administering the composition in close proximity to the injured nerve.

33. A vector comprising a polynucleotide encoding MCT1 operably linked to a regulatory sequence.

34. The vector of claim 33, wherein the vector is a plasmid or a viral vector.

35. The vector of claim 34, wherein the viral vector is a lentiviral vector, an adenoviral vector or an adeno-associated viral (AAV) vector.

36. An isolated macrophage comprising the vector of claim 33.

37. A macrophage cell composition comprising the isolated macrophage of claim 36 and a pharmaceutically acceptable carrier.

REFERENCES

1. Conforti, L., Gilley, J. & Coleman, M. P. Wallerian degeneration: an emerging axon death pathway linking injury and disease. *Nat Rev Neurosci* 15, 394-409 (2014).
2. Catlin, A. L. & Lloyd, A. C. The multicellular complexity of peripheral nerve regeneration. *Curr Opin Neurobiol* 39, 38-46 (2016).
3. Stierli, S., Imperatore, V. & Lloyd, A. C. Schwann cell plasticity-roles in tissue homeostasis, regeneration, and disease. *Glia* (2019).
4. Godzik, K. & Coleman, M. P. The axon-protective WLD (S) protein partially rescues mitochondrial respiration and glycolysis after axonal injury. *J Mol Neurosci* 55, 865-871 (2015).
5. Geisler, S., et al. Gene therapy targeting SARM1 blocks pathological axon degeneration in mice. *J Exp Med* 216, 294-303 (2019).
6. Scheib, J. & Hoke, A. Advances in peripheral nerve regeneration. *Nat Rev Neurol* 9, 668-676 (2013).
7. Gaudet, A. D., Popovich, P. G. & Ramer, M. S. Wallerian degeneration: gaining perspective on inflammatory events after peripheral nerve injury. *J Neuroinflammation* 8, 110 (2011).
8. Wujek, J. R. & Lasek, R. J. Correlation of axonal regeneration and slow component B in two branches of a single axon. *J Neurosci* 3, 243-251 (1983).
9. Chen, P., Piao, X. & Bonaldo, P. Role of macrophages in Wallerian degeneration and axonal regeneration after peripheral nerve injury. *Acta Neuropathol* 130, 605-618 (2015).

10. Bruck, W. The role of macrophages in Wallerian degeneration. *Brain Pathol* 7, 741-752 (1997).
11. Stratton, J. A., et al. Macrophages Regulate Schwann Cell Maturation after Nerve Injury. *Cell Rep* 24, 2561-2572 e2566 (2018).
12. DeFrancesco-Lisowitz, A., Lindborg, J. A., Niemi, J. P. & Zigmond, R. E. The neuroimmunology of degeneration and regeneration in the peripheral nervous system. *Neuroscience* 302, 174-203 (2015).
13. Mokarram, N. & Bellamkonda, R. V. A perspective on immunomodulation and tissue repair. *Ann Biomed Eng* 42, 338-351 (2014).
14. Kolter, J., et al. A Subset of Skin Macrophages Contributes to the Surveillance and Regeneration of Local Nerves. *Immunity* 50, 1482-1497 e1487 (2019).
15. La Fleur, M., Underwood, J. L., Rappolee, D. A. & Werb, Z. Basement membrane and repair of injury to peripheral nerve: defining a potential role for macrophages, matrix metalloproteinases, and tissue inhibitor of metalloproteinases-1. *J Exp Med* 184, 23112326 (1996).
16. Liu, P., et al. Role of macrophages in peripheral nerve injury and repair. *Neural Regen Res* 14, 1335-1342 (2019).
17. Tomlinson, J. E., Zygelyte, E., Grenier, J. K., Edwards, M. G. & Cheetham, J. Temporal changes in macrophage phenotype after peripheral nerve injury. *J Neuroinflammation* 15, 185 (2018).
18. Siqueira Mietto, B., et al. Role of IL-10 in Resolution of Inflammation and Functional Recovery after Peripheral Nerve Injury. *J Neurosci* 35, 16431-16442 (2015).
19. Zigmond, R. E. & Echevarria, F. D. Macrophage biology in the peripheral nervous system after injury. *Prog Neurobiol* 173, 102-121 (2019).
20. O'Neill, L. A., Kishton, R. J. & Rathmell, J. A guide to immunometabolism for immunologists. *Nat Rev Immunol* 16, 553-565 (2016).
21. Jha, A. K., et al. Network integration of parallel metabolic and transcriptional data reveals metabolic modules that regulate macrophage polarization. *Immunity* 42, 419-430 (2015).
22. Ouimet, M., et al. MicroRNA-33-dependent regulation of macrophage metabolism directs immune cell polarization in atherosclerosis. *J Clin Invest* 125, 4334-4348 (2015).
23. Netea, M. G., Joosten, L. A., van der Meer, J. W., Kullberg, B. J. & van de Veerdonk, F. L. Immune defence against Candida fungal infections. *Nat Rev Immunol* 15, 630-642 (2015).
24. Langston, P. K., Shibata, M. & Horng, T. Metabolism Supports Macrophage Activation. *Front Immunol* 8, 61 (2017).
25. Diskin, C. & Palsson-McDermott, E. M. Metabolic Modulation in Macrophage Effector Function. *Front Immunol* 9, 270 (2018).
26. Byles, V., et al. The TSC-mTOR pathway regulates macrophage polarization. *Nat Commun* 4, 2834 (2013).
27. Covarrubias, A. J., et al. Akt-mTORC1 signaling regulates Acly to integrate metabolic input to control of macrophage activation. *Elife* 5 (2016).
28. Biswas, S. K. & Mantovani, A. Orchestration of metabolism by macrophages. *Cell Metab* 15, 432-437 (2012).
29. Murray, C. M., et al. Monocarboxylate transporter MCT1 is a target for immunosuppression. *Nat Chem Biol* 1, 371-376 (2005).
30. Ekberg, H., et al. The specific monocarboxylate transporter-1 (MCT-1) inhibitor, AR-C117977, induces donor-specific suppression, reducing acute and chronic allograft rejection in the rat. *Transplantation* 84, 1191-1199 (2007).
31. Haas, R., et al. Lactate Regulates Metabolic and Proinflammatory Circuits in Control of T Cell Migration and Effector Functions. *PLoS Biol* 13, e1002202 (2015).
32. Morrison, B. M., et al. Deficiency in monocarboxylate transporter 1 (MCT1) in mice delays regeneration of peripheral nerves following sciatic nerve crush. *Exp Neurol* 263, 325-338 (2015).
33. Halestrap, A. P. The SLC16 gene family—structure, role and regulation in health and disease. *Mol Aspects Med* 34, 337-349 (2013).
34. Abram, C. L., Roberge, G. L., Hu, Y. & Lowell, C. A. Comparative analysis of the efficiency and specificity of myeloid-Cre deleting strains using ROSA-EYFP reporter mice. *J Immunol Methods* 408, 89-100 (2014).
35. Shi, J., Hua, L., Harmer, D., Li, P. & Ren, G. Cre Driver Mice Targeting Macrophages. *Methods Mol Biol* 1784, 263-275 (2018).
36. Clausen, B. E., Burkhardt, C., Reith, W., Renkawitz, R. & Forster, I. Conditional gene targeting in macrophages and granulocytes using LysMcre mice. *Transgenic Res* 8, 265277 (1999).
37. Merezhinskaya, N., Ogunwuyi, S. A., Mullick, F. G. & Fishbein, W. N. Presence and localization of three lactic acid transporters (MCT1, -2, and -4) in separated human granulocytes, lymphocytes, and monocytes. *J Histochem Cytochem* 52, 1483-1493 (2004).
38. Lindborg, J. A., Mack, M. & Zigmond, R. E. Neutrophils Are Critical for Myelin Removal in a Peripheral Nerve Injury Model of Wallerian Degeneration. *J Neurosci* 37, 1025810277 (2017).
39. Perkins, N. M. & Tracey, D. J. Hyperalgesia due to nerve injury: role of neutrophils. *Neuroscience* 101, 745-757 (2000).
40. Lindborg, J. A., et al. Molecular and cellular identification of the immune response in peripheral ganglia following nerve injury. *J Neuroinflammation* 15, 192 (2018).
41. Sykes, D. B., Scheele, J., Pasillas, M. & Kamps, M. P. Transcriptional profiling during the early differentiation of granulocyte and monocyte progenitors controlled by conditional versions of the E2a-Pbx1 oncoprotein. *Leuk Lymphoma* 44, 1187-1199 (2003).
42. Kim, C. F. & Moalem-Taylor, G. Detailed characterization of neuro-immune responses following neuropathic injury in mice. *Brain Res* 1405, 95-108 (2011).
43. Raes, G., et al. Arginase-1 and Ym 1 are markers for murine, but not human, alternatively activated myeloid cells. *J Immunol* 174, 6561; author reply 6561-6562 (2005).
44. Gill, S., Maus, M. V. & Porter, D. L. Chimeric antigen receptor T cell therapy: 25 years in the making. *Blood Rev* 30, 157-167 (2016).
45. Newick, K., O'Brien, S., Moon, E. & Albelda, S. M. CAR T Cell Therapy for Solid Tumors. *Annu Rev Med* 68, 139-152 (2017).
46. Maldini, C. R., Ellis, G. I. & Riley, J. L. CAR T cells for infection, autoimmunity and allotransplantation. *Nat Rev Immunol* 18, 605-616 (2018).
47. Lee, S., Kivimae, S., Dolor, A. & Szoka, F. C. Macrophage-based cell therapies: The long and winding road. *J Control Release* 240, 527-540 (2016).
48. Choi, J., et al. Use of macrophages to deliver therapeutic and imaging contrast agents to tumors. *Biomaterials* 33, 4195-4203 (2012).

49. Zhao, Y., et al. GDNF-expressing macrophages restore motor functions at a severe late-stage, and produce long-term neuroprotective effects at an early-stage of Parkinson's disease in transgenic Parkin Q311X(A) mice. *J Control Release* 315, 139-149 (2019).
50. Pullen, T. J., et al. Overexpression of monocarboxylate transporter-1 (SLC16A1) in mouse pancreatic beta-cells leads to relative hyperinsulinism during exercise. *Diabetes* 61, 1719-1725 (2012).
51. Lazarov-Spiegler, O., et al. Transplantation of activated macrophages overcomes central nervous system regrowth failure. *FASEB J* 10, 1296-1302 (1996).
52. Brown, M. C., Perry, V. H., Lunn, E. R., Gordon, S. & Heumann, R. Macrophage dependence of peripheral sensory nerve regeneration: possible involvement of nerve growth factor. *Neuron* 6, 359-370 (1991).
53. Ip, W. K. E., Hoshi, N., Shouval, D. S., Snapper, S. & Medzhitov, R. Anti-inflammatory effect of IL-10 mediated by metabolic reprogramming of macrophages. *Science* 356, 513519 (2017).
54. Puleston, D. J., et al. Polyamines and eIF5A Hypusination Modulate Mitochondrial Respiration and Macrophage Activation. *Cell Metab* 30, 352-363 e358 (2019).
55. Zhang, S., et al. Efferocytosis Fuels Requirements of Fatty Acid Oxidation and the Electron Transport Chain to Polarize Macrophages for Tissue Repair. *Cell Metab* 29, 443-456 e445 (2019).
56. Sanin, D. E., et al. Mitochondrial Membrane Potential Regulates Nuclear Gene Expression in Macrophages Exposed to Prostaglandin E2. *Immunity* 49, 1021-1033 e1026 (2018).
57. Zhou, Y., et al. Leptin Deficiency Shifts Mast Cells toward Anti-Inflammatory Actions and Protects Mice from Obesity and Diabetes by Polarizing M2 Macrophages. *Cell Metab* 22, 1045-1058 (2015).
58. Huang, S. C., et al. Metabolic Reprogramming Mediated by the mTORC2-IRF4 Signaling Axis Is Essential for Macrophage Alternative Activation. *Immunity* 45, 817-830 (2016).
59. Morioka, S., et al. Efferocytosis induces a novel SLC program to promote glucose uptake and lactate release. *Nature* 563, 714-718 (2018).
60. Chandran, V., et al. A Systems-Level Analysis of the Peripheral Nerve Intrinsic Axonal Growth Program. *Neuron* 89, 956-970 (2016).
61. Abe, N. & Cavalli, V. Nerve injury signaling. *Curr Opin Neurobiol* 18, 276-283 (2008).
62. Jha, M. K., et al. Monocarboxylate transporter 1 in Schwann cells contributes to maintenance of sensory nerve myelination during aging. *Glia* 68, 161-177 (2020).
63. Zurborg, S., et al. Generation and characterization of an Advillin-Cre driver mouse line. *Mol Pain* 7, 66 (2011).
64. Madisen, L., et al. A robust and high-throughput Cre reporting and characterization system for the whole mouse brain. *Nat Neurosci* 13, 133-140 (2010).
65. Pullen, T. J., da Silva Xavier, G., Kelsey, G. & Rutter, G. A. miR-29a and miR-29b contribute to pancreatic beta-cell-specific silencing of monocarboxylate transporter 1 (Mct1). *Mol Cell Biol* 31, 3182-3194 (2011).
66. Ma, C. H., et al. Accelerating axonal growth promotes motor recovery after peripheral nerve injury in mice. *J Clin Invest* 121, 4332-4347 (2011).
67. Painter, M. W., et al. Diminished Schwann cell repair responses underlie age-associated impaired axonal regeneration. *Neuron* 83, 331-343 (2014).
68. Viader, A., et al. Aberrant Schwann cell lipid metabolism linked to mitochondrial deficits leads to axon degeneration and neuropathy. *Neuron* 77, 886-898 (2013).
69. Macpherson, P. C., Farshi, P. & Goldman, D. Dach2-Hdac9 signaling regulates reinnervation of muscle endplates. *Development* 142, 4038-4048 (2015).
70. Zhang, X., Goncalves, R. & Mosser, D. M. The isolation and characterization of murine macrophages. *Curr Protoc Immunol* Chapter 14, Unit 14 11 (2008).
71. Jha, M. K., et al. Metabolic Connection of Inflammatory Pain: Pivotal Role of a Pyruvate Dehydrogenase Kinase-Pyruvate Dehydrogenase-Lactic Acid Axis. *J Neurosci* 35, 14353-14369 (2015).
72. Yang, Y., et al. Metabolic reprogramming for producing energy and reducing power in fumarate hydratase null cells from hereditary leiomyomatosis renal cell carcinoma. *PLoS One* 8, e72179 (2013).
73. Mookerjee, S. A. & Brand, M. D. Measurement and Analysis of Extracellular Acid Production to Determine Glycolytic Rate. *J Vis Exp*, e53464 (2015).
74. Mookerjee, S. A., Gerencser, A. A., Nicholls, D. G. & Brand, M. D. Quantifying intracellular rates of glycolytic and oxidative ATP production and consumption using extracellular flux measurements. *J Biol Chem* 292, 7189-7207 (2017).
75. Mookerjee, S. A., Goncalves, R. L. S., Gerencser, A. A., Nicholls, D. G. & Brand, M. D. The contributions of respiration and glycolysis to extracellular acid production. *Biochim Biophys Acta* 1847, 171-181 (2015).
76. Lee, Y., et al. Oligodendroglia metabolically support axons and contribute to neurodegeneration. *Nature* 487, 443-448 (2012).
77. Scheib, J. L. & Hoke, A. An attenuated immune response by Schwann cells and macrophages inhibits nerve regeneration in aged rats. *Neurobiol Aging* 45, 1-9 (2016).
78. Oh, M. H., et al. mTORC2 Signaling Selectively Regulates the Generation and Function of Tissue-Resident Peritoneal Macrophages. *Cell Rep* 20, 2439-2454 (2017).
79. Chow, C.-W., Downey, G. P. and Grinstein, S. Measurements of Phagocytosis and Phagosomal Maturation. *Current Protocols in Cell Biology*, 22: 15.7.1-15.7.33(2004).

What is claimed is:

1. A method of increasing macrophage peripheral nerve regeneration activity comprising:
    contacting a macrophage isolated from a blood or bone marrow sample with a viral vector, wherein the viral vector comprises a polynucleotide encoding MCT1 operably linked to a regulatory sequence,
    thereby increasing macrophage peripheral nerve regeneration activity as compared to a reference macrophage,
    wherein the macrophage peripheral nerve regeneration activity is selected from the group consisting of macrophage glycolytic and mitochondrial activities, phagocytosis activity, production of pro-regenerative cytokines, production of pro-inflammatory cytokines, modulation of nerve conduction velocity (NCV), modulation of compound muscle action potential (CMAP), modulation of neuromuscular junction (NMJ) reinnervation, and combinations thereof.

2. The method of claim 1, wherein the viral vector is a lentiviral vector.

3. The method of claim 1, wherein phagocytosis activity comprises axonal phagocytosis and myelin debris phagocytosis.

4. The method of claim 1, wherein the pro-regenerative cytokines are selected from the group consisting of IL-10, IL-21R, and TGF-β.

5. The method of claim 1, wherein the pro-inflammatory cytokines are selected from the group consisting of IL-1β, TNF-α, IL-6, IL-12, IL-15 and IL-23.

6. A method of inducing peripheral nerve regeneration of an injured nerve in a subject comprising:
contacting a macrophage, isolated from blood or bone marrow of the subject, with a viral vector comprising a polynucleotide encoding an MCT1 gene to produce a macrophage having increased nerve regenerating activity as compared to a reference macrophage that has not been contacted with a vector including a polynucleotide encoding MCT1;
administering to the subject, at an injury site or at an adjacent site to the injury site, a macrophage composition, wherein the macrophage composition comprises:
(a) the macrophage having increased nerve regenerating activity as compared to
the reference macrophage; and
(b) a pharmaceutically acceptable carrier,
thereby inducing nerve regeneration of an injured peripheral nerve in the subject.

7. The method of claim 6, wherein the reference macrophage is a macrophage that has not been contacted with a viral vector comprising a polynucleotide encoding MCT1.

8. The method of claim 6, wherein the viral vector is a lentiviral vector.

9. The method of claim 6, wherein the macrophage having increased nerve regenerating activity has increased glycolytic and mitochondrial functions as compared to a reference macrophage that has not been contacted with a vector including a polynucleotide encoding MCT1.

10. The method of claim 6, wherein the macrophage having increased nerve regenerating activity has an increased phagocytosis function as compared to a reference macrophage that has not been contacted with a vector including a polynucleotide encoding MCT1.

11. The method of claim 10, wherein the increased phagocytosis function comprises an increased axonal phagocytosis and an increased myelin debris phagocytosis.

12. The method of claim 6, wherein the macrophage having increased nerve regenerating activity has an increased production of pro-regenerative cytokines as compared to a reference macrophage that has not been contacted with a vector including a polynucleotide encoding MCT1.

13. The method of claim 6, wherein the macrophage having increased nerve regenerating activity has a decreased production of pro-inflammatory cytokines as compared to a reference macrophage that has not been contacted with a vector including a polynucleotide encoding MCT1.

14. The method of claim 6, wherein the injured nerve results from a trauma or inflammation.

15. The method of claim 6, wherein inducing nerve regeneration in the subject comprises increasing neuroimmune interaction at a nerve injury site.

16. The method of claim 6, wherein inducing nerve regeneration in the subject comprises increasing nerve conduction velocity (NCV) after a nerve injury.

17. The method of claim 6, wherein inducing nerve regeneration in the subject comprises increasing compound muscle action potential (CMAP) after a nerve injury.

18. The method of claim 6, wherein inducing nerve regeneration in the subject comprises increasing neuromuscular junction (NMJ) reinnervation after a nerve injury.

19. The method of claim 6, wherein inducing nerve regeneration in the subject comprises accelerating nerve regeneration in the subject after a nerve injury.

20. The method of claim 6, wherein administering the macrophage composition comprises intravenous, intraperitoneal and intraarterial administrations.

21. The method of claim 6, wherein administering the macrophage composition comprises administering the macrophage composition in close proximity to the injured nerve.

22. The method of claim 6, wherein administering the macrophage composition is at a timepoint when circulating macrophages infiltrate the injured nerve.

23. The method of claim 22, wherein administering the macrophage composition is at about 3 days following sciatic nerve crush.

24. The method of claim 6, wherein an effective dose of the macrophage composition comprises about $5 \times 10^6$ cells/100 uL of macrophages.

* * * * *